US006413731B1

(12) United States Patent
Borowsky et al.

(10) Patent No.: US 6,413,731 B1
(45) Date of Patent: Jul. 2, 2002

(54) METHODS OF SCREENING FOR COMPOUNDS WHICH BIND TO A HUMAN SNORF36A RECEPTOR

(75) Inventors: Beth E. Borowsky, Montclair; Kristine L. Ogozalek, Rochelle Park; Parul P. Lakhlani, Paramus; Nika Adham, Ridgewood, all of NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/518,914

(22) Filed: Mar. 3, 2000

Related U.S. Application Data

(63) Continuation-in-part of application No. 09/303,593, filed on May 3, 1999, now abandoned.

(51) Int. Cl.[7] .......................... G01N 33/53; C12N 5/10; C12N 15/12; C12N 15/62
(52) U.S. Cl. ...................... 435/7.8; 435/69.1; 435/71.1; 435/71.2; 435/471; 435/325; 435/320.1; 435/252.3; 536/23.5; 530/350
(58) Field of Search ................................ 536/23.1, 23.5; 530/350; 435/69.1, 7.8, 71.2, 71.1, 325, 471, 320.1, 252.3

(56) References Cited

U.S. PATENT DOCUMENTS 6,008,338 A   12/1999   Fong .......................... 536/23.5

OTHER PUBLICATIONS

Provencio, I. et al., Melanopsin: An opsin in Melanophores, Brain and Eye, Proc. Ntl. Acad. Sci., Jan. 1998, vol. 95, pp. 340–345.

*Primary Examiner*—Prema Mertz
(74) *Attorney, Agent, or Firm*—John P. White; Cooper & Dunham LLP

(57) ABSTRACT

This invention provides isolated nucleic acids encoding mammalian SNORF36 receptors, purified mammalian SNORF36 receptors, vectors comprising nucleic acid encoding mammalian SNORF36 receptors, cells comprising such vectors, antibodies directed to mammalian SNORF36 receptors, nucleic acid probes useful for detecting nucleic acid encoding mammalian SNORF36 receptors, antisense oligonucleotides complementary to unique sequences of nucleic acid encoding mammalian SNORF36 receptors, transgenic, nonhuman animals which express DNA encoding normal or mutant mammalian SNORF36 receptors, methods of isolating mammalian SNORF36 receptors, methods of treating an abnormality that is linked to the activity of the mammalian SNORF36 receptors, as well as methods of determining binding of compounds to mammalian SNORF36 receptors, methods of identifying agonists and antagonists of SNORF36 receptors, and agonists and antagonists so identified.

36 Claims, 35 Drawing Sheets

FIGURE 1A

```
  1  CAACTCAGGATGAACCCTCCTTCGGGGCCAAGAGTCCCGCCCAGCCCAACCCAAGAGCCC    60
 61  AGCTGCATGGCCACCCCAGCTGGTGGGACAGCTCCCAGAGCAGCATCTCC            120
121  AGCCTGGGCCGGCTTCCATCCATCAGTCCCACAGCACCTGGGACTTGGGCTGCTGCCTGG   180
181  GTCCCCCTCCCCACGGTTGATGTTCCAGACCATGCCCAACCTGACGGTCATCTATACCCTTCTGCAGG   240
241  TTGCTGGTGGGACTCACGGGGATGCTGGGCAACATGTTCATTATCAACCTGCCGGTCAGGCGACTTC   300
301  AGCAGAAGCCTCCGGACACCTGCCAACATGTTCATTATCAACCTGCCGGTCAGGCGACTTC         360
361  CTCATGTCCTTCACCCAGGCCCCTGTCTCTTCACCAGTAGCCTCTATAAGCAGTGGCTC           420
421  TTTGGGAGACAGGCTGCGAGTTCTATGCCTTCTGTGGAGCTCTCTTTGGCATTCCCTCC          480
481  ATGATCACCCTGACCGGTACCTGGACCGGTACCTGGTAATCACACGCCCGCTGGCC             540
541  ACCTTTGGTGTGGCGTCCAAGAGGCGTGCGGGCATTTGTCCTGGGCGTTGGCTCTAT            600
601  GCCCTGGCCTGGAGTCTGCCACCCTTCTTCGGCTGGAGCGCTACGTGCCCGAGGGGTTG           660
661  CTGACATCCTGCTCCTGGGACTACATGAGCTTCACGCCGTGCCTACACCATG               720
```

FIGURE 1B

```
 721  CTTCTCTGCTTCGTGTTCTTCCTCCCTCTGCTTATCATCATCTACTGCTACATCTTC   780
 781  ATCTTCAGGGCCATCCGGGAGACAGGAGCTCTCCAGACCTTCGGGGCTGCAAGGGC    840
 841  AATGGCGAGTCCCTGTGGCAGCGGCTGCAGAGCGAGTGCAAGATGCCAAGATC       900
 901  ATGCTGCTGGTCATCCTCCTCTTCGTGCTCTCCCTGGCTCCCTATTCCGCTGTGCCCTG 960
 961  GTGGCCTTTGCTCTGGGTACGCCACACGTCCTGACACCCTACATGAGCTCGGTGCCAGCCGTC 1020
1021  ATCGCCAAGGCCTCTGCAATCCACAACCCCATCATTTACGCCATCACCCCAAGTAC    1080
1081  AGGGTGGCCATTGCCCAGCACCTGCCCTGCCTGGGGGTGCTGTGGTGTATCACGCCCGG 1140
1141  CACAGTCGCCCCTACCCCCAGCTCTCCACCGCTCGACCAGCCACACC              1200
1201  TCCAACCTCAGCTGGATCTCCATACGGAGGCAGCAGGAGTCCCTGGGCTCGGAGAGTGAG 1260
1261  GTGGGCTGGACACACATGGAGGCAGCAGCTGTGTGGGGAGCTGCCCAGCAAGCAAATGGG  1320
1321  CGGTCCCTCTACGGTCAGGGTCTGGAAGCTTGGAAGCCAAGGCACCCCAGACCCCAG     1380
1381  GGACACGAAGCAGAGACTCCAGGGAAGACCAAGGGGCTGATCCCCAGCCAGGACCCCAGG  1440
```

FIGURE 1C

1441 ATGTAGGACGCCCACTGGCCTCTCCCCTTTCTTCTGAGACACATCCAGCCCCCCACGTCTC 1500

1501 CCTCATAT 1508

```
1    CAACTCAGGATGAACCCTCCTTCGGGGCCAAGAGTCCCGCCCAGCCCAACCCAAGAGCCC     60
61   AGCTGCATGGCCACCCCAGCACCCAGCTGGTGGGACAGCTCCCAGAGCAGCATCTCC      120
121  AGCCTGGGCCGGCTTCCATCCATCAGTCCCACAGCACTTGGGACTTGGCTGCTGCCTGG    180
181  GTCCCCCTCCCCACGGGTTGATGTTCCAGACCATGCCCACTATACCCTTCTGCAGA       240
241  TTGCTGGTGGGACTCAGGGGATGCTGGGCAACCTGACGGTCATCTATAGCCTCTGCAGA    300
301  GCTGTGCTTCGTGGAGTCACTGTGATGATGCAGAGCAGAAGCCTCCGGACACCTGCCAAC   360
361  ATGTTCATTATCAACCTCGCGGTCAGCGACTTCCTCATGTCCTTCACCCAGGCCCCTGTC   420
421  TTCTTCACCAGTAGCCTCTATAAGCAGTGGCTCTTTGGGGAGACAGGCTGCGAGTTCTAT   480
481  GCCTTCTGTGAGCTCTTTGGCATTCCTCCATGATCACCCTGACGGCCATCGCCCCTG      540
541  GACCGCTACCTGGTAATCACACGCCCGCTTGGTGTGGCTCCAAGAGGCGT             600
601  GCGGCATTTGTCCTGCGTTTGGCTCTTATGCCCTGGCCTGGAGTCTGCCACCCTTC       660
661  TTCGGCTGGAGCGCCTACGTGCCCGAGGGGTTGCTGACATCCTGCTCCTGGACTACATG    720
```

FIGURE 3B

```
 721  AGCTTCACGCGGCCGTGCCTACACCATGCTTCTCTGCTTCTGTGTTCTTCCTC   780
 781  CCTCTGCTTATCATCATCTACTGCTACATCTTCATCTTCAGGGCCATCCGGGAGACAGGA   840
 841  CGGGCTCTCCAGAGACCTTCGGGGCCCTGCAAGGCAATGGCGAGTCCCTGTGGCAGCGGCAG   900
 901  CGGCTGCAGAGCGAGTGCAAGATCATGCTGTGGTCATCCTCCTCTTCGTG   960
 961  CTCTCCCTGGGCTCCCTATTCCGCTGTGTGGGCCCTTTGCTGGTACGCACACGTC   1020
1021  CTGACACCCTACATGAGCTCGGTGCCCAGCCGTCATCGCCAAGGCCTCTGCAATCCACAAC   1080
1081  CCCATCATTTACGCCATCACCACCCCAAGTACAGGGTGGCCATTGCCCAGCACCTGCCC   1140
1141  TGCCTGGGGGTGCTGCTGGGTGTATCACGCCACAGTCGCCGGCACCTCCAACCTCCAGCTACCGC   1200
1201  TCCACCCACGCTCCCACGCTGACCAGCACCTCCAACCTCCAGCTGGATCTCCATACGG   1260
1261  AGGCGCCAGGAGTCCCTGGGCTCGGAGAGTGAGGTGGGCTGGACACACATGGAGGCAGCA   1320
1321  GCTGTGTGTGGGAGCTGCCCAGCAAGCAAATGGGCGGTCCCTCTACGGTCAGGGTCTGGAG   1380
1381  GACTTGGAAGCCAAGGCACCCCCAGACCCCCAGGGACACGAAGCAGAGACTCCAGGGAAG   1440
```

FIGURE 3C

```
1441  ACCAAGGGGCTGATCCCCAGCCAGGACCCCCAGGATGTAGGACGCCCACTGGCTCTCCCTT  1500
1501  TCTTCTGAGACACATCCAGCCCCCACGTCTCCCCTCATAT                       1541
```

```
1    CATAGCCATGGACCGGCTATCTGGTGATCACACGTCCACTGGCCACCATCGGCCATGAGATC    60
61   CAAGAGACGGGACGGCACTAGTCCTGCTAGGTGTCTGGCTCTATGCCCTGGCCTGGAGTCT    120
121  GCCGCCTTTCTTTGGCTGTGGAGCGCCTACGTGCCCGAGGGGCTGCTGACATCCTGCTCCTG   180
181  GGACTACGTGACCTTCACGCCCCCTCGTGCCGCCTACACCATGCTGCTCTTCTGCTTTGT   240
241  CTTCTTCCCTC                                                    250
```

```
Rat SNORF36    1 ..............................................CATAGCCATGGA 12
                                                                ||| ||| ||||
Hum SNORF36  451 GCTCTCTTTGGCATTCCTCCATGATCACCCTGACGGCCATCGCCCCTGGA 500

Rat SNORF36   13 CCGCTATCTGGTGATCACACGTCCACTGGCCACCATCGGCATGAGATCCA 62
                 ||||||||| ||| ||| ||  ||| ||||| ||||||||||||  ||||
Hum SNORF36  501 CCGCTACCTGGTAATCACACGCCCGCTGGCCACCTTTGGTGTGGCGTCCA 550

Rat SNORF36   63 AGAGACGGACGGCACTAGTCCTGCTAGGTGTCTGGCTCTATGCCCTGGCC 112
                 |||| ||| ||||| || ||||||| |||||||| ||||||||||||||
Hum SNORF36  551 AGAGGCGTGCGGCATTTGTCCTGCTGGGCGTTTGGCTCTATGCCCTGGCC 600

Rat SNORF36  113 TGGAGTCTGCCGCCTTTCTTTGGCTGGAGCGCCTACGTGCCCGAGGGGCT 162
                 |||||||||||||||| || |||||||||||||||||||||||||||| 
Hum SNORF36  601 TGGAGTCTGCCCACCCTTCTTCGGCTGGAGCGCCTACGTGCCCGAGGGGTT 650
```

FIGURE 7B

```
Rat SNORF36  163  GCTGACATCCCTGCTCCTGGGACTACGTGACCTTCACGCCCCTCGTGCGCG  212
                  |||||||||||||||||||||||||||  ||  |||||||  |||||||
Hum SNORF36  651  GCTGACATCCCTGCTCCTGGGACTACATGAGCTTCACGCCGGCCGTGCGTG  700

Rat SNORF36  213  CCTACACCATGCTGCTCTTCTGCTTTGTCTTCCTC..........       250
                  ||||||||||||||||| |||  ||  |||| |
Hum SNORF36  701  CCTACACCATGCTTCTCTGCTGTTCGTGTTCCTGCTCCCCTCTGCTTATC  750
```

FIGURE 8

```
Rat SNORF36    1   ..............IAMDRYLVITRPLATIGMRSKRRTALVLLGVWLYALA  37
                                 ||:|||||||||||||||| |  |||  ||||||||||||
Hum SNORF36  151  ALFGISSMITLTAIALDRYLVITRPLATFGVASKRRAAFVLLGVWLYALA 200

Rat SNORF36   38  WSLPPFFGWSAYVPEGLLTSCSWDYVTFTPLVRAYTMLLFCFVFFL.....  83
                  |||||||||||||||||||||||||||||:||:|||||||||| ||||
Hum SNORF36  201  WSLPPFFGWSAYVPEGLLTSCSWDYMSFTPAVRAYTMLLCCFVFFLPLLI 250
```

FIGURE 9A

```
1    TTTAAGTCCTCCAAGAGCCTGAGCATGAACTCTCCTTCAGAATCAAGAGTCCCTTCAAGC    60
61   TTAACTCAGGATCCCAGCTTTACCGCCAGCCCTCCTACAAGGCATTGGAACAGC         120
121  ACTCAGAACATCTCCGTCAGAGTCCAGCTTCTATCCGTTAGCCCCACGACACCTGGGCTT   180
181  CAGGCTGCTGCCTGGGTCCCCTTCCCCACAGTCGACGTCCCCAGATCATGCTCACTATACC  240
241  CTAGGCACGGTGATCCTGCTGGTGGGACTCACAGGGATGCTGGGTAACCTGACAGTCATC   300
301  TACACCCTTCTGCAGGAATAGAGGCCTGCGGACACCGGCAAACATGCTCATCATCAACCTG  360
361  GCAGTCAGGCGACTTCCTTATGTCGTTCACTCAGGCCCCGGTCTCTTCTTTGCCAGCAGCCTC 420
421  TACAAGAAGTGGCTCTTCGGGGAGACAGGTTGCAAGTTCTATGCCTTCTGTGGGGCTGTC   480
481  TTTGGCATCGTTCCATGATCACCCTGACAGCCATGAGCCATGGACCGCTATCGGTGATC    540
541  ACACGTCCACTGGCCCACCATCGGCCATGAGATCCAAGAGACGGCACTAGTCCTGCTA     600
601  GGTGTCTGGCTCTATGCCCTGGCCTGCGCCTTTCTTGGCTGGAGCGCCTAC            660
```

FIGURE 9B

```
 661  GTGCCCGAGGGGCTGCTGACATCCTGCTCCTGGGACTACGTGACCTTCACGCCCCTCGTG   720
 721  CGGCGCCTACACCATGCTGCTCTTCTTGCTTTGTCTTCCCTCCTCTGCTCATTATCATC    780
 781  TTCTGCTACATCTTCATCTTCAGGGCCATTCGAGAGACAGGCCGGGCCTGTGAGGGCTGT   840
 841  GGTGAGTCCCCTGCGGGCGGCAGTGGCAGCGGCTACAGAGTGAATGGAAGATGGCC       900
 901  AAGGTCGCACTGATCGTCATTCTCCTCTTTGTCTGTCCCTGGGCTCCCTACTCCACTGTG   960
 961  GCCCTGGTGGGCTTTGCTGGGTACTGCACATCCTGACGCCCTACATGAGCTCGGTGCCA   1020
1021  GCCGTCATTGCCAAGGCCTCGGCCATTGCTGCCATTCCACAATCCTATCATCATCACCCC   1080
1081  AAGTACAGGGGCGGCCATTGCTTCAGCACTTGCCCTTGCCCTTGGGGTGCTTCTTGGAGTATCA   1140
1141  GGCCAGCGCCAGCCACCGTCCCTCCAGCTACCGCTCCACCCATCGCTCCACACTGAGCAGC   1200
1201  CAGTCCTCAGACCTCTCAGCTGGATCTCTGGGCAGAAGCGCCAAGAGTCCCTGGTTCTGAG   1260
1261  AGTGAAGTGGGCTGGACAGACACAGAAACAACAGCTGCGTGGGAGCTGCCCAGCAAGCA   1320
```

FIGURE 9C

```
1321  AGTGGACAATCCTTCTGCAGTCATGACCTGGAAGATGGAGAAGTCAAGGCTCCTTCCAGC  1380
1381  CCCCAGGAACAGAAATCCAAGACTCCCAAGACCAAGAGACACCTCCCCAGTCTGGACCGA  1440
1441  AGGATGTAGGATGCCCCAGTCCCCGTCCCCCTCCCT                          1473
```

```
hSNORF36a    1 ATGAACCCTCCTTCGGGGCCAAGAGTCCCGCCCAGCCCAACCCAAGAGCC   50
               |||||||||||| |||||||||  ||||||| ||||||  |||||| ||
rSNORF36     1 ATGAACTCTCCTTCAGAATCAAGAGTCCCTTCAAGCTTAACTCAGGATCC   50 hSNORF36a   51 CAGCTGCATGGCCACCCAGCACCACCCCAGCTGTGGGACAGTCCCAGA   100
               |||||| |||  |||| ||  |||| | ||| ||||||| ||| ||
rSNORF36    51 CAGCTTTACCGCCAGCCCTGCCCTCCTACAAGGCATTTGGAACAGCACTC   100 hSNORF36a  101 GCAGCATCTCCAGCGCCTGGGCTTCCATCAGTCCCACAGCACCT   150
               |||||||| || |  ||||||  |||| ||||| |||| |||
rSNORF36   101 AGAACATCTCCGTCAGAGTCCAGCTTCTATCCGTTAGCCCCACGACACCT   150 hSNORF36a  151 GGGACTTGGGCTGCTGCCTGGGTCCCCCACGGTTGATGTTCCAGA   200
               |||| ||||| | ||||||||  |||||  |||||  |  ||| |
rSNORF36   151 GGGCTTCAGGCTGCTGCGTGGGTCCCCACAGTCGACGTCCCAGA   200 hSNORF36a  201 CCATGCCCACTATACCCTGGGCAACAGTGATCTTGCTGGTGGGACTCACGG   250
               |||||  |||||||||| ||| ||||||||  |||||||  |||||||
rSNORF36   201 TCATGCTCACTATACCCTAGGCACACGGTGATCCTGCTGGTGGGACTCACAG   250 hSNORF36a  251 GGATGCTGGGCAACCTGACGGTCATCTATACCTTCTGCAGGAGCAGAAGC   300
               |||||||||  ||||| |||  ||||||| |||||| || ||||
rSNORF36   251 GGATGCTGGGTAACCTGACAGTCATCTACACCTTCTGCAGGAATAGAGGC   300 hSNORF36a  301 CTCCGGACACCTGCCAACATGTTCATTATCAACCTCGCGGTCAGCGACTT   350
               || ||| ||  ||||  ||| ||||  ||| |||| |||| |||||||
rSNORF36   301 CTGCGGACACCGGCAAACATGCTCATCATCAACCTGGCAGTCAGCGACTT   350 hSNORF36a  351 CCTCATGTCCTTCACCCAGCCCCTGTCTTCTTCACCAGTAGCCTCTATA   400
               ||| |||||| || ||||| |||||||| || |||||||||| |||
rSNORF36   351 CCTTATGTCGTTCACTCAGGCCCCGGTCTTCTTTGCCAGCAGCCTCTACA   400
```

FIGURE 11B

```
hSNORF36a  401 AGCAGTGGCTCTCTTTGGGGAGACAGGCTGCGAGTTCTATGCCTTCTGTGGA 450
                ||  ||||||||| ||| ||||||||||||| |||||||||||||||||||
rSNORF36   401 AGAAGTGGCTCTCTTCGGGGAGACAGGTTGCAAGTTCTATGCCTTCTGTGGG 450 hSNORF36a  451 GCTCTCTTTGGCATTCCTCCATGATCACCCTGACGGCCATCGCCCCTGGA 500
               |||  ||||||||||  |||||||||||| |||||||| ||||| ||||
rSNORF36   451 GCTGTCTTTGGCATCGTTCCATGATCACCCTGACAGCCATAGCCATGGA 500 hSNORF36a  501 CCGCTACCTGGTAATCACACGCCCCGCTGGCCACCTTTGGTGTGGCGTCCA 550
               ||||||| ||||| ||||||||| || ||||| ||  || ||| ||||||
rSNORF36   501 CCGCTATCTGGTGATCACACGTCCACTGGCCACCATCGGCATGAGATCCA 550 hSNORF36a  551 AGAGGGCGTGCGGCATTTGTCCTGCTGGGCGTTTGGCTCTATGCCCTGGCC 600
               | ||  ||| ||| ||||| ||||||   |||| ||||||||||||||||
rSNORF36   551 AGAGACGGACGGCACTAGTCCTGCTAGTGTGTCTGGCTCTATGCCCTGGCC 600 hSNORF36a  601 TGGAGTCTGCGCCACCCCTTCTTCGGCTGGAGCGCCTACGTGCCCGAGGGTT 650
               |||||||||| |||  |||||||| ||||||||||||||||||||||| ||
rSNORF36   601 TGGAGTCTGCCCCGCTTTCTTCTTTGGCTGGAGCGCCTACGTGCCCGAGGGCT 650 hSNORF36a  651 GCTGACATCCTGCTCCCTGGGACTACATGAGCTTCACGCCGGCCGTGCGTG 700
               |||||||||||||||| ||||||||| |||  ||| |||| ||||||| |
rSNORF36   651 GCTGACATCCTGCTCCGCTGGGACTGACCTTCACGCTGACCTTCACGCCCCCTCGTGCGCG 700 hSNORF36a  701 CCTACACCATGCTTCTCTGCTGTCTTGTCTTCCTCCCTCTGCTTATC 750
               |||||||||||||||||||||||| || ||||| |||||||||| ||
rSNORF36   701 CCTACACCATGCTTCTCTGCTTTGTCTTCTTCCTCCCTCTGCTCATT 750 hSNORF36a  751 ATCATCTACTGCTACATCTTCAGGGCCATCCGGGAGAGACAGGACG 800
               |||||||| |||||||||||||||||||| ||||||| ||||||
rSNORF36   751 ATCATCTTCTGCTACATCTTCATCTTCAGGGCCATTCGAGAGACAGGCCG 800
```

FIGURE 11C

```
hSNORF36a   801  GGCTCTCCAGACCTTCGGGGCCTGCAAGGGCAATGGCGAGTCCCTGTGGC  850
                 ||   ||||  ||                 |   |||  ||  |||||||
rSNORF36    801  GG..........CCTGTGAGGGCTGTGGTGAGTCCCCTCTGCGGGCGGGC  841 hSNORF36a   851  AGCGGCAGCGGCTGCAGAGCGAGTGCAAGATGCCAAGATCATGCTGCTG   900
                 | ||| ||||||||| ||||| ||||| |||||||  ||  |  ||| 
rSNORF36    842  AGTGGCAGCGGCTACAGAGAGTGAATGAAGATGAAGATGCCAAGGTCGCACTGATC  891 hSNORF36a   901  GTCATCCTCCTCTTCGTGCTCTCCCTGGGCTCCCTATTCCGCTGTGGCCCT  950
                 ||||| || |||| |||||| ||| ||||||||| ||||| | ||||||||
rSNORF36    892  GTCATTCTCCCTCTTTGTGCTGTGTCCTGGGCTCCTACTCCACTGTGGCCCT  941 hSNORF36a   951  GGTGGCCTTTGCTGGGTACGCACACGTCCTGACACCCTACATGAGCTCGG  1000
                 ||||||| ||||||||| ||||| |||| |||||||||||||||||||||
rSNORF36    942  GGTGGGCTTTGCTGGGTACTCGGGTACCCTGACGCCCTACATGAGCTCGG  991 hSNORF36a   1001 TGCCAGCCGTCATGCCAAGGCCTCTGCAATCCACAACCCCATCATTTAC   1050
                 ||||||||||||| ||||||||| |||||| ||||| || |||| |||| 
rSNORF36    992  TGCCAGCCGTCATTGCCAAGGCCCATCCGGCCATTGCTCAGCACTTGCCTTG  1041 hSNORF36a   1051 GCCATCACCCACCCCAAGTACAGGGTGGCCATTGCCCGGCACAGTCGCCCCTG  1100
                 |||||| ||| ||||||||||||| ||||| |||||||||  |||  ||||||
rSNORF36    1042 GCCATCACTCACCCCAAGTACAGGGCGGCCATTGCTCAGCACTTGCCTTG   1091 hSNORF36a   1101 CCTGGGGGTGCTGCTGGGTGTATCACGCCGGCACAGTCGCCCCTACCCCA  1150
                 || ||||| ||||| |||| |||| ||||| |||||| ||| |||||| ||
rSNORF36    1092 CCTTGGGGGTGCTTCTTGGAGTATCAGGCGCAGCCGCAGCCGCCCACCCCTCA  1141 hSNORF36a   1151 GCTACCGCTCCACCACCGCTCCACGCTGACCAGCAGCCACACCTCCAACCTC  1200
                 ||||||||||||| |||||||||| |||||||||||||| ||||| ||||||
rSNORF36    1142 GCTACCGCTCTACCCATCGCTCCACACTGCTCCACACGAGCAGCCAGTCCTCCTCAGACCTC  1191
```

FIGURE 11D

```
hSNORF36a  1201  AGCTGGATCTCCATACGGAGGCGCCAGGAGTCCCTGGGCTCGGAGAGTGA  1250
                 ||||||||||||  ||  ||  ||||||||||  ||||||  |||||||||
rSNORF36   1192  AGCTGGATCTCTGGGCAGAGCGCCAAGAGTCCCTGGTTCTGAGAGTGA    1241 hSNORF36a  1251  GGTGGGCTGGACACACATGGAGGCAGCAGCTGTGTGGGAGCTGCCCAGC   1300
                 ||||||||||||||||  ||||||||||||||||  ||||||||||||||||
rSNORF36   1242  AGTGGGCTGGACACACAGAAACAACAGCTGCGTGGGGAGCTGCCCAGC    1291 hSNORF36a  1301  AAGCAAATGGGCGTCCCTCTACGGTCTCAGGTCTCTGGAGGACTTGGAAGCC  1350
                 ||||||  |||| ||  ||  ||||  |||||| ||||||||| ||||||||
rSNORF36   1292  AAGCAAGTGGACAATCTTCTGCAGTCATGACCTGGAAGATGGAGAAGTC    1341 hSNORF36a  1351  AAGGCACCCCCCAGACCCCAGGGACGAAGCAGAGACTCCAGGGAAGAC    1400
                 |||||  |||||||||  ||||||||||||||||||||||||| |||||
rSNORF36   1342  AAGGCTCCTTCCAGCCCCCAGGAACAGAAATCCAAGACTCC...CAAGAC  1388 hSNORF36a  1401  CAAGGGGCTGATCCCCAGCCAGGACCCCCAGGATGTAG              1437
                 ||||  ||||  ||||  ||  ||||| |||||| ||||||
rSNORF36   1389  CAAGAGACACCTCCCCAGTCTGGACCGAAGGATGTAG                1425
```

FIGURE 12A

```
hSNORF36a    1 MNPPSGPRVPPSPTQEPSCMATPA..PPSWDSSQSSISSLGRLPSISPTA  49
               ||| || ||  ||    | ::|    | :|:  . :|   | .|||
rSNORF36     1 MNSPSESRVPSSLTQDPSFTASPALLQGIWNSTQ.NISVRVQLLSVSPTT  49 hSNORF36a   50 PGTWAAAWVPLPTVDVPDHAHYTLGTVILLVGLTGMLGNLTVIYTFCRSR  99
               || |||||| |||||||||||||||||||||||||||||||||||||
rSNORF36    50 PGLQAAAWVPFPTVDVPDHAHYTLGTVILLVGLTGMLGNLTVIYTFCRNR  99 hSNORF36a  100 SLRTPANMFIINLAVSDFLMSFTQAPVFFTSSLYKQWLFGETGCEFYAFC 149
               ||||||||| ||||||||||||||||||||||:||| |||||||| |||
rSNORF36   100 GLRTPANMLIINLAVSDFLMSFTQAPVFFASSLYKKWLFGETGCKFYAFC 149 hSNORF36a  150 GALFGISSMITLTAIALDRYLVITRPLATFGVASKRRAAFVLLGVWLYAL 199
               || ||:|||||||||| |||||||||||| |.|||||| ||||||||||
rSNORF36   150 GAVFGIVSMITLTAIAMDRYLVITRPLATIGMRSKRRTALVLLGVWLYAL 199 hSNORF36a  200 AWSLPPFFGWSAYVPEGLLTSCSWDYMSFTPAVRAYTMLLCCFVFFLPLL 249
               |||||||||||||||||||||||||| ||.||:|||||||| |||||||
rSNORF36   200 AWSLPPFFGWSAYVPEGLLTSCSWDYVTFTPLVRAYTMLLFCFVFFLPLL 249 hSNORF36a  250 IIIYCYIFIFRAIRETGRALQTFGACKGNGESLWQR...QRLQSECKMAK 296
               |||:|||||||||||||||           |  .| ||||||| ||||
rSNORF36   250 IIIFCYIFIFRAIRETGR......ACEGCGESPLRRQWQRLQSEWKMAK 293 hSNORF36a  297 IMLLVILLFVLSWAPYSAVALVAFAGYAHVLTPYMSSVPAVIAKASAIHN 346
               :.|:|||||||||||||||:|||||| ||||||||||||||||||||||
rSNORF36   294 VALIVILLFVLSWAPYSTVALVGFAGYSHILTPYMSSVPAVIAKASAIHN 343 hSNORF36a  347 PIIYAITHPKYRVAIAQHLPCLGVLLGVSRRHSRPYPSYRSTHRSTLTSH 396
               ||||||||||||| ||||||||||||||||.|| ||||||||||||:|
rSNORF36   344 PIIYAITHPKYRAAIAQHLPCLGVLLGVSGQRSHPSLSYRSTHRSTLSSQ 393
```

FIGURE 12B

```
hSNORF36a  397  TSNLSWISIRRRQESLGSESEVGWTHMEAAAVWGAAQQANGRSLYGQGLE  446
                . .| ||||||||||||||||||||  ||||||||||| ||||| .|.
rSNORF36   394  SSDLSWISGQKRQESLGSESEVGWTDTETTAAWGAAQQASGQSFCSHDLE  443 hSNORF36a  447  DLEAKAPPRPQGHEAETPGKTKGLIPSQDPRM                    478
                  |  ||    |  : ..:|| ||  |||||
rSNORF36   444  DGEVKAPSSPQEQKSKTP.KTKRHLPSLDRRM                    474
```

METHODS OF SCREENING FOR COMPOUNDS WHICH BIND TO A HUMAN SNORF36A RECEPTOR

This application is a continuation-in-part of U.S. Ser. No. 09/303,593, filed May 3, 1999, now abandoned the contents of which are hereby incorporated by reference into the subject application.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which the invention pertains.

Neuroregulators comprise a diverse group of natural products that subserve or modulate communication in the nervous system. They include, but are not limited to, neuropeptides, amino acids, biogenic amines, lipids and lipid metabolites, and other metabolic byproducts. Many of these neuroregulator substances interact with specific cell surface receptors which transduce signals from the outside to the inside of the cell. G-protein coupled receptors (GPCRs) represent a major class of cell surface receptors with which many neurotransmitters interact to mediate their effects. GPCRs are characterized by seven membrane-spanning domains and are coupled to their effectors via G-proteins linking receptor activation with intracellular biochemical sequelae such as stimulation of adenylyl cyclase.

Opsins represent one of the major families of GPCRs. These receptors are unique compared to other GPCRs In that light is a crucial co-factor for their activation under physiological conditions. A major subclass of the opsin family is that of visual opsins such as rhodopsin and cone opsins. The visual opsins, also known as visual photopigments, are located in the eye and are involved in transducing visual information from the eye to the brain. Our understanding of opsin function has been derived primarily from the study of visual photopigments.

Rhodopsin and cone opsins are localized in retinal rod and cone photoreceptors, respectively. These photopigments respond to different wavelengths of light and thus have very distinct absorption spectra associated with different absorption maxima ($\lambda_{max}$) Even though both receptor subtypes convey visual signals to the brain in response to illumination, they have evolved to perform very distinct functions related to vision. Cone opsins are primarily responsible for color vision, also known as photopic vision, in different species. In contrast, rhodopsin, believed to have evolved from cone opsin, is mainly involved in dim light vision, also known as scotopic vision. Rhodopsin, highly enriched in rod photoreceptor membranes, has been used extensively as a model receptor to understand activation mechanism and functioning of opsins.

Rhodopsin contains the seven membrane-spanning apoprotein opsin and a retinoid-based chromophore (See reviews Hargrave and McDowell, 1992; Yarfitz and Hurley, 1994). In the ground or inactive state (i.e. in the absence of light), the chromophore, usually 11-cis-retinal, is covalently attached to a highly conserved lysine residue in the middle of the seventh transmembrane segment via a protonated Schiff base. All vertebrate visual opsins contain a highly conserved glutamate residue in the transmembrane helix 3 which serves as a counterion for the protonated Schiff base. It has been postulated that 11-cis-retinal behaves as an inverse agonist and induces an inactive conformation of the apoprotein which, by itself, is partially active (Cohen et al., 1993; Surya et al., 1995). Upon absorbing a photon, 11-cis-retinal is isomerized to the agonist all-trans-retinal which introduces distortion in the opsin and initiates a cascade of conformational changes in the molecule. Rhodopsin is first converted to bathorhodopsin, followed by lumirhodopsin, metarhodopsin I and metarhodopsin II states in a sequential manner. Even though most of these transient conformational states are difficult to study biochemically, they can be easily distinguished on the basis of their spectroscopic properties since each state has a unique absorption maximum. Experimental evidence suggests that the formation of metarhodopsin II, a relatively stable state, involves deprotonation of the Schiff base and represents the active conformation of the apoprotein. In this state, the opsin activates the cognate G-prozein and initiates the intracellular signaling cascade which ultimately results in transfer of visual information to the brain. Upon hydrolysis of the Schiff base linkage, metarhodopsin II decays into free all-trans-retinal and opsin. All-trans-retinal is transported to the neighbouring retinal pigment epithelial cells where it is converted to 11-cis-retinal via enzymatic reactions. 11-cis-retinal is transported back to retinal photoreceptors where it recombines with the opsin apoprotein to regenerate the rhodopsin molecule.

Even though all visual opsins essentially use the same activation mechanism as rhodopsin, there are some noticeable differences between vertebrate and invertebrate visual opsins (Gartner and Towner, 1995; Yarfitz and Hurley, 1994, Terakita et al., 1998; Arnheiter, 1998). Activation of vertebrate visual pigment results primarily in stimulation of $G_t$ G-protein (also known as transducin) leading to an increase in cGMP phosphodiesterase activity. Initiation of this signaling cascade ultimately results in closure of cation channels and hyperpolarization of the cell. In contrast, opsin visual pigments in invertebrates such as squid and fruitfly activate $G_q$ G-protein and elevate intracellular $IP_3$ and $Ca^{2+}$ levels (Wood et al., 1989; Nobes et al., 1992; Yarfitz and Hurley, 1994). Another major difference between vertebrate and invertebrate visual opsins is the stability of the active conformation of the receotor. Formation of vertebrate metarhodopsin II, the active conformation of rhodopsin, is rapidly followed by hydrolysis of the Schiff base linkage and dissociation of metarhodopsin II into free all-trans-retinal and opsin apoprotein. It has been suggested that the glutamate counterion in the transmembrane helix 3 aids in the hydrolysis reaction (Gartner and Towner, 1995). In contrast, invertebrate metarhodopsin represents a thermally stable state where the chromophore remains attached to the apoprotein (Kiselev and Subramaniam, 1994). This allows rapid photoisomerization of all-trans-retinal back to 11-cis-retinal within the apoprotein and rapid regeneration of rhodopsin, thus eliminating the need for retinal regenerating tissue (Provencio et al., 1998). The thermally stable metastate of invertebrate photopigment may be formed due to the absence of the glutamate counterion in transmembrane helix 3 of invertebrate visual opsins (Gartner and Towner, 1995).

Most opsins use 11-cis-retinal derived from carotenoids as a chromophore; however, some opsins use 3-hydroxy, 4-hydroxy or 3,4-dehydro isomers of 11-cis-retinal as a chromophore to accommodate the abundant availability of the substituted carotenoids (Gartner and Towner, 1995). Different opsins respond to photons with different wavelengths, a phenomenon known as spectral tuning. Even though the use of a particular retinal derivative as a chromophore contributes to spectral specificity (Gartner and Towner, 1995), the major determinant of spectral tuning is the presence of unique amino acids surrounding the retinal-binding site (Kochendoerfer et al., 1999). For example, substitution of a highly conserved glycine in transmembrane helix 3 of rhodopsin with amino acids of increasing size results in progressive shift of $\lambda_{max}$ towards the blue wavelength (Han et al., 1996). Similarly, replacement of conserved non-polar residues with hydroxyl amino acids changes the opsin from a green-absorbing molecule to a red-absorbing pigment (Chan et al., 1992).

Even though the visual opsins have been at the forefront of opsin research, scientists are now turning their attention to non-visual opsins (the opsins not involved in transducing visual information) because of their potential involvement in physiological processes such as circadian rhythm and reproduction. The existence of non-visual photopigments in non-mammalian vertebrates was first suggested by Karl von Frisch. He demonstrated that the skin of the European minnow changed color in response to light even in the absence of the eye and pineal gland, and postulated photoreceptive elements in the diencephalon (Foster et al, 1994). Further evidence supporting the presence of non-visual photopigments was obtained in blinded lampreys and ducks which responded to illumination with body movements and gonadal induction, respectively (Foster et al., 1994). Recent studies using histochemical techniques has further corroborated these physiological observations. Silver et al. (1988) immunostained the cerebrospinal fluid (CSF)-contacting neurons with anti-opsin antibody in brains of the ring dove, quail and duck. Similarly, intense immunostaining of the CSF-contacting neurons within the basal brain of the lizard, Anolis carolinensis, was observed with anti-cone opsin antibody (Foster et al., 1993).

Recent molecular cloning of several non-visual opsins is in agreement with the above-mentioned studies. Pinopsin is expressed in the pineal gland of the chicken and is believed to play a role in circadian rhythm (Okano et al., 1994; Max et al., 1995). Interestingly, expression of the pinopsin gene is regulated by light (Takanaka et al., 1998). Max et al. (1998) have demonstrated light-dependent activation of transducin by pinopsin, implying that the pinopsin is a functional photoreceptor. Two other opsins identified in pinealocytes are vertebrate ancient (VA) opsin cloned from the salmon fish (Soni et al., 1997; Soni et al., 1998), and parapinopsin cloned from the channel catfish (Blackshaw and Snyder, 1997). In addition to pineal cells, VA opsin is also localized in the amacrine and horizontal cells of the salmon retina. On the other hand, expression of parapinopsin is confined to the parapineal and pineal organs of the catfish.

Several of the non-visual opsins are, in fact, expressed in the eye. Sun et al. (1997) cloned peropsin from human retina and mouse eye. This opsin is localized exclusively in microvilli of the apical membrane of retinal pigment epithelial (RPE) cells, indicating that it may function as a sensor of retinoids generated in the adjacent outer membrane of rhodopsin or cone opsins. RPE retinal G-protein-coupled receptor (RGR) is another receptor found in the RPE (Tao et al., 1998). Unlike other opsins which are believed to be present at the plasma membrane, RGR is localized intracellulariy. The amino acid sequence of RGR suggests that, along with squid retinochrome, it may form a distinct subfamily of opsins (Hara-Nishimura et al., 1990).

Interestingly, it has been suggested that RGR may prefer all-trans-retinal, rather than 11-cis-retinal, as a ligand and may be involved in the photoisomerization of the all-trans isomer to the 11-cis isomer (Hao and Fong, 1999). In such a case, its function may be the rapid regeneration of 11-cis-retinal in the RPE for use in the visual cycle.

One of the known photo-sensitive processes is melanosome dispersion in the dermal melanophores of Xenopus laevis. In accordance with this, melanopsin has been cloned from melanophores (Provencio et al., 1998). Melanopsin is expressed in the melanophores, suprachiasmatic and preoptic nuclei of the hypothalamus, iris, RPE and retina. Its expression in visual and nonvisual tissues suggests a role in visual and nonvisual photosensory phenomena. Recently, a non-visual opsin has been identified in the mammalian brain. Blackshaw and Snyder (1999) have cloned encephalopsin, which, as the name suggests, is highly expressed in various areas of the brain. It is present in the preoptic area and the paraventricular nucleus of the hypothalamus, the cerebral cortex, cerebellar Purkinje cells, striatum, thalamus and the ventral horn of the spinal cord. Interestingly, this receptor is not present in the eye.

The molecular identification of non-visual opsins has raised several questions. How are they activated? What is their physiological function? All the non-visual opsins cloned to date contain lysine in the seventh transmembrane helix, the site for retinal chromophore attachment, implying that a retinoid may be the chromophore for the non-visual opsins, similar to the visual opsins. Several groups have been successful in reconstituting non-visual opsins with retinoids and activating them with light (Okano et al., 1994; Soni et al., 1998). Retinoids can cross the blood-brain barrier, albeit at low efficiency (Pardridge et al., 1985; Franke et al., 1999). Furthermore, a transporter with high affinity for retinoids, β-Trace, has been recognized recently (Tanaka et al., 1997). This secretory protein is present in high levels in the CSF and may transport retinoids to different regions of the brain, analogous to the plasma RBP. That retinoids are indeed present in the brain was demonstrated by Foster et al. (1993) who were able to identify retinal isomers in the Anolis anterior brain using HPLC analysis. If a retinal isomer is indeed a chromophore for non-visual opsins then light would be needed to photoisomerize the isomer and activate the receptor. Several reports suggest that light can reach the deep areas of the brain (Muller and Wilson, 1986; Grace et al., 1996; Blackshaw and Snyder, 1999), and a neurotransmitter release-enhancing effect of light on cortical slices has been observed (Wade et al., 1988). Therefore, the activation mechanisms of non-visual opsins may be similar to the visual odsins. However, it should be noted here that some non-visual opsins have proven resistant to functional reconstitution with retinal isomers (Provencio et al., 1998; Blackshaw and Snyder, 1999), raising the possibility that these receptors utilize a non-retinoid ligand and may not require light for activation.

What could be the function of non-visual opsins? One interesting possibility is that they may be involved in circadian rhythm. Circadian rhythm represents daily fluctuations in biological activities that are regulated by the light-dark cycles. It is composed of three components: a photoactive input, the circadian clock itself which exhibits periodicity, and the behavioral and physiological oscillations as output. In animals, in the phenomenon known as photoentrainment, exposure to light results in regulation of the circadlan rhythm. However, the identity of the photoreceptive molecule mediating photoentrainment has remained a mystery. Since the photoentrainment response occurs at the wavelength of 500 nm, it has been suggested that an opsin may be mediating the response (Foster, 1998). Freedman et al. (1999) and Lucas et al. (1999) recently demonstrated that photoentrainment was intact in mice lacking rod and cone receptors; however, removal of the eyes in these mice abolished the effect of light on circadian rhythm as well as on melatonin synthesis. These results, and ocular localization of several non-visual opsins, strongly support the role of ocular non-visual opsins in photoentraining circadian rhythm. In addition, the non-visual opsins localized in the CNS may form a component of the circadian clock itself.

If non-visual opsins are indeed involved in regulating circadian rhythm, then they represent an attractive therapeutic target for circadian rhythm-related conditions. These include sleep disorders such as Jet lag. It has been suggested that a change in circadian rhythm may be an underlying cause for sleep disorders such as insomnia, Advanced Sleep Phase Syndrome and Delayed Sleep Phase Syndrome (Sedgwick, 1998; Refinetti, 1999). In addition, dissociation between biological clock and work hours may result in shift-work-related sleep disorders. Importantly, bright light therapy has been demonstrated to help in these disorders (Rosenthal et al., 1990; Lack and Wright, 1993; Campbell et al., 1995; Murphy and Campbell, 1996; Cooke et al., 1998; Refinetti, 1999). Similarly, exposure to light at appropriate time reduces the effect of jet lag on travelers (Refinetti, 1999). These observations suggest that non-visual opsins may mediate these beneficial effects of light in circadian rhythm-related disorders.

Non-visual opsins also may play a role in seasonal affective disorder (SAD). This disorder is characterized by a subpopulation of people suffering from depression during winter. Light therapy is effective in these people (Terman and Terman, 1999); especially green light is more effective than red light (Oren et al., 1991). It has been recently hypothesized that the interaction of specialized photoreceptors with magnetic field may influence sensitivity of patients suffering from SAD to light (Partonen, 1998).

In addition, the discreet localization of various opsins in the CNS areas indicate their potential role in CNS-related physiology and disorders.

Non-visual photoreceptors are also involved in melanosome dispersion in melanophores, and thus, in change in the color of the skin in various species. In birds and mammals, non-visual 'deep brain photoreceptors' are also linked to reproductive behaviour and photoperiodic gonadal responses (Yoshikawa and Oishi, 1998).

In summary, opsins constitute an important branch of the GPCR superfamily. They behave as photosensitive elements. They are localized in the retina and in non-retinal locations including the brain. The retinal rod and cone opsins are mainly responsible for conveying visual information to the brain, while the non-visual oprsins in the retina and elsewhere may be involved in regulation of melatonin synthesis and circadian rhythm, photoentrainment, SAD, skin colour change and camouflage, and reproductive behavior.

SUMMARY OF THE INVENTION

This invention provides an isolated nucleic acid encoding a mammalian SNORF36 receptor.

This invention further provides a purified mammalian SNORF36 receptor protein.

This invention also provides a vector comprising a nucleic acid in accordance with this invention.

This invention still further provides a cell comprising a vector in accordance with this invention.

This invention additionally provides a membrane preparation isolated from a cell in accordance with this invention.

Furthermore, this invention provides a nucleic acid probe comprising at least 15 nucleotides, which probe specifically hybridizes with a nucleic acid encoding a mammalian SNORF36 receptor, wherein the probe has a sequence complementary to a unique sequence present within one of the two strands of the nucleic acid encoding the mammalian SNORF36 receptor contained in plasmid pcDNA3.1-hSNORF36a-f (ATCC® Accession No. 203977), plasmid pcDNA3.1-hSNORF36b-f (ATCC® Accession No. 203976), plasmid pEXJ.T3T7-rSNORF36p (ATCC® Patent Depository No. PTA-534) or plasmid pEXJ.T7-rSNORF36-f (ATCC® Patent Depository No. PTA-1216).

This invention further provides a nucleic acid probe comprising at least 15 nucleotides, which probe specifically hybridizes with a nucleic acid encoding a mammalian SNORF36 receptor, wherein the probe has a sequence complementary to a unique sequence present within (a) the nucleic acid sequence shown in FIGS. 1A–1C (SEQ ID NO: 1), (b) the reverse complement thereof.

This invention further provides a nucleic acid probe comprising at least 15 nucleotides, which probe specifically hybridizes with a nucleic acid encoding a mammalian SNORF36 receptor, wherein the probe has a sequence complementary to a unique sequence present within (a) the nucleic acid sequence shown in FIGS. 3A–3C (SEQ ID NO: 3), (b) the reverse complement thereof.

This invention provides an antisense oligonucleotide having a sequence capable of specifically hybridizing to RNA encoding a mammalian SNORF36 receptor, so as to prevent translation of such RNA.

This invention further provides an antisense oligonucleotide having a sequence capable of specifically hybridizing to genomic DNA encoding a mammalian SNORF36 receptor, so as to prevent transcription of such genomic DNA.

This invention also provides an antibody capable of binding to a mammalian SNORF36 receptor encoded by a nucleic acid in accordance with this invention.

Moreover, this invention provides an agent capable of competitively inhibiting the binding of an antibody in accordance with this invention to a mammalian SNORF36 receptor.

This invention yet further provides a pharmaceutical composition comprising (a) an amount of an oligonucleotide in accordance with this invention capable of passing through a cell membrane and effective to reduce expression of a mammalian SNORF36 receptor and (b) a pharmaceutically acceptable carrier capable of passing through the cell membrane.

This invention also provides a pharmaceutical composition which comprises an amount of an antibody in accordance with this invention effective to block binding of a ligand to a human SNORF36 receptor and a pharmaceutically acceptable carrier.

This invention further provides a transgenic, nonhuman mammal expressing DNA encoding a mammalian SNORF36 receptor in accordance with this invention.

This invention still further provides a transgenic, nonhuman mammal comprising a homologous recombination knockout of a native mammalian SNORF36 receptor.

This invention further provides a transgenic, nonhuman mammal whose genome comprises antisense DNA complementary to DNA encoding a mammalian SNORF36 receptor in accordance with this invention so placed within such genome as to be transcribed into antisense mRNA which is complementary to and hybridizes with mRNA encoding the mammalian SNORF36 receptor so as to reduce translation of such mRNA and expression of such receptor.

This invention provides a process for identifying a chemical compound which specifically binds to a mammalian SNORF36 receptor which comprises contacting cells containing DNA encoding, and expressing on their cell surface, the mammalian SNORF36 receptor, wherein such cells do not normally express the mammalian SNORF36 receptor, with the compound under conditions suitable for binding, and detecting specific binding of the chemical compound to the mammalian SNORF36 receptor.

This invention further provides a process for identifying a chemical compound which specifically binds to a mammalian SNORF36 receptor which comprises contacting a membrane preparation from cells containing DNA encoding, and expressing on their cell surface, the mammalian SNORF36 receptor, wherein such cells do not normally express the mammalian SNORF36 receptor, with the compound under conditions suitable for binding, and detecting specific binding of the chemical compound to the mammalian SNORF36 receptor.

This invention still further provides a process involving competitive binding for identifying a chemical compound which specifically binds to a mammalian SNORF36 receptor which comprises separately contacting cells expressing on their cell surface the mammalian SNORF36 receptor, wherein such cells do not normally express the mammalian SNORF36 receptor, with both the chemical compound and a second chemical compound known to bind to the receptor, and with only the second chemical compound, under conditions suitable for binding of such compounds to the receptor, and detecting specific binding of the chemical compound to the mammalian SNORF36 receptor, a decrease in the binding of the second chemical compound to the mammalian SNORF36 receptor in the presence of the chemical compound being tested indicating that such chemical compound binds to the mammalian SNORF36 receptor.

This invention further provides a process involving competitive binding for identifying a chemical compound which specifically binds to a mammalian SNORF36 receptor which comprises separately contacting a membrane preparation from cells expressing on their cell surface the mammalian SNORF36 receptor, wherein such cells do not normally express the mammalian SNORF36 receptor, with both the chemical compound and a second chemical compound known to bind to the receptor, and with only the second chemical compound, under conditions suitable for binding of such compounds to the receptor, and detecting specific binding of the chemical compound to the mammalian SNORF36 receptor, a decrease in the binding of the second chemical compound to the mammalian SNORF36 receptor in the presence of the chemical compound being tested indicating that such chemical compound binds to the mammalian SNORF36 receptor.

This invention further provides a compound identified by one of the processes of this invention.

This invention provides a method of screening a plurality of chemical compounds not known to bind to a mammalian SNORF36 receptor to identify a compound which specifically binds to the mammalian SNORF36 receptor, which comprises (a)contactina cells transfected with, and expressing, DNA encoding the mammalian SNORF36 receptor with a compound known to bind specifically to the mammalian SNORF36 receptor; (b)contacting the cells of step (a) with the plurality of compounds not known to bind specifically to the mammalian SNORF36 receptor, under conditions permitting binding of compounds known to bind to the mammalian SNORF36 receptor; (c) determining whether the binding of the compound known to bind to the mammalian SNORF36 receptor is reduced in the presence of the plurality of compounds, relative to the binding of the compound in the absence of the plurality of compounds; and if so (d) separately determining the binding to the mammalian SNORF36 receptor of each compound included in the plurality of compounds, so as to thereby identify any compound included therein which specifically binds to the mammalian SNORF36 receptor.

This invention further provides a method of screening a plurality of chemical compounds not known to bind to a mammalian SNORF36 receptor to identify a compound which specifically binds to the mammalian SNORF36 receptor, which comprises (a) contacting a membrane preparation from cells transfected with, and expressing, DNA encoding the mammalian SNORF36 receptor with the plurality of compounds not known to bind specifically to the mammalian SNORF36 receptor under conditions permitting binding of compounds known to bind to the mammalian SNORF36 receptor; (b) determining whether the binding of a compound known to bind to the mammalian SNORF36 receptor is reduced in the presence of the plurality of compounds, relative to the binding of the compound in the absence of the plurality of compounds; and if so (c) separately determining the binding to the mammalian SNORF36 receptor of each compound included in the plurality of compounds, so as to thereby identify any compound included therein which specifically binds to the mammalian SNORF36 receptor.

This invention also provides a method of detecting expression of a mammalian SNORF36 receptor by detecting the presence of mRNA coding for the mammalian SNORF36 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF36 receptor by the cell.

This invention further provides a method of detecting the presence of a mammalian SNORF36 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF36 receptor on the surface of the cell.

This invention still further provides a method of determining the physiological effects of varying levels of activity of mammalian SNORF36 receptors which comprises producing a transgenic, nonhuman mammal in accordance with this invention whose levels of mammalian SNORF36 receptor activity are varied by use of an inducible promoter which regulates mammalian SNORF36 receptor expression.

This invention additionally provides a method of determining the physiological effects of varying levels of activity of mammalian SNORF36 receptors which comprises producing a panel of transgenic, nonhuman mammals in accordance with this invention each expressing a different amount of mammalian SNORF36 receptor.

Moreover, this invention provides a method for identifying an antagonist capable of alleviating an abnormality wherein the abnormality is alleviated by decreasing the activity of a mammalian SNORF36 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF36 receptor, the alleviation of such an abnormality identifying the compound as an antagonist.

This invention also provides an antagonist identified by the preceding method.

This invention further provides a composition, e.g. a pharmaceutical composition, comprising an antagonist according to this invention and a carrier, e.g. a pharmaceutically acceptable carrier.

This invention additionally provides a method of treating an abnormality in a subject wherein the abnormality is alleviated by decreasing the activity of a mammalian SNORF36 receptor which comprises administering to the subject an effective amount of the pharmaceutical composition according to this invention so as to thereby treat the abnormality.

In addition, this invention provides a method for identifying an agonist capable of alleviating an abnormality in a subject wherein the abnormality is alleviated by increasing the activity of a mammalian SNORF36 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist.

This invention further provides an agonist identified by the preceding method.

This invention still further provides a composition, e.g. a pharmaceutical composition, comprising an agonist according to this invention and a carrier, e.g. a pharmaceutically acceptable carrier.

Moreover, this invention provides a method of treating an abnormality in a subject wherein the abnormality is alleviated by increasing the activity of a mammalian SNORF36 receptor which comprises administering to the subject an effective amount of the pharmaceutical composition according to this invention so as to thereby treat the abnormality.

Yet further, this invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF36 receptor and labeled with a detectable marker; (e) detecting labeled bands which have hybridized to the DNA encoding a mammalian SNORF36 receptor to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

This invention also provides a method of preparing a purified mammalian SNORF36 receptor according to the invention which comprises: (a) culturing cells which express the mammalian SNORF36 receptor; (b) recovering the mammalian SNORF36 receptor from the cells; and (c) purifying the mammalian SNORF36 receptor so recovered.

This invention further provides a method of preparing the purified mammalian SNORF36 receptor according to the invention which comprises: (a) inserting a nucleic acid encoding the mammalian SNORF36 receptor into a suitable expression vector; (b) introducing the resulting vector into a suitable host cell; (c) placing the resulting host cell in suitable conditions permitting the production of the mammalian SNORF36 receptor; (d) recovering the mammalian SNORF36 receptor so produced; and optionally (e) isolating and/or purifying the mammalian SNORF36 receptor so recovered.

Furthermore, this invention provides a process for determining whether a chemical compound is a mammalian SNORF36 receptor agonist which comprises contacting cells transfected with and expressing DNA encodinr the mammalian SNORF36 receptor with the compound under conditions permitting the activation of the mammalian SNORF36 receptor, and detecting any increase in mammalian SNORF36 receptor activity, so as to thereby determine whether the compound is a mammalian SNORF36 receptor agonist.

This invention also provides a process for determining whether a chemical compound is a mammalian SNORF36 receptor antagonist which comprises contacting cells transfected with and expressing DNA encoding the mammalian SNORF36 receptor with the compound in the presence of a known mammalian SNORF36 receptor agonist, under conditions permitting the activation of the mammalian SNORF36 receptor, and detecting any decrease in mammalian SNORF36 receptor activity, so as to thereby determine whether the compound is a mammalian SNORF36 receptor antagonist.

This invention still further provides a composition, for example a pharmaceutical composition, which comprises an amount of a mammalian SNORF36 receptor agonist determined by a process according to this invention effective to increase activity of a mammalian SNORF36 receptor and a carrier, for example, a pharmaceutically acceptable carrier. In one embodiment, the mammalian SNORF36 receptor agonist is not previously known.

Also, this invention provides a composition, for example a pharmaceutical composition, which comprises an amount of a mammalian SNORF36 receptor antagonist determined by a process according to this invention effective to reduce activity of a mammalian SNORF36 receptor and a carrier, for example, a pharmaceutically acceptable carrier.

This invention moreover provides a process for determining whether a chemical compound specifically binds to and activates a mammalian SNORF36 receptor, which comprises contacting cells producing a second messenger response and expressing on their cell surface the mammalian SNORF36 receptor, wherein such cells do not normally express the mammalian SNORF36 receptor, with the chemical compound under conditions suitable for activation of the mammalian SNORF36 receptor, and measuring the second messenger response in the presence and in the absence of the chemical compound, a change, e.g. an increase, in the second messenger response in the presence of the chemical compound indicating that the compound activates the mammalian SNORF36 receptor.

This invention still further provides a process for determining whether a chemical compound specifically binds to and inhibits activation of a mammalian SNORF36 receptor, which comprises separately contacting cells producing a second messenger response and expressing on their cell surface the mammalian SNORF36 receptor, wherein such cells do not normally express the mammalian SNORF36 receptor, with both the chemical compound and a second chemical compound known to activate the mammalian SNORF36 receptor, and with only the second chemical compound, under conditions suitable for activation of the mammalian SNORF36 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian SNORF36 receptor.

Further, this invention provides a compound determined by a process according to the invention and a composition, for example, a pharmaceutical composition, which comprises an amount of a mammalian SNORF36 receptor agonist determined to be such by a process according to the invention, effective to increase activity of the mammalian SNORF36 receptor and a carrier, for example, a pharmaceutically acceptable carrier.

This invention also provides a composition, for example, a pharmaceutical composition, which comprises an amount of a mammalian SNORF36 receptor antagonist determined to be such by a process according to the invention, effective to reduce activity of the mammalian SNORF36 receptor and a carrier, for example, a pharmaceutically acceptable carrier.

This invention yet further provides a method of screening a plurality of chemical compounds not known to activate a mammalian SNORF36 receptor to identify a compound which activates the mammalian SNORF36 receptor which comprises: (a) contacting cells transfected with and expressing the mammalian SNORF36 receptor with the plurality of compounds not known to activate the mammalian SNORF36 receptor, under conditions permitting activation of the mammalian SNORF36 receptor; (b) determining whether the activity of the mammalian SNORF36 receptor is increased in the presence of one or more of the compounds; and if so (c) separately determining whether the activation of the mammalian SNORF36 receptor is increased by any compound included in the plurality of compounds, so as to thereby identify each compound which activates the mammalian SNORF36 receptor.

This invention provides a method of screening a plurality of chemical compounds not known to inhibit the activation of a mammalian SNORF36 receptor to identify a compound which inhibits the activation of the mammalian SNORF36 receptor, which comprises: (a) contacting cells transfected with and expressing the mammalian SNORF36 receptor with the plurality of compounds in the presence of a known mammalian SNORF36 receptor agonist, under conditions permitting activation of the mammalian SNORF36 receptor; (b) determining whether the extent or amount of activation of the mammalian SNORF36 receptor is reduced in the presence of one or more of the compounds, relative to the extent or amount of activation of the mammalian SNORF36 receptor in the absence of such one or more compounds; and if so (c) separately determining whether each such compound inhibits activation of the mammalian SNORF36 receptor for each compound included in the plurality of compounds, so as to thereby identify any compound included in such plurality of compounds which inhibits the activation of the mammalian SNORF36 receptor.

This invention also provides a composition, for example a pharmaceutical composition, comprising a compound identified by a method according to this invention in an amount effective to increase mammalian SNORF36 receptor activity and a carrier, for example, a pharmaceutically acceptable carrier.

This invention still further provides a composition, for example a pharmaceutical composition, comprising a compound identified by a method according to this invention in an amount effective to decrease mammalian SNORF36 receptor activity and a carrier, for example a pharmaceutically acceptable carrier.

Furthermore, this invention provides a method of treating an abnormality in a subject wherein the abnormality is alleviated by increasing the activity of a mammalian SNORF36 receptor which comprises administering to the subject a compound which is a mammalian SNORF36 receptor agonist in an amount effective to treat the abnormality.

This invention additionally provides a method of treating an abnormality in a subject wherein the abnormality is alleviated by decreasing the activity of a mammalian SNORF36 receptor which comprises administering to the subject a compound which is a mammalian SNORF36 receptor antagonist in an amount effective to treat the abnormality.

This invention also provides a process for making a composition of matter which specifically binds to a mammalian SNORF36 receptor which comprises identifying a chemical compound using a process in accordance with this invention and then synthesizing the chemical compound or a novel structural and functional analog or homolog thereof.

This invention further provides a process for preparing a composition, for example, a pharmaceutical composition which comprises admixing a carrier, for example, a pharmaceutically acceptable carrier, and a pharmaceutically effective amount of a chemical compound identified by a process of in accordance with this invention or a novel structural and functional analog or homolog thereof.

BRIEF DESCRIPTION OF THE FIGURES

FIGS. 1A–1C

Nucleotide sequence including sequence encoding a human SNORF36a receptor (SEQ ID NO: 1). Putative open reading frames including the shortest open reading frame are indicated by underlining two start (ATG) codons (at positions 10–12 and 67–69) and the stop codon (at positions 1444–1446). In addition, partial 5' and 3' untranslated sequences are shown.

FIGS. 2A–2B

Deduced amino acid sequence (SEQ ID NO: 2) of the human SNORF36a receptor encoded by the longest open reading frame indicated in the nucleotide sequence shown in FIGS. 1A–1C (SEQ ID NO: 1). The seven putative transmembrane (TM) regions are underlined.

FIGS. 3A–3C

Nucleotide sequence including sequence encoding a human SNORF36b receptor (SEQ ID NO: 3). Putative open reading frames including the shortest open reading frame are indicated by underlining two start (ATG) codons (at positions 10–12 and 67–69) and the stop codon (at positions 1477–1479). In addition, partial 5' and 3' untranslated sequences are shown.

FIGS. 4A–4C

Deduced amino acid sequence (SEQ ID NO: 4) of the human SNORF36b receptor encoded by the longest open reading frame indicated in the nucleotide sequence shown in FIGS. 3A–3C (SEQ ID NO: 3). The seven putative transmembrane (TM) regions are underlined.

FIG. 5

Nucleotide sequence including part of the sequence encoding a rat SNORF36 receptor (SEQ ID NO: 5).

FIG. 6

Deduced partial amino acid sequence (SEQ ID NO: 6) of the rat SNORF36 receptor encoded by the nucleotide sequence shown in FIG. 5 (SEQ ID NO: 5). Putative transmembrane (TM) regions are underlined.

FIGS. 7A–7B

Nucleotide alignment of partial sequences of human SNORF36 and rat SNORF36. Vertical lines represent identical residues.

FIG. 8

Amino acid alignment of partial sequences of human SNORF36 and rat SNORF36. Vertical lines represent identical residues and dots represent similar residues.

FIGS. 9A–9C

Nucleotide sequence including sequence encoding a rat SNORF36 receptor (SEQ ID NO: 7). Putative open reading frames including the shortest open reading frame are indicated by underlining one start (ATG) codon (at positions 25–27) and the stop codon (at positions 1447–1449). In addition, partial 5' and 3' untranslated sequences are shown.

FIGS. 10A–10C

Deduced amino acid sequence (SEQ ID NO: 8) of the rat SNORF36 receptor encoded by the longest open reading frame indicated in the nucleotide sequence shown in FIGS. 9A–9C (SEQ ID NO: 7). The seven putative transmembrane (TM) regions are underlined.

FIGS. 11A–11D

Nucleotide alignment of human and rat SNORF36 receptors. Vertical lines indicate conserved residues, dots represent gaps in the alignment.

FIGS. 12A–12B

Amino acid alignment of human and rat SNORF36 receptors. Vertical lines indicate conserved residues, dots represent gaps in the alignment.

Figure 13A:
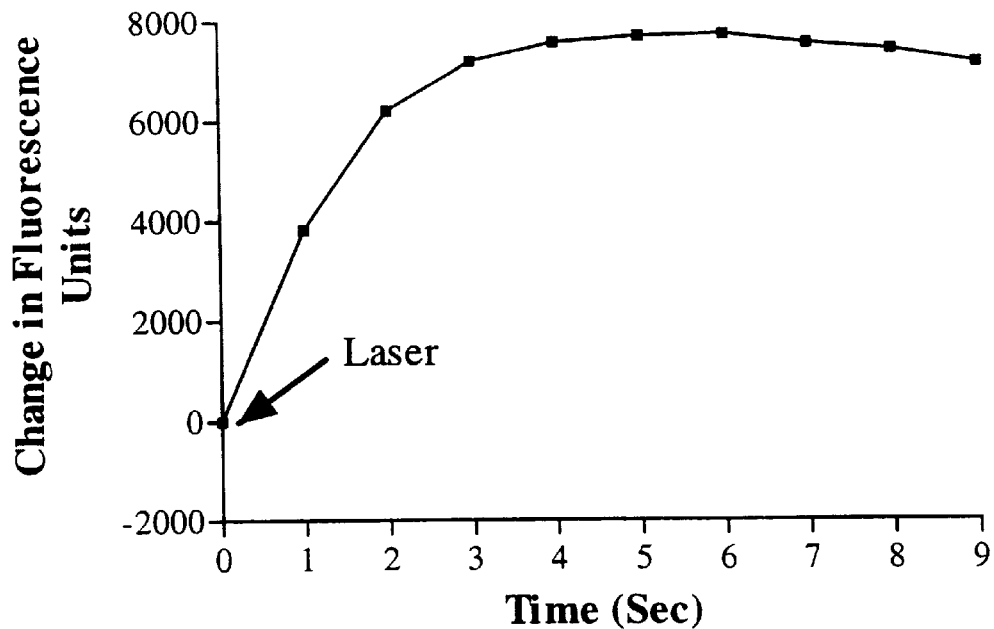
Figure 13B:
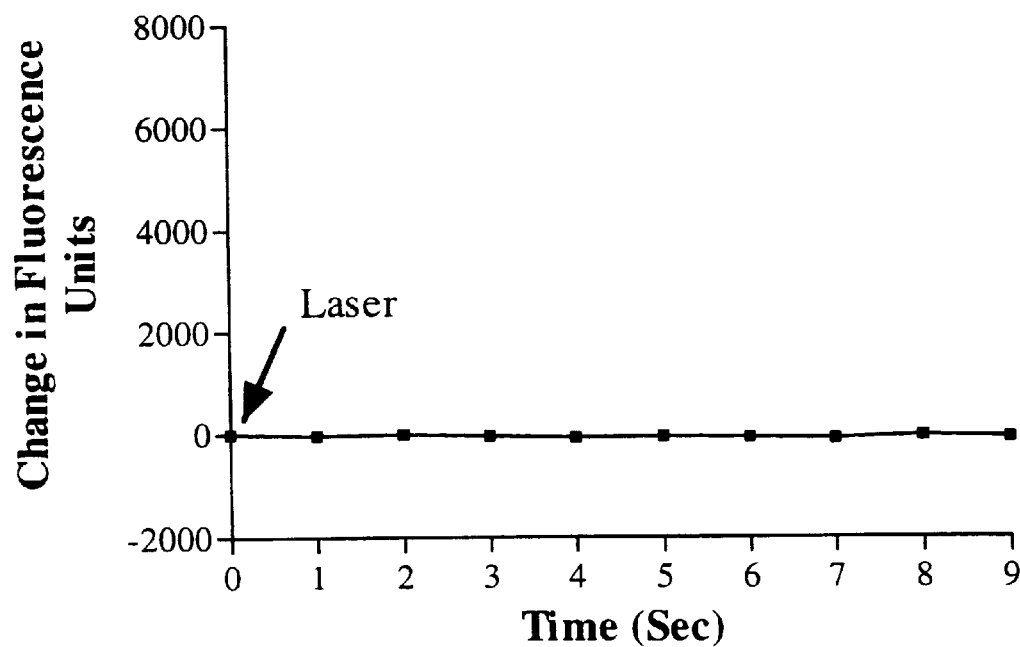

FIGS. 13A and 13B

Baseline $Ca^{2+}$ mobilization response in human SNORF36a-transfected Cos-7 cells which were either, (1) not exposed to lamp light (FIG. 13A), or (2) exposed to lamp light for 90 minutes before the experiment (FIG. 13B). The response was measured using Fluorometric Imaging Plate Reader (FLIPR™). Cells were exposed to laser light at 1 second interval beginning at time 0 until the end of the trace. The first fluorescence value was subtracted from all the fluorescence values. No drug was added during the duration of the trace.

Figure 14A:
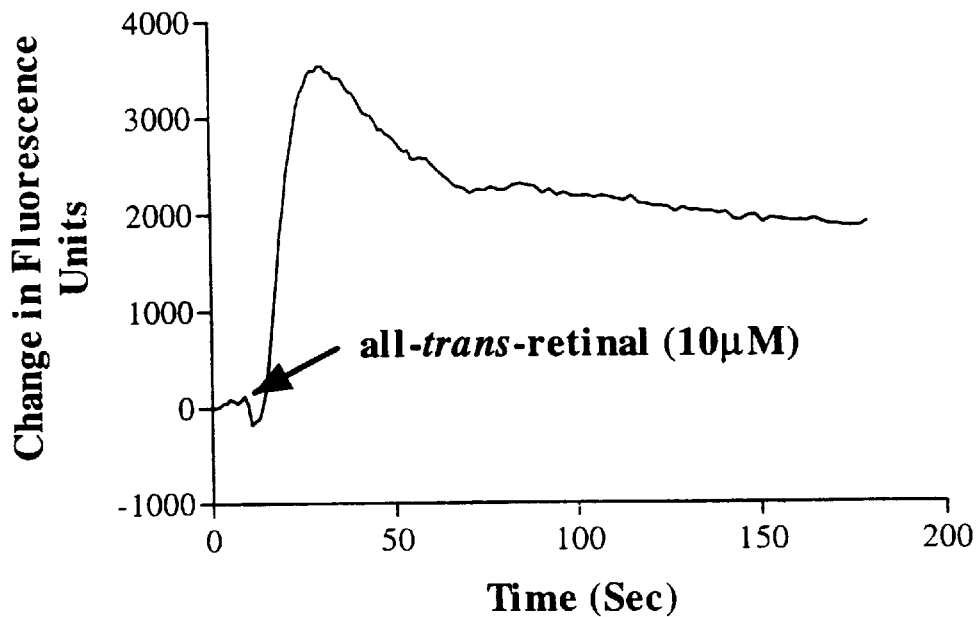
Figure 14B:
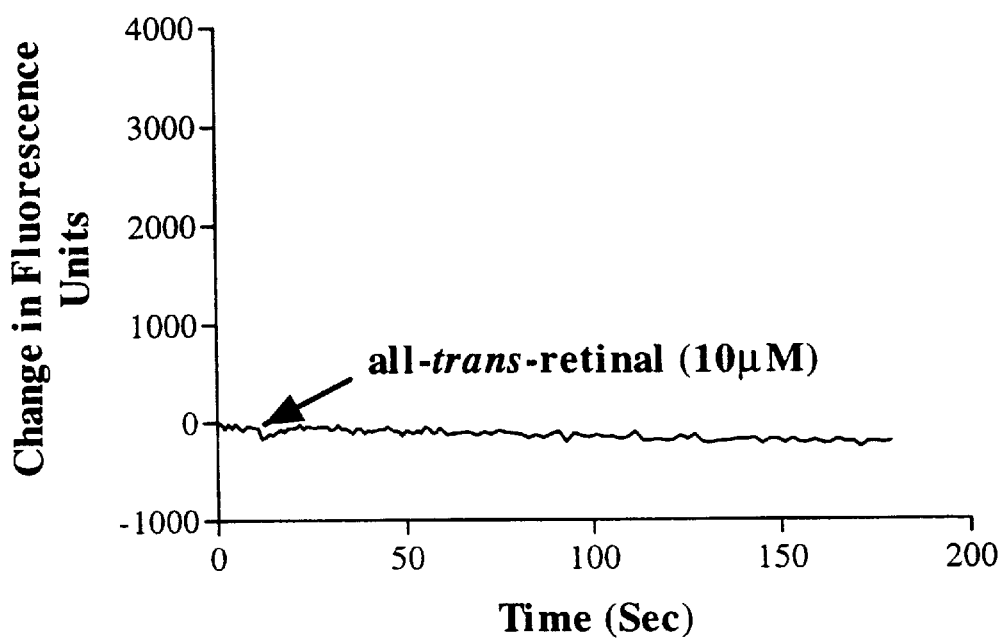

FIGS. 14A and 14B

Representative traces demonstrating the effect of all-trans-retinal (10 μM) on intracellular $Ca^{2+}$ in (1) human SNORF36a-transfected (FIG. 14A), and (2) empty vector-transfected Cos-7 cells (FIG. 14B). The response was measured using Fluorometric Imaging Plate Reader (FLIPR™). All-trans-retinal was added at time indicated by the arrow. Baseline subtraction and negative control corrections were performed on the traces.

Figure 15A:
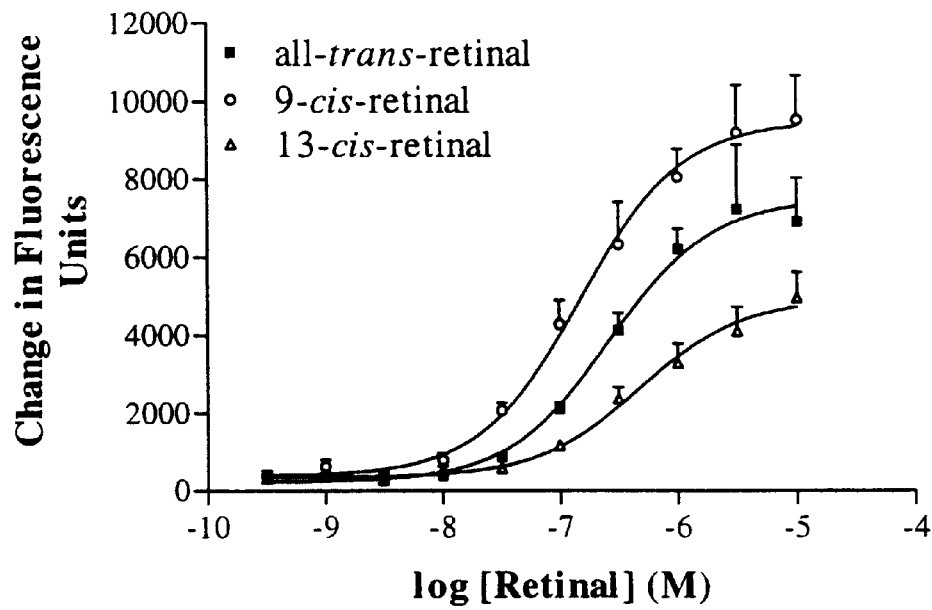
Figure 15B:
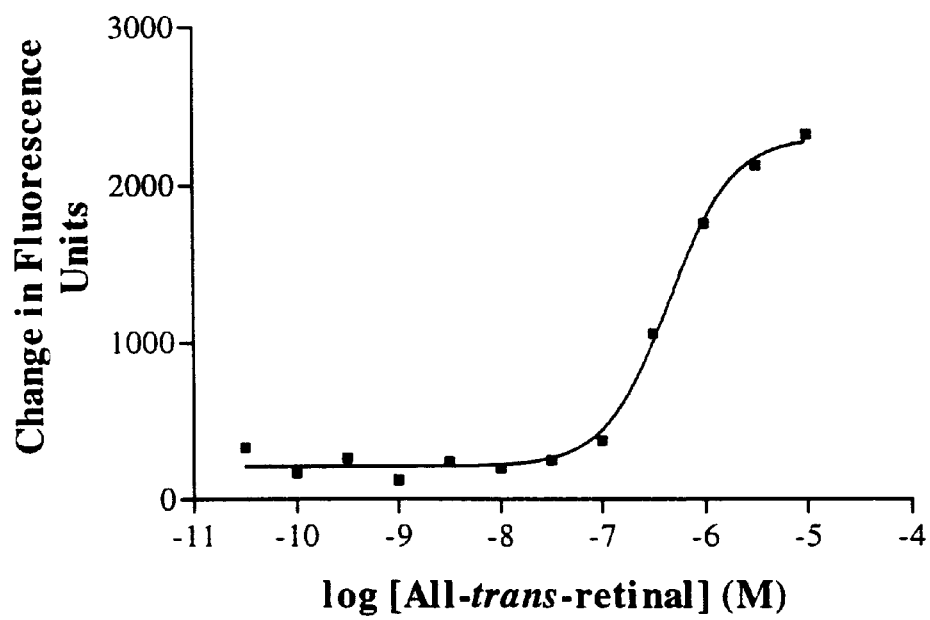

FIGS. 15A and 15B

Concentration-dependent effect of retinal analogues on intracellular $Ca^{2+}$ in human SNORF36a-transfected (1) Cos-7 cells (n=3) (FIG. 15A), and (2) HEK293 cells (n=1) (FIG. 15B). Data are presented as mean±SD.

Figure 16A:
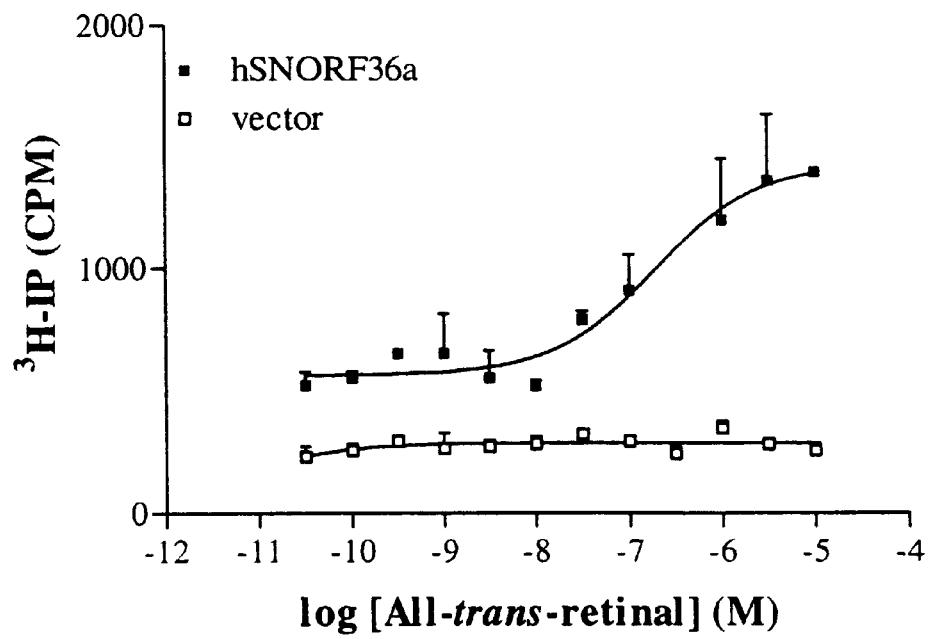
Figure 16B:
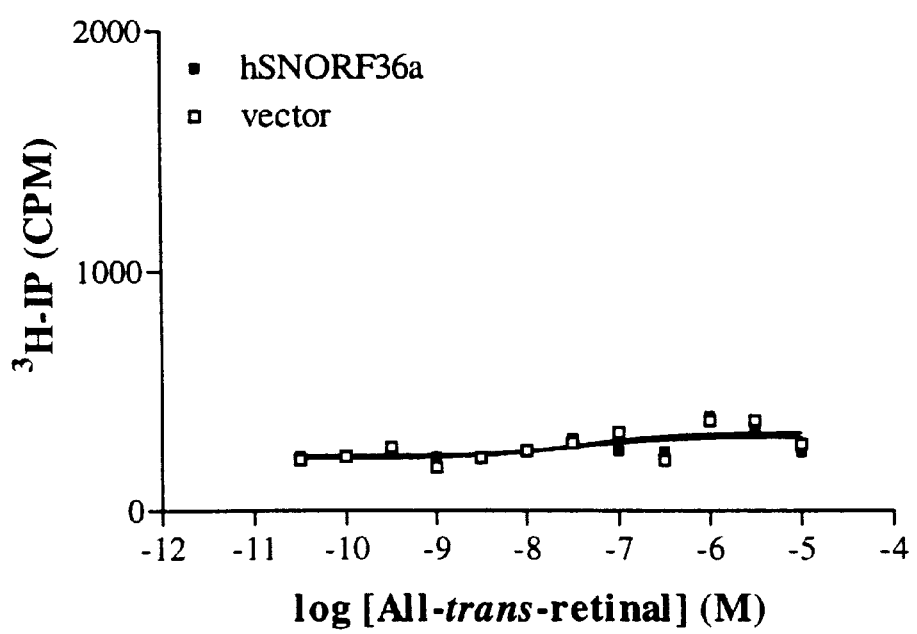

FIGS. 16A and 16B

Concentration-dependent effect of all-trans-retinal on phosphoinositide hydrolysis in human SNORF36a- and empty vector-transfected Cos-7 cells either (1) exposed to lamp light (n=2) (FIG. 16A), or (2) not exposed to lamp light (n=1) (FIG. 16B). Data are presented as mean±SD.

Figure 17A:
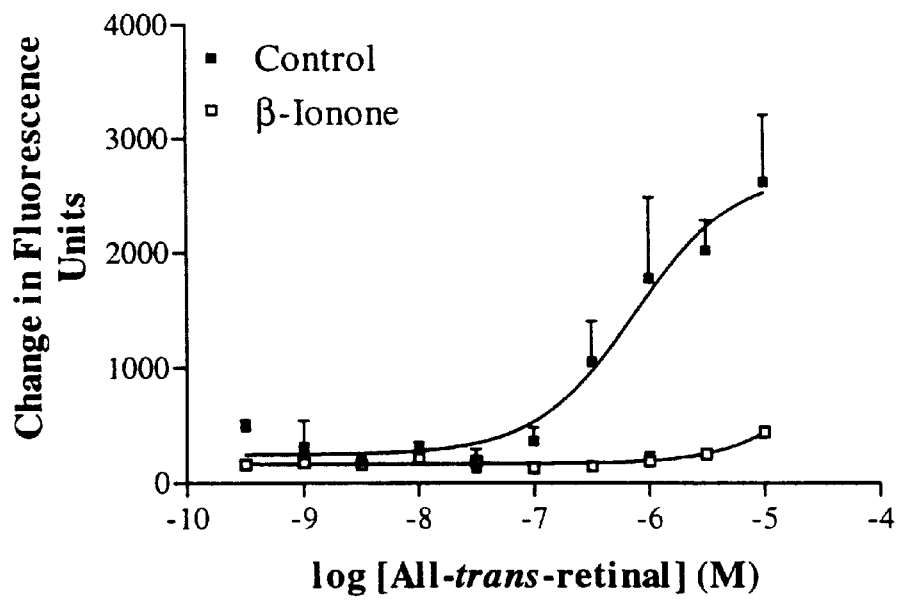
Figure 17B:
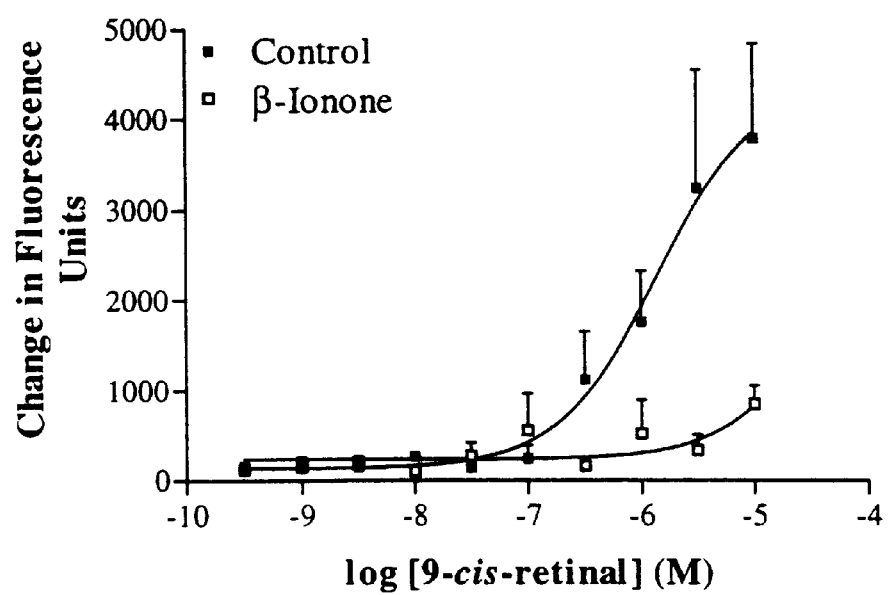

FIGS. 17A and 17B

Antagonism by β-ionone (10 μM) of all-trans-retinal-induced intracellular $Ca^{2+}$ mobilization in human SNORF36a-transfected Cos-7 cells (n=2) (FIG. 17A) Antagonism by β-ionone (10 μM) of 9-cis-retinal-induced intracellular $Ca^{2+}$ mobilization in human SNORF36a-transfected Cos-7 cells (n=2)(FIG. 17B). The response was measured using Fluorometric Imaging Plate Reader (FLIPR™). Data are presented as mean ±SD.

FIGS. 18A–18C

Light sensitivity of SNORF36a expressed in oocytes. Oocytes shown in FIG. 18A and FIG. 18B were injected with 10 ng SNORF36a synthetic mRNA. The current is expressed in nA (nanoampere) while time is expressed in s (second).

FIG. 18A

Current elicited by light exposure (bar) in a voltage-clamped oocyte expressing SNORF36a. The oocyte was pre-incubated with all-trans-retinal (100 nM) in the dark for 24 hours.

FIG. 18B

Response of a second oocyte pre-incubated with all-trans-retinal that had been previously exposed to room light.

FIG. 18C

Control uninjected oocyte, pre-incubated with all-trans-retinal (100 nM) for 24 h, fails to respond to light.

FIG. 19

Summary of light sensitivity of oocytes expressing SNORF36 pre-incubated with all-trans-retinal, 13-cis-retinal and ATRA (all-trans retinoic acid). Numbers in parentheses are the numbers of oocytes used.

DETAILED DESCRIPTION OF THE INVENTION

This invention provides a recombinant nucleic acid comprising a nucleic acid encoding a mammalian SNORF36a receptor, wherein the mammalian receptor-encoding nucleic acid hybridizes under high stringency conditions to a nucleic acid encoding a human SNORF36a receptor and having a sequence identical to the sequence of the human SNORF36a receptor-encoding nucleic acid contained in plasmid pcDNA3.1-hSNORF36a-f (ATCC® Patent Depository No. 203977).

This invention further provides a recombinant nucleic acid comprising a nucleic acid encoding a human SNORF36a receptor, wherein the human SNORF36a receptor comprises an amino acid sequence identical to the sequence of the human SNORF36a receptor encoded by the shortest open reading frame indicated in FIGS. 1A–1C (SEQ ID NO: 1).

This invention provides a recombinant nucleic acid comprising a nucleic acid encoding a mammalian SNORF36b receptor, wherein the mammalian receptor-encoding nucleic acid hybridizes under high stringency conditions to a nucleic acid encoding a human SNORF36b receptor and having a sequence identical to the sequence of the human SNORF36b receptor-encoding nucleic acid contained in plasmid pcDNA3.1-hSNORF36b-f (ATCC® Patent Depository No. 203976).

This invention also provides a recombinant nucleic acid comprising a nucleic acid encoding a human SNORF36b receptor, wherein the human SNORF36b receptor comprises an amino acid sequence identical to the sequence of the human SNORF36b receptor encoded by the shortest open reading frame indicated in FIGS. 3A–3C (SEQ ID NO: 3).

This invention also contemplates recombinant nucleic acids which comprise nucleic acids encoding naturally occurring allelic variants of the above. For example, one such allelic variant involves changing Guanine (G) to Adenine (A) at position 39 in FIGS. 1A–1C (SEQ ID NO: 1). Another example of such an allelic variant involves changing Guanine (G) to Adenine (A) at position 39 in FIGS. 3A–3C (SEQ ID NO: 3).

The plasmid pcDNA3.1-hSNORF36a-f and plasmid pcDNA3.1-hSNORF36b-f were both deposited on Apr. 28, 1999, with the American Type Culture Collection (ATCC®), 10801 University Blvd., Manassas, Va. 20110–2209, U.S.A. under the provisions of the Budapest Treaty for the International Recognition of the Deposit of Microorganisms for the Purposes of Patent Procedure and were accorded ATCC® Patent Depository Nos. 203977 and 203976, respectively.

The plasmid pEXJ.T3T7-rSNORF36p was deposited on Aug. 17, 1999, with the American Type Culture Collection (ATCC®), 10801 University Blvd., Manassas, Va. 20110–2209, U.S.A. under the provisions of the Budapest Treaty for the International Recognition of the Deposit of Microorganisms for the Purposes of Patent Procedure and were accorded ATCC® Patent Depository No. PTA-534.

The plasmid pEXJ.T7-rSNORF36-f was deposited on Jan. 18, 2000, with the American Type Culture Collection (ATCC®), 10801 University Blvd., Manassas, Va. 20110–2209, U.S.A. under the provisions of the Budapest Treaty for the International Recognition of the Deposit of Microorganisms for the Purposes of Patent Procedure and were accorded ATCC® Patent Depository No. PTA-1216.

Hybridization methods are well known to those of skill in the art. For purposes of this invention, hybridization under high stringency conditions means hybridization performed at 40° C. in a hybridization buffer containing 50% formamide, 5×SSC, 7 mM Tris, 1×Denhardt's, 25 μg/ml salmon sperm DNA; wash at 50° C. in 0.1×SSC, 0.1% SDS.

Throughout this application, the following standard abbreviations are used to indicate specific nucleotide bases:

A=adenine
G=guanine
C=cytosine
T=thymine
M=adenine or cytosine
R=adenine or guanine
W=adenine or thymine
S=cytosine or guanine
Y=cytosine or thymine
K=guanine or thymine
V=adenine, cytosine, or guanine (not thymine)
H=adenine, cytosine, or thymine (not cytosine)
B=cytosine, guanine, or thymine (not adenine)
N=adenine, cytosine, guanine, or thymine (or other modified base such as inosine)
I=inosine Furthermore, the term "agonist" is used throughout this application to indicate any peptide or non-peptidyl compound which increases the activity of any of the polypeptides of the subject invention. The term "antagonist" is used throughout this application to indicate any peptide or non-peptidyl compound which decreases the activity of any of the polypeptides of the subject invention.

Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

It is possible that the mammalian SNORF36 receptor gene contains introns and furthermore, the possibility exists that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene. (Burns, et al., 1996; Chu, et al., 1996). Such variants may exhibit pharmacologic properties differing from the polypeptide encoded by the original gene.

This invention provides splice variants of the mammalian SNORF36 receptors disclosed herein. This invention further provides for alternate translation initiation sites and alternately spliced or edited variants of nucleic acids encoding the SNORF36 receptors of this invention.

This invention also contemplates recombinant nucleic acids which comprise nucleic acids encoding naturally occurring allelic variants of the SNORF36 receptors disclosed herein.

Figure 2A:
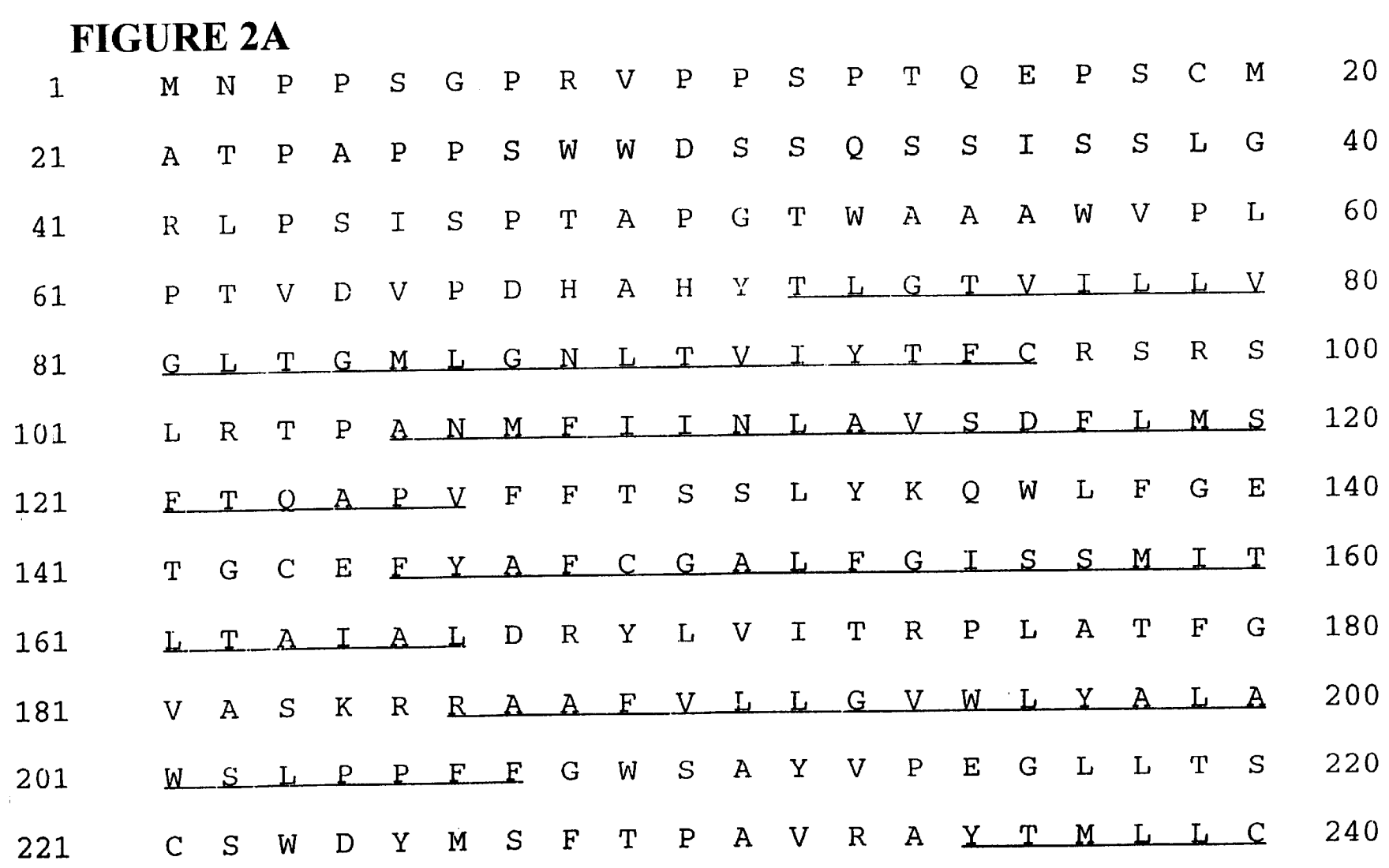
Figure 2B:
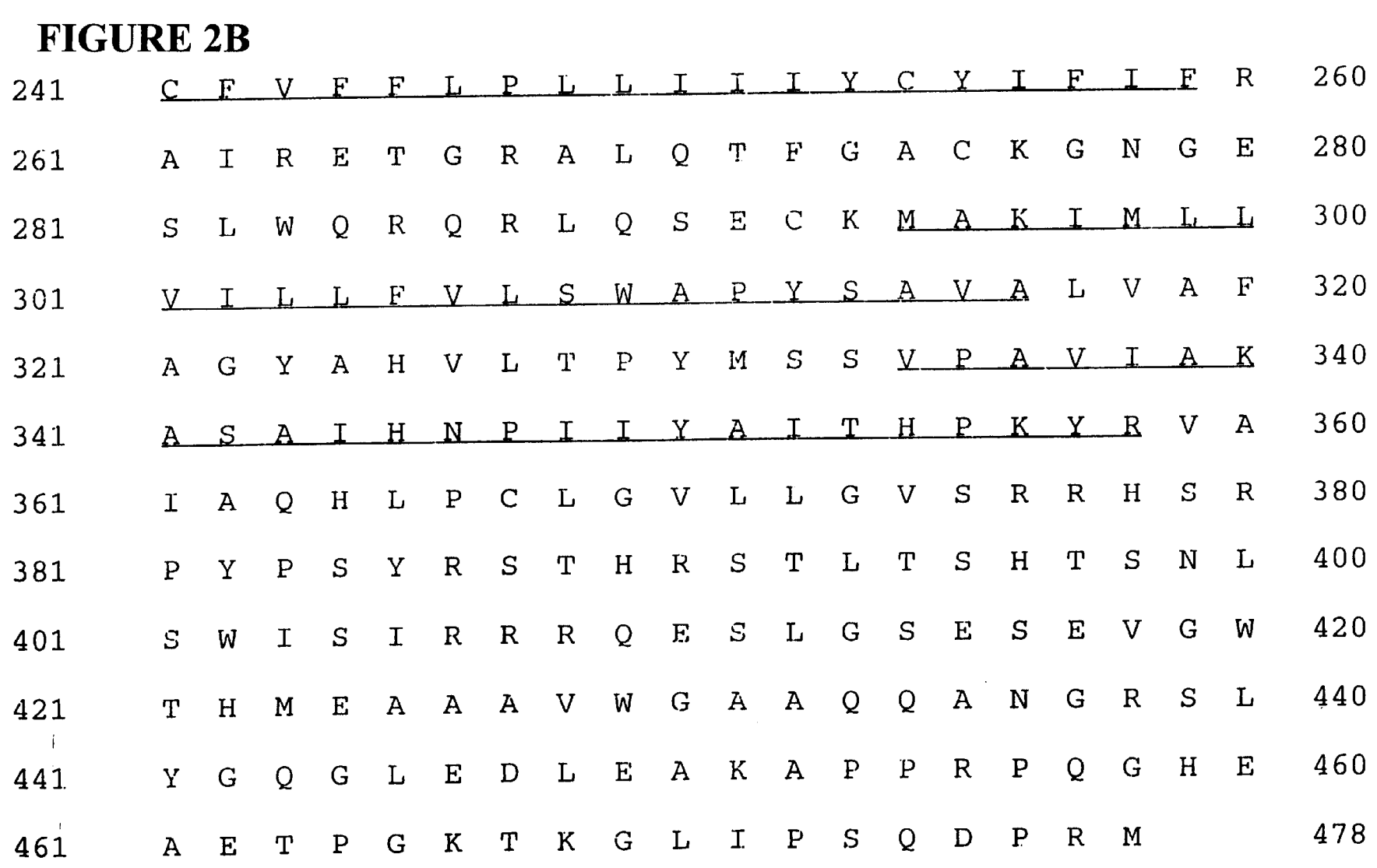

The nucleic acids of the subject invention also include nucleic acid analogs of the human SNORF36a receptor genes, wherein the human SNORF36a receptor gene comprises the nucleic acid sequence shown in FIGS. 1A–1C (SEQ ID NO: 1) or contained in plasmid pcDNA3.1-hSNORF36a-f (ATCC® Accession No. 203977). Nucleic acid analogs of the human SNORF36a receptor genes differ from the human SNORF36a receptor genes described herein in terms of the identity or location of one or more nucleic acid bases (deletion analogs containing less than all of the nucleic acid bases shown in FIGS. 1A–1C or contained in plasmid pcDNA3.1-hSNORF36a-f (ATCC® Accession No. 203977), substitution analogs wherein one or more nucleic acid bases shown in FIGS. 1A–1C or contained in plasmid pcDNA3.1-hSNORF36a-f (ATCC® Accession No. 203977), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 1A–1C or contained in plasmid pcDNA3.1-hSNORF36a-f (ATCC® Accession No. 203977). In one embodiment of the present invention, the nucleic acid analog encodes a protein which has an amino acid sequence identical to that shown in FIGS. 2A–2B or encoded by the nucleic acid sequence contained in pcDNA3.1-hSNORF36a-f (ATCC® Accession No. 203977). In another embodiment, the nucleic acid analog encodes a protein having an amino acid sequence which differs from the amino acid sequences shown in FIGS. 2A–2B or encoded by the nucleic acid contained in plasmid pcDNA3.1-hSNORF36a-f (ATCC® Accession No. 203977). In a further embodiment, the protein encoded by the nucleic acid analog has a function which is the same as the function of the receptor proteins having the amino acid sequence shown in FIGS. 2A–2B. In another embodiment, the function of the protein encoded by the nucleic acid analog differs from the function of the receptor protein having the amino acid sequence shown in FIGS. 2A–2B. In another embodiment, the variation in the nucleic acid sequence occurs within the transmembrane (TM) region of the protein. In a further embodiment, the variation in the nucleic acid sequence occurs outside of the TM region.

Figure 4A:
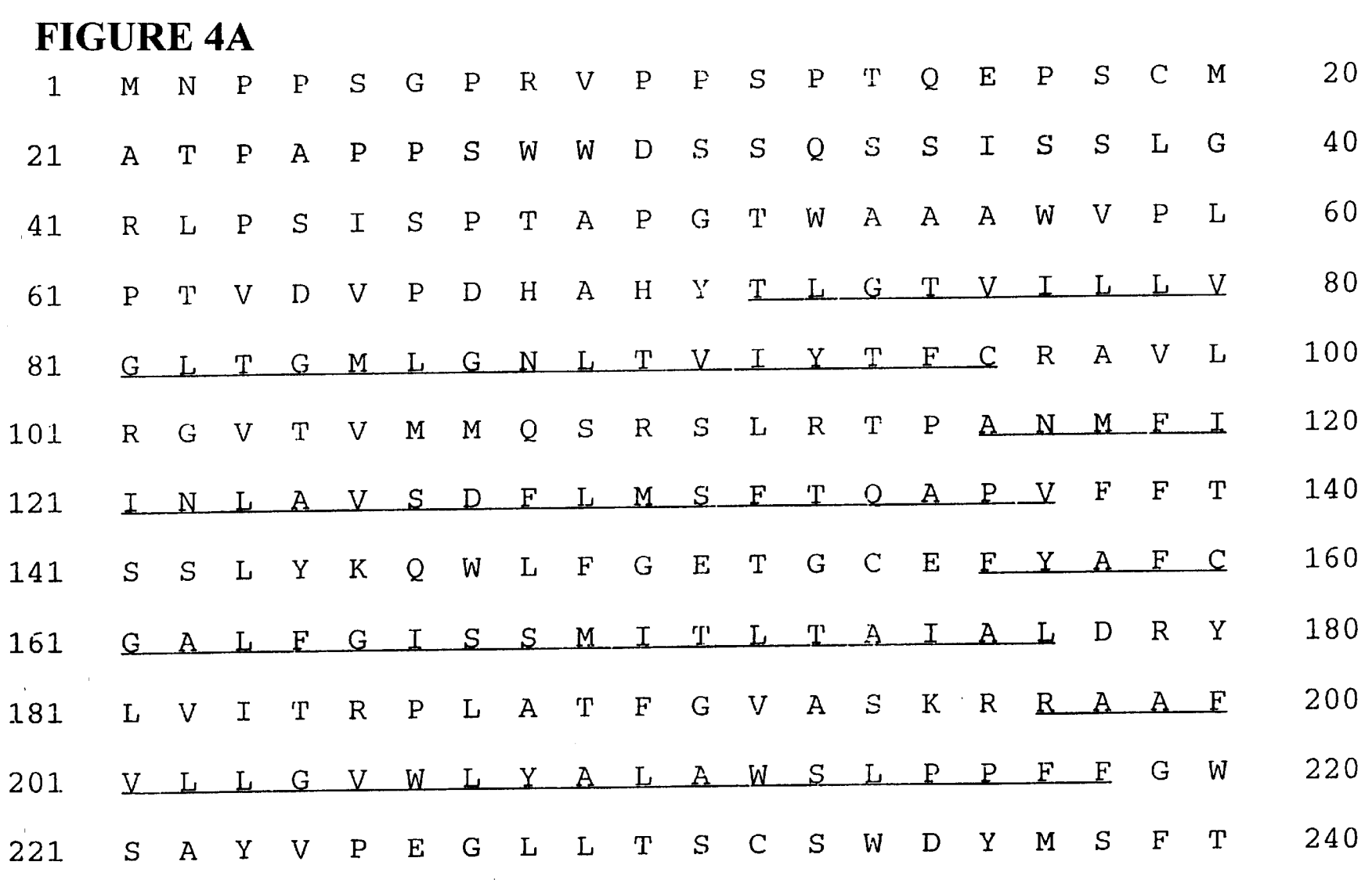
Figure 4B:
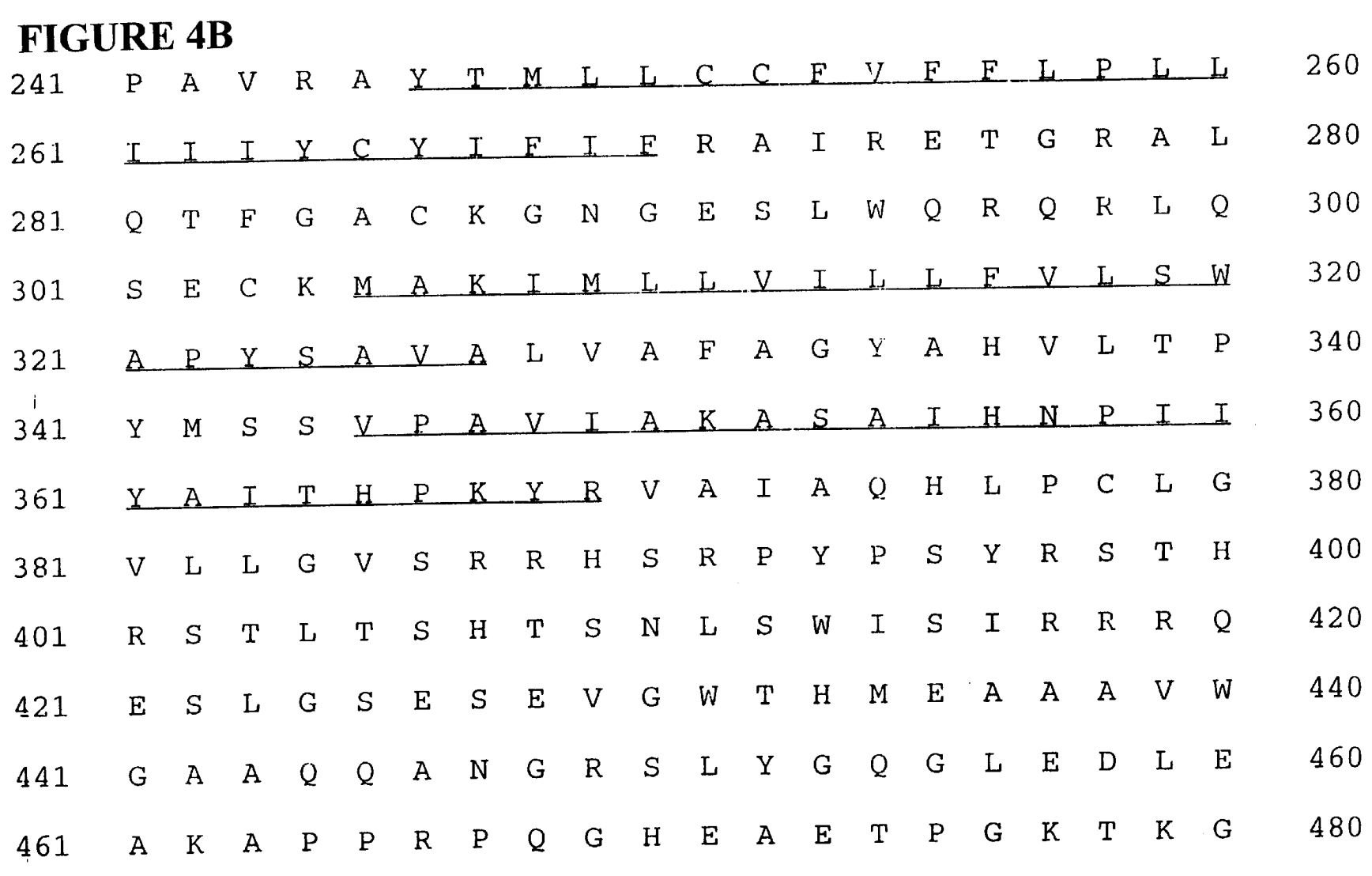

The nucleic acids of the subject invention also include nucleic acid analogs of the human SNORF36b receptor genes, wherein the human SNORF36b receptor gene comprises the nucleic acid sequence shown in FIGS. 3A–3C (SEQ ID NO: 3) or contained in plasmid pcDNA3.1-hSNORF36b-f (ATCC® Accession No. 203976). Nucleic acid analogs of the human SNORF36b receptor genes differ from the human SNORF36b receptor genes described herein in terms of the identity or location of one or more nucleic acid bases (deletion analogs containing less than all of the nucleic acid bases shown in FIGS. 3A–3C or contained in plasmid pcDNA3.1-hSNORF36b-f (ATCC® Accession No. 203976), substitution analogs wherein one or more nucleic acid bases shown in FIGS. 3A–3C or contained in plasmid pcDNA3.1-hSNORF36b-f (ATCC® Accession No. 203976), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 3A–3C or contained in plasmid pcDNA3.1-hSNORF36b-f (ATCC® Accession No. 203976). In one embodiment of the present invention, the nucleic acid analog encodes a protein which has an amino acid sequence identical to that shown in FIGS. 4A–4C or encoded by the nucleic acid sequence contained in pcDNA3.1-hSNORF36b-f (ATCC® Accession No. 203976). In another embodiment, the nucleic acid analog encodes a protein having an amino acid sequence which differs from the amino acid sequences shown in FIGS. 4A–4C or encoded by the nucleic acid contained in plasmid pcDNA3.1-hSNORF36b-f (ATCC® Accession No. 203976). In a further embodiment, the protein encoded by the nucleic acid analog has a function which is the same as the function of the receptor proteins having the amino acid sequence shown in FIGS. 4A–4C. In another embodiment, the function of the protein encoded by the nucleic acid analog differs from the function of the receptor protein having the amino acid sequence shown in FIGS. 4A–4C. In another embodiment, the variation in the nucleic acid sequence occurs within the transmembrane (TM) region of the protein. In a further embodiment, the variation in the nucleic acid sequence occurs outside of the TM region.

The nucleic acids of the subject invention also include nucleic acid analogs of the rat SNORF36 receptor genes, wherein the rat SNORF36 receptor gene comprises the nucleic acid sequence shown in FIG. 5 or contained in plasmid pEXJ.T3T7-rSNORF36p (ATCC® Patent Depository No. PTA-534). Nucleic acid analogs of the rat SNORF36 receptor genes differ from the rat SNORF36 receptor genes described herein in terms of the identity or location of one or more nucleic acid bases deletion analogs containing less than all of the nucleic acid bases shown in FIG. 5 or contained in plasmid pEXJ.T3T7-rSNORF36p (ATCC® Patent Depository No. PTA-534), substitution analogs wherein one or more nucleic acid bases shown in FIG. 5 or contained in plasmid pEXJ.T3T7-rSNORF36p (ATCC® Patent Depository No. PTA-534), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIG. 5 or contained in plasmid pEXJ.T3T7-rSNORF36p (ATCC® Patent Depository No. PTA-534). In one embodiment of the present invention, the nucleic acid analog encodes a protein which has an amino acid sequence identical to that shown in FIG. 6 or encoded by the nucleic acid sequence contained in plasmid pEXJ.T3T7-rSNORF36p (ATCC® Patent Depository No. PTA-534). In another embodiment, the nucleic acid analog encodes a protein having an amino acid sequence which differs from the amino acid sequences shown in FIG. 6 or encoded by the nucleic acid contained in plasmid pEXJ.T3T7-rSNORF36p (ATCC® Patent Depository No. PTA-534). In a further embodiment, the protein encoded by the nucleic acid analog has a function which is the same as the function of the receptor proteins having the amino acid sequence shown in FIG. 6. In another embodiment, the function of the protein encoded by the nucleic acid analog differs from the function of the receptor protein having the amino acid sequence shown in FIG. 6. In another embodiment, the variation in the nucleic acid sequence occurs within the transmembrane (TM) region of the protein. In a further embodiment, the variation in the nucleic acid sequence occurs outside of the TM region.

The nucleic acids of the subject invention also include nucleic acid analogs of the rat SNORF36 receptor genes, wherein the rat SNORF36 receptor gene comprises the nucleic acid sequence shown in FIGS. 9A–9C or contained in plasmid pEXJ.T7-rSNORF36-f (ATCC® Patent Depository No. PTA-1216). Nucleic acid analogs of the rat SNORF36 receptor genes differ from the rat SNORF36 receptor genes described herein in terms of the identity or location of one or more nucleic acid bases deletion analogs containing less than all of the nucleic acid bases shown in FIGS. 9A–9C or contained in plasmid pEXJ.T7-rSNORF36-f (ATCC® Patent Depository No. PTA-1216), substitution analogs wherein one or more nucleic acid bases shown in FIGS. 9A–9C or contained in plasmid pEXJ.T7-rSNORF36-f (ATCC® Patent Depository No. PTA-1216), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 9A–9C or contained in plasmid pEXJ.T7-rSNORF36-f (ATCC® Patent Depository No. PTA-1216). In one embodiment of the present invention, the nucleic acid analog encodes a protein which has an amino acid sequence identical to that shown in FIGS. 10A–10C or encoded by the nucleic acid sequence contained in plasmid pEXJ.T7-rSNORF36-f (ATCC® Patent Depository No. PTA-1216). In another embodiment, the nucleic acid analog encodes a protein having an amino acid sequence which differs from the amino acid sequences shown in FIGS. 10A–10C or encoded by the nucleic acid contained in plasmid pEXJ.T7-rSNORF36-f (ATCC® Patent Depository No. PTA-1216). In a further embodiment, the protein encoded by the nucleic acid analog has a function which is the same as the function of the receptor proteins having the amino acid sequence shown in FIGS. 10A–10C. In another embodiment, the function of the protein encoded by the nucleic acid analog differs from the function of the receptor protein having the amino acid sequence shown in FIGS. 10A–10C. In another embodiment, the variation in the nucleic acid sequence occurs within the transmembrane (TM) region of the protein. In a further embodiment, the variation in the nucleic acid sequence occurs outside of the TM region.

This invention provides the above-described isolated nucleic acid, wherein the nucleic acid is DNA. In an embodiment, the DNA is cDNA. In another embodiment, the DNA is genomic DNA. In still another embodiment, the nucleic acid is PNA. Methods for production and manipulation of nucleic acid molecules are well known in the art.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIGS. 1A–1C (SEQ ID NO: 1) or the nucleotide sequence contained in the plasmid pcDNA3.1-hSNORF36a-f (ATCC® Accession No. 203977), that is, a nucleotide sequence which is translated into the same amino acid sequence. In another embodiment, the nucleic acid comprises a nucleotide sequence which is degenerate with respect to the nucleotide sequence shown in FIGS. 3A–3C (SEQ ID NO: 3) or the nucleotide sequence contained in the plasmid pcDNA3.1-hSNORF36b-f (ATCC® Accession No. 203976), that is, a nucleotide sequence which is translated into the same amino acid sequence.)

In another embodiment, the nucleic acid comprises a nucleotide sequence which is degenerate with respect to the nucleotide sequence shown in FIG. 5 (SEQ ID NO: 5) or FIGS. 9A–9C (SEQ ID NO: 7) or the nucleotide sequence contained in the plasmids pEXJ.T3T7-rSNORF36p (ATCC® Patent Depository No. PTA-534) or pEXJ.T7-rSNORF36-f (ATCC® Patent Depository No. PTA-1216), that is, a nucleotide sequence which is translated into the same amino acid sequence.

This invention also encompasses DNAs and cDNAs which encode amino acid sequences which differ from those of the polypeptides of this invention, but which should not produce phenotypic changes.

Alternately, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors. The creation of polypeptide analogs is well known to those of skill in the art (Spurney, R. F. et al. (1997); Fong, T. M. et al. (1995); Underwood, D. J. et al. (1994); Graziano, M. P. et al. (1996); Guan X. M. et al. (1995)).

The modified polypeptides of this invention may be transfected into cells either transiently or stably using methods well-known in the art, examples of which are disclosed herein. This invention also provides for binding assays using the modified polypeptides, in which the polypeptide is expressed either transiently or in stable cell lines. This invention further provides a compound Identified using a modified polypeptide in a binding assay such as the binding assays described herein.

The nucleic acids described and claimed herein are useful for the information which they provide concerning the amino acid sequence of the polypeptide and as products for the large scale synthesis of the polypeptides by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention also provides an isolated nucleic acid encoding species homologs of the SNORF36 receptor encoded by the nucleic acid sequence shown in FIGS. 1A–1C (SEQ ID NO: 1) or encoded by the plasmid pcDNA3.1-hSNORF36a-f (ATCC® Accession No. 203977). In one embodiment, the nucleic acid encodes a mammalian SNORF36 receptor homolog which has substantially the same amino acid sequence as does the SNORF36 receptor encoded by the plasmid pcDNA3.1-hSNORF36a-f (ATCC® Accession No. 203977). In another embodiment, the nucleic acid encodes a mammalian SNORF36 receptor homolog which has above 75% amino acid identity to the SNORF36 receptor encoded by the plasmid pcDNA3.1-hSNORF36a-f (ATCC® Accession No. 203977); preferably above 85% amino acid identity to the SNORF36 receptor encoded by the plasmid pcDNA3.1-hSNORF36a-f (ATCC® Accession No. 203977); most preferably above 95% amino acid identity to the SNORF36 receptor encoded by the plasmid pcDNA3.1-hSNORF36a-f (ATCC® Accession No. 203977). In another embodiment, the mammalian SNORF36 receptor homolog has above 70% nucleic acid identity to the SNORF36 receptor gene contained in plasmid pcDNA3.1-hSNORF36a-f (ATCC® Accession No. 203977); preferably above 80% nucleic acid identity to the SNORF36 receptor gene contained in the plasmid pcDNA3.1-hSNORF36a-f (ATCC® Accession No. 203977); more preferably above 90% nucleic acid identity to the SNORF36 receptor gene contained in the plasmid pcDNA3.1-hSNORF36a-f (ATCC® Accession No. 203977). Examples of methods for isolating and purifying species homologs are described elsewhere (e.g., U.S. Pat. No. 5,602,024, WO94/14957, WO97/26853, WO98/15570).

This invention also provides an isolated nucleic acid encoding species homologs of the SNORF36 receptors encoded by the nucleic acid sequence shown in FIGS. 3A–3C (SEQ ID NO: 3) or encoded by the plasmid pcDNA3.1-hSNORF36b-f (ATCC® Accession No. 203976). In one embodiment, the nucleic acid encodes a mammalian SNORF36 receptor homolog which has substantially the same amino acid sequence as does the SNORF36 receptor encoded by the plasmid pcDNA3.1-hSNORF36b-f (ATCC® Accession No. 203976). In another embodiment, the nucleic acid encodes a mammalian SNORF36 receptor homolog which has above 75% amino acid identity to the SNORF36 receptor encoded by the plasmid pcDNA3.1-hSNORF36b-f (ATCC® Accession No. 203976); preferably above 85% amino acid identity to the SNORF36 receptor encoded by the plasmid pcDNA3.1-hSNORF36b-f (ATCC® Accession No. 203976); most preferably above 95% amino acid identity to the SNORF36 receptor encoded by the plasmid pcDNA3.1-hSNORF36b-f (ATCC® Accession No. 203976). In another embodiment, the mammalian SNORF36 receptor homolog has above 70% nucleic acid identity to the SNORF36 receptor gene contained in plasmid pcDNA3.1-hSNORF36b-f (ATCC® Accession No. 203976); preferably above 80% nucleic acid identity to the SNORF36 receptor gene contained in the plasmid pcDNA3.1-hSNORF36b-f (ATCC® Accession No. 203976); more preferably above 90% nucleic acid identity to the SNORF36 receptor gene contained in the plasmid pcDNA3.1-hSNORF36b-f (ATCC® Accession No. 203976).

This invention also provides an isolated nucleic acid encoding species homologs of the SNORF36 receptors encoded by the nucleic acid sequence shown in FIG. 5 (SEQ ID NO: 5) or encoded by the plasmid pEXJ.T3T7-rSNORF36p (ATCC® Patent Depository No. PTA-534). In one embodiment, the nucleic acid encodes a mammalian SNORF36 receptor homolog which has substantially the same amino acid sequence as does the SNORF36 receptor encoded by the plasmid pEXJ.T3T7-rSNORF36p (ATCC® Patent Depository No. PTA-534). In another embodiment, the nucleic acid encodes a mammalian SNORF36 receptor homolog which has above 75% amino acid identity to the SNORF36 receptor encoded by the plasmid pEXJ.T3T7-rSNORF36p (ATCC® Patent Depository No. PTA-534); preferably above 85% amino acid identity to the SNORF36 receptor encoded by the plasmid pEXJ.T3T7-rSNORF36p (ATCC® Patent Depository No. PTA-534); most preferably above 95% amino acid identity to the SNORF36 receptor encoded by the plasmid pEXJ.T3T7-rSNORF36p (ATCC® Patent Depository No. PTA-534). In another embodiment, the mammalian SNORF36 receptor homolog has above 70% nucleic acid identity to the SNORF36 receptor gene contained in plasmid pEXJ.T3T7-rSNORF36p (ATCC® Patent Depository No. PTA-534); preferably above 80% nucleic acid identity to the SNORF36 receptor gene contained in the plasmid pEXJ.T3T7-rSNORF36p (ATCC® Patent Depository No. PTA-534); more preferably above 90% nucleic acid identity to the SNORF36 receptor gene contained in the plasmid pEXJ.T3T7-rSNORF36p (ATCC® Patent Depository No. PTA-534).

This invention also provides an isolated nucleic acid encoding species homologs of the SNORF36 receptors encoded by the nucleic acid sequence shown in FIGS. 9A–9C (SEQ ID NO: 7) or encoded by the plasmid pEXJ.T7-rSNORF36-f (ATCC® Patent Depository No. PTA-1216). In one embodiment, the nucleic acid encodes a mammalian SNORF36 receptor homolog which has substantially the same amino acid sequence as does the SNORF36 receptor encoded by the plasmid pEXJ.T7-rSNORF36-f (ATCC® Patent Depository No. PTA- 1216). In another embodiment, the nucleic acid encodes a mammalian SNORF36 receptor homolog which has above 75% amino acid identity to the SNORF36 receptor encoded by the pEXJ.T7-rSNORF36-f (ATCC® Patent Depository No. PTA-1216); preferably above 85% amino acid identity to the SNORF36 receptor encoded by the plasmid pEXJ.T7-rSNORF36-f (ATCC® Patent Depository No. PTA-1216); most preferably above 95% amino acid identity to the SNORF36 receptor encoded by the plasmid pEXJ.T7-rSNORF36-f (ATCC® Patent Depository No. PTA-1216). In another embodiment, the mammalian SNORF36 receptor homolog has above 70% nucleic acid identity to the SNORF36 receptor gene contained in plasmid pEXJ.T7-rSNORF36-f (ATCC® Patent Depository No. PTA-1216); preferably above 80% nucleic acid identity to the SNORF36 receptor gene contained in the plasmid pEXJ.T7-rSNORF36-f (ATCC® Patent Depository No. PTA-1216); more preferably above 90% nucleic acid identity to the SNORF36 receptor gene contained in the plasmid pEXJ.T7-rSNORF36-f (ATCC® Patent Depository No. PTA-1216).

This invention provides an isolated nucleic acid encoding a modified mammalian SNORF36 receptor, which differs from a mammalian SNORF36 receptor by having an amino acid(s) deletion, replacement, or addition in the third intracellular domain.

This invention provides an isolated nucleic acid encoding a mammalian SNORF36 receptor. In one embodiment, the nucleic acid is DNA. In another embodiment, the DNA is cDNA. In another embodiment, the DNA is genomic DNA. In another embodiment, the nucleic acid is RNA.

In another embodiment, the mammalian SNORF36 receptor is a human SNORF36a receptor. In another embodiment, the human SNORF36a receptor has an amino acid sequence identical to that encoded by the pcDNA3.1-hSNORF36a-f (ATCC® Accession No. 203977). In another embodiment, the human SNORF36a receptor has an amino acid sequence identical to the amino acid sequence shown in FIGS. 2A–2B (SEQ ID NO: 2).

In another embodiment, the mammalian SNORF36 receptor is a human SNORF36b receptor. In another embodiment, the human SNORF36b receptor has an amino acid sequence identical to that encoded by the plasmid pcDNA3.1-hSNORF36b-f (ATCC® Accession No. 203976). In another embodiment, the human SNORF36b receptor has an amino acid sequence identical to the amino acid sequence shown in FIGS. 4A–4C (SEQ ID NO: 4).

In an embodiment, the mammalian SNORF36 receptor is a rat SNORF36 receptor. In another embodiment, the rat SNORF36 receptor has an amino acid sequence identical to that encoded by the plasmid pEXJ.T7-rSNORF36-f (ATCC® Patent Depository No. PTA-1216). In another embodiment, the rat SNORF36 receptor has an amino acid sequence identical to the amino acid sequence shown in FIGS. 10A–10C (SEQ ID NO: 8).

This invention provides a purified mammalian SNORF36 receptor protein. In one embodiment, the SNORF36 receptor protein is a human SNORF36a receptor protein. In another embodiment, the SNORF36 receptor protein is a human SNORF36b receptor protein. In a further embodiment, the SNORF36 receptor protein is a rat SNORF36 receptor protein.

This invention provides a vector comprising the nucleic acid of this invention. This invention further provides a vector adapted for expression in a cell which comprises the regulatory elements necessary for expression of the nucleic acid in the cell operatively linked to the nucleic acid encoding the receptor so as to permit expression thereof, wherein the cell is a bacterial, amphibian, yeast, insect or mammalian cell. In one embodiment, the vector is a baculovirus. In another embodiment, the vector is a plasmid.

This invention provides a plasmid designated pcDNA3.1-hSNORF36a-f (ATCC® Accession No. 203977). This invention also provides a plasmid designated pcDNA3.1-hSNORF36b-f (ATCC® Accession No. 203976). This invention provides a plasmid designated pEXJ.T3T7-rSNORF36p (ATCC® Patent Depository No. PTA-534).

This invention provides a plasmid designated pEXJ.T7-prSNORF36-f (ATCC® Patent Depository No. PTA-1216).

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used in an embodiment, the vector or plasmid comprises the coding sequence of the polypeptide and the regulatory elements necessary for expression in the host cell.

This invention provides for a cell comprising the vector of this invention. In one embodiment, the cell is a non-mammalian cell. In one embodiment, the non-mammalian cell is a Xenopus oocyte cell or a Xenopus melanophore cell. In another embodiment, the cell is a mammalian cell. In another embodiment, the cell is a COS-7 cell, a 293 human embryonic kidney cell, a NIH-3T3 cell, a LM(tk−) cell, a mouse Y1 cell, or a CHO cell. In another embodiment, the cell is an insect cell. In another embodiment, the insect cell is an Sf9 cell, an Sf21 cell or a Trichoplusia ni 5B-4 cell.

This invention provides a membrane preparation isolated from the cell in accordance with this invention.

Furthermore, this invention provides for a nucleic acid probe comprising at least 15 nucleotides, which probe specifically hybridizes with a nucleic acid encoding a mammalian SNORF36 receptor, wherein the probe has a sequence complementary to a unique sequence present within one of the two strands of the nucleic acid encoding the mammalian SNORF36 receptor contained in plasmid pcDNA3.1-hSNORF36a-f (ATCC® Accession No. 203977), plasmid pcDNA3.1-hSNORF36b-f (ATCC® Accession No. 203976), plasmid pEXJ.T3T7-rSNORF36p (ATCC® Patent Depository No. PTA-534) or plasmid pEXJ.T7-rSNORF36-f (ATCC® Patent Depository No. PTA-1216).

This invention further provides a nucleic acid probe comprising at least 15 nucleotides, which probe specifically hybridizes with a nucleic acid encoding a mammalian SNORF36 receptor, wherein the probe has a sequence complementary to a unique sequence present within (a) the nucleic acid sequence shown in FIGS. 1A–1C (SEQ ID NO: 1) or (b) the reverse complement thereof. This invention further provides a nucleic acid probe comprising at least 15 nucleotides, which probe specifically hybridizes with a nucleic acid encoding a mammalian SNORF36 receptor, wherein the probe has a sequence complementary to a unique sequence present within (a) the nucleic acid sequence shown in FIGS. 3A–3C (SEQ ID NO: 3) or (b) the reverse complement thereof. This invention also provides a nucleic acid probe comprising at least 15 nucleotides, which probe specifically hybridizes with a nucleic acid encoding a mammalian SNORF36 receptor, wherein the probe has a sequence complementary to a unique sequence present within (a) the nucleic acid sequence shown in FIG. 5 (SEQ ID NO: 5) or (b) the reverse complement thereof. This invention also provides a nucleic acid probe comprising at least 15 nucleotides, which probe specifically hybridizes with a nucleic acid encoding a mammalian SNORF36 receptor, wherein the probe has a sequence complementary to a unique sequence present within (a) the nucleic acid sequence shown in FIGS. 9A–9C (SEQ ID NO: 7) or (b) the reverse complement thereof. In one embodiment, the nucleic acid is DNA. In another embodiment, the nucleic acid is RNA.

As used herein, the phrase "specifically hybridizing" means the ability of a nucleic acid molecule to recognize a nucleic acid sequence complementary to its own and to form double-helical segments through hydrogen bonding between complementary base pairs.

The nucleic acids of this Invention may be used as probes to obtain homologous nucleic acids from other species and to detect the existence of nucleic acids having complementary sequences in samples.

The nucleic acids may also be used to express the receptors they encode in transfected cells.

The use of a constitutively active receptor encoded by SNORF36 either occurring naturally without further modification or after appropriate point mutations, deletions or the like, allows screening for antagonists and in vivo use of such antagonists to attribute a role to receptor SNORF36 without prior knowledge of the endogenous ligand.

Use of the nucleic acids further enables elucidation of possible receptor diversity and of the existence of multiple subtypes within a family of receptors of which SNORF36 is a member.

Finally, it is contemplated that this receptor will serve as a valuable tool for designing drugs for treating various pathophysiological conditions such as chronic and acute inflammation, arthritis, autoimmune diseases, transplant rejection, graft vs. host disease, bacterial, fungal, protozoan and viral infections, septicemia, AIDS, pain, psychotic and neurological disorders, including anxiety, depression, schizophrenia, dementia, mental retardation, memory loss, epilepsy, neuromotor disorders, locomotor problems, respiratory disorders, asthma, eating/body weight disorders including obesity, bulimia, diabetes, anorexia, nausea, hypertension, hypotension, vascular and cardiovascular disorders, ischemia, stroke, cancers, ulcers, urinary retention, sexual/reproductive disorders, circadian rhythm disorders, renal disorders, bone diseases including osteoporosis, benign prostatlc hypertrophy, gastrointestinal disorders, nasal congestion, dermatological disorders such as psoriasis, allergies, Parkinson's disease, Alzheimer's disease, acute heart failure, angina disorders, delirium, dyskinesias such as Huntington's disease or Gille's de la Tourette's syndrome, among others and diagnostic assays for such conditions. This receptor may also serve as a valuable tool for designing drugs for chemoprevention.

Methods of transfecting cells e.g. mammalian cells, with such nucleic acid to obtain cells in which the receptor is expressed on the surface of the cell are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

Such transfected cells may also be used to test compounds and screen compound libraries to obtain compounds which bind to the SNORF36 receptor, as well as compounds which activate or inhibit activation of functional responses in such cells, and therefore are likely to do so in vivo. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention further provides an antibody capable of binding to a mammalian SNORF36 receptor encoded by a nucleic acid encoding a mammalian receptor. In one embodiment, the mammalian SNORF36 receptor is a human SNORF36a receptor or a human SNORF36b receptor. In a further embodiment, the mammalian SNORF36 receptor is a rat SNORF36 receptor.

This invention also provides an agent capable of competitively inhibiting the binding of the antibody to a mammalian SNORF36 receptor. In one embodiment, the antibody is a monoclonal antibody or antisera.

Methods of preparing and employing antisense oligonucleotides, antibodies, nucleic acid probes and transgenic animals directed to the SNORF36 receptor are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention provides for an antisense oligonucleotide having a sequence capable of specifically hybridizing to RNA encoding a mammalian SNORF36 receptor, so as to prevent translation of such RNA. This invention further provides for an antisense oligonucleotide having a sequence capable of specifically hybridizing to genomic DNA encoding a mammalian SNORF36 receptor, so as to prevent transcription of such genomic DNA. In one embodiment, the oligonucleotide comprises chemically modified nucleotides or nucleotide analogues.

This invention also provides for an antibody capable of binding to a mammalian SNORF36 receptor encoded by a nucleic acid in accordance with this invention. In an embodiment, the mammalian SNORF36 receptor is a human SNORF36a receptor or a human SNORF36b receptor. In a further embodiment, the mammalian SNORF36 receptor is a rat SNORF36 receptor.

Moreover, this invention provides an agent capable of competitively inhibiting the binding of an antibody in accordance with this invention to a mammalian SNORF36 receptor. In one embodiment, the antibody is a monoclonal antibody or antisera.

This invention still further provides a pharmaceutical composition comprising (a) an amount of an oligonucleotide in accordance with this invention capable of passing through a cell membrane and effective to reduce expression of a mammalian SNORF36 receptor and (b) a pharmaceutically acceptable carrier capable of passing through the cell membrane. In one embodiment, the oligonucleotide is coupled to a substance which inactivates mRNA. In another embodiment, the substance which inactivates mRNA is a ribozyme. In another embodiment, the pharmaceutically acceptable carrier comprises a structure which binds to a mammalian SNORF36 receptor on a cell capable of being taken up by the cells after binding to the structure. In another embodiment, the pharmaceutically acceptable carrier is capable of binding to a mammalian SNORF36 receptor which is specific for a selected cell type.

This invention also provides a pharmaceutical composition which comprises an amount of an antibody in accordance with this invention effective to block binding of a ligand to a human SNORF36a receptor or a human SNORF36b receptor and a pharmaceutically acceptable carrier.

This invention further provides a transgenic, nonhuman mammal expressing DNA encoding a mammalian SNORF36 receptor in accordance with this invention. This invention provides a transgenic, nonhuman mammal comprising a homologous recombination knockout of a native mammalian SNORF36 receptor. This invention further provides a transgenic, nonhuman mammal whose genome comprises antisense DNA complementary to DNA encoding a mammalian SNORF36 receptor in accordance with this invention so placed within such genome as to be transcribed into antisense mRNA which is complementary and hybridizes with mRNA encoding the mammalian SNORF36 receptor so as to thereby reduce translation or such mRNA and expression of such receptor. In one embodiment, the DNA encoding the mammalian SNORF36 receptor additionally comprises an inducible promoter. In another embodiment, the DNA encoding the mammalian SNORF36 receptor additionally comprises tissue specific regulatory elements. In another embodiment, the transgenic, nonhuman mammal is a mouse.

This invention provides for a process for identifying a chemical compound which specifically binds to a mammalian SNORF36 receptor which comprises contacting cells containing DNA encoding, and expressing on their cell surface, the mammalian SNORF36 receptor, wherein such cells do not normally express the mammalian SNORF36 receptor, with the compound under conditions suitable for binding, and detecting specific binding of the chemical compound to the mammalian SNORF36 receptor. This invention further provides for a process for identifying a chemical compound which specifically binds to a mammalian SNORF36 receptor which comprises contacting a membrane preparation from cells containing DNA encoding and expressing on their cell surface the mammalian SNORF36 receptor, wherein such cells do not normally express the mammalian SNORF36 receptor, with the compound under conditions suitable for binding, and detecting specific binding of the chemical compound to the mammalian SNORF36 receptor.

In an embodiment, the mammalian SNORF36 receptor is a human SNORF36a receptor or a human SNORF36b receptor. In another embodiment, the mammalian SNORF36 receptor has substantially the same amino acid sequence as the human SNORF36a receptor encoded by plasmid pcDNA3.1-hSNORF36a-f (ATCC® Accession No. 203977). In another embodiment, the mammalian SNORF36 receptor has substantially the same amino acid sequence as the human SNORF36b receptor encoded by plasmid pcDNA3.1-hSNORF36b-f (ATCC® Accession No. 203976). In another embodiment, the mammalian SNORF36 receptor has substantially the same amino acid sequence as that shown in FIGS. 2A–2B (SEQ ID NO: 2) or FIGS. 4A–4C (SEQ ID NO: 4). In another embodiment, the mammalian SNORF36 receptor has the amino acid sequence shown in FIGS. 2A–2B (SEQ ID NO: 2) or FIGS. 4A–4C (SEQ ID NO: 4).

In another embodiment, the mammalian SNORF36 receptor is a rat SNORF36 receptor. In another embodiment, the mammalian SNORF36 receptor has substantially the same amino acid sequence as the rat SNORF36 receptor encoded by plasmid pEXJ.T7-rSNORF36-f (ATCC® Patent Depository No. PTA-1216). In another embodiment, the mammalian SNORF36 receptor has substantially the same amino acid sequence as that shown in FIGS. 10A–10C (SEQ ID NO: 8).

Figure 10A:
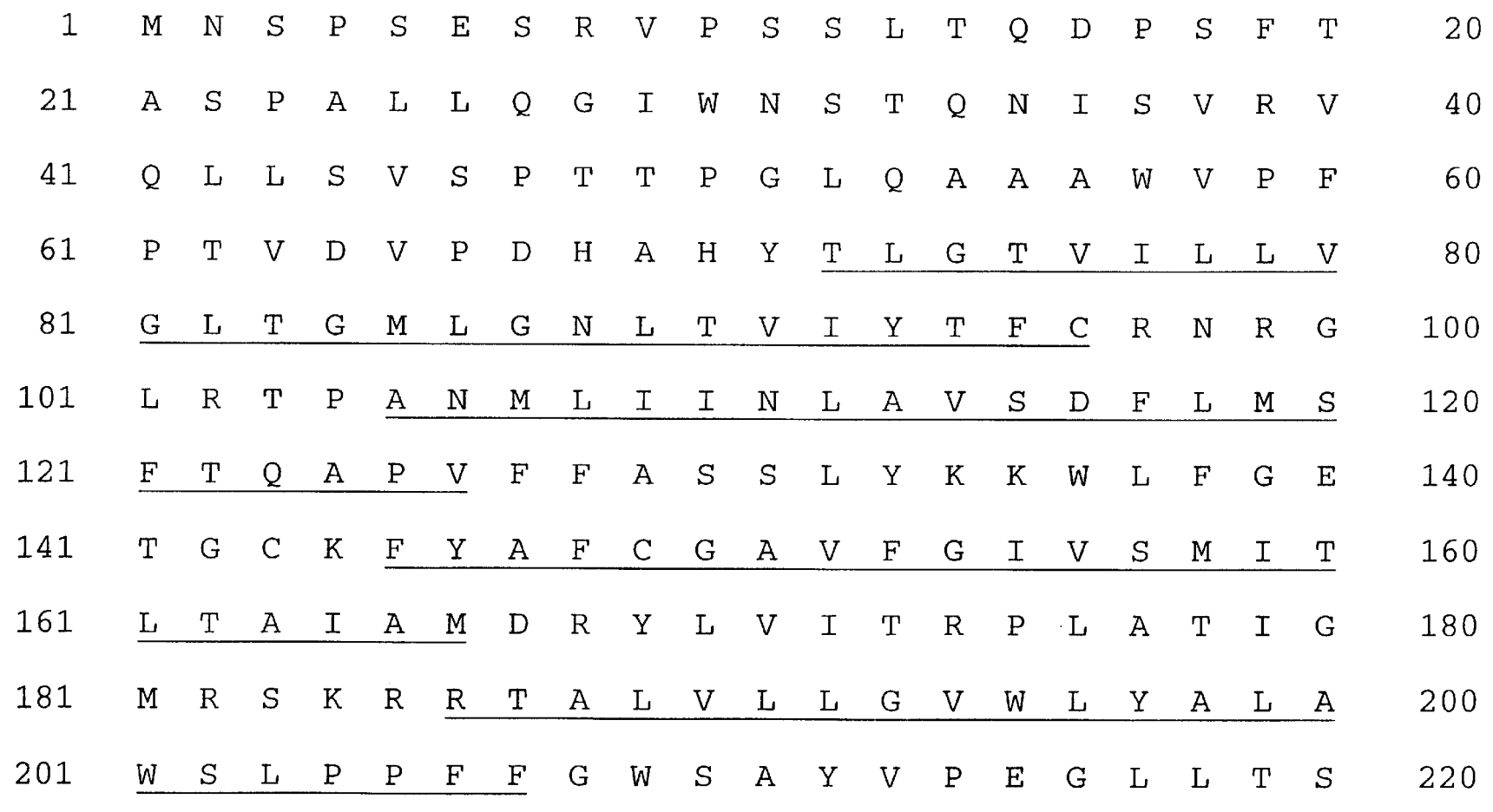
Figure 10B:
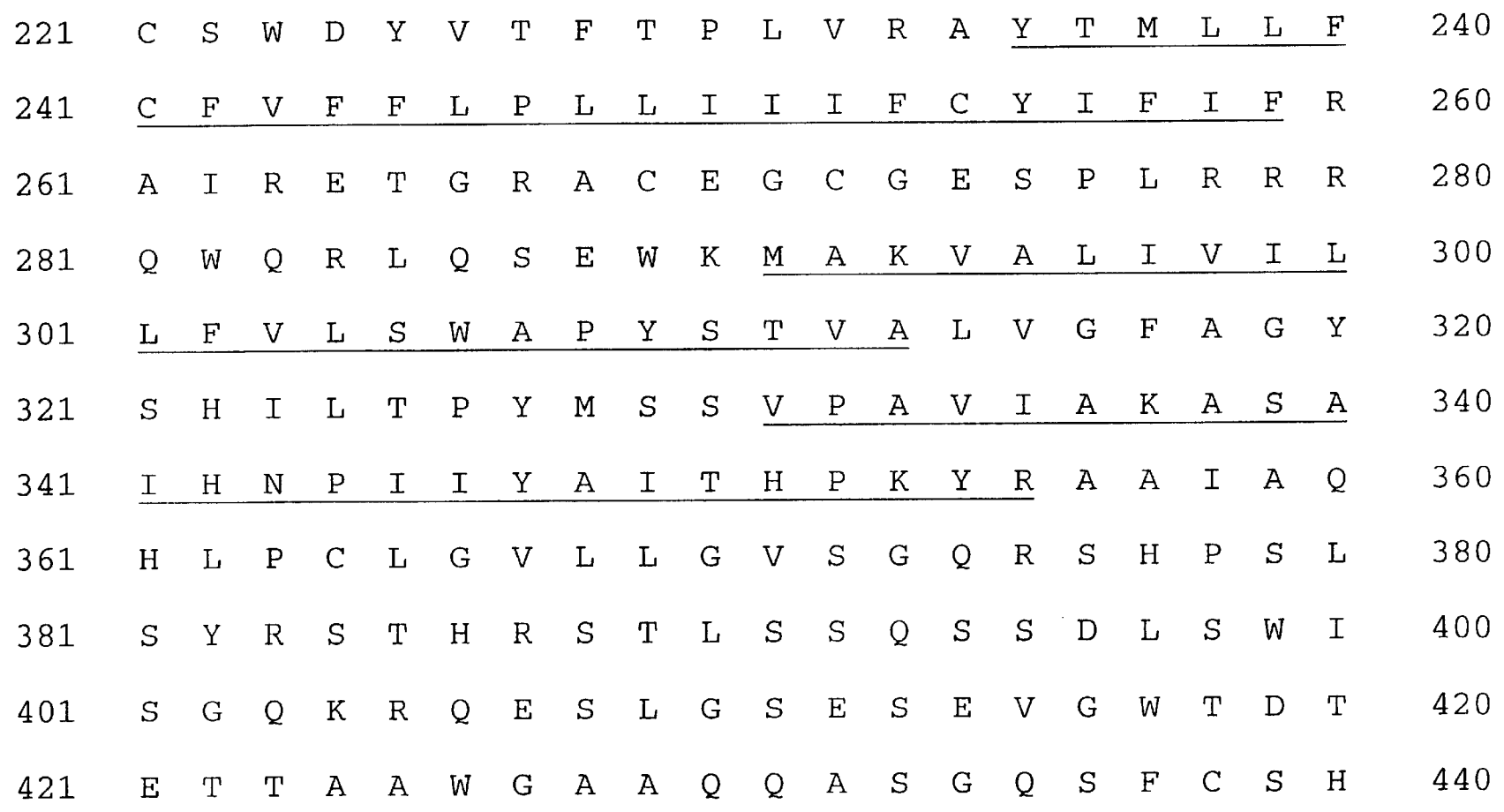

In another embodiment, the mammalian SNORF36 receptor has the amino acid sequence shown in FIGS. 10A–10C (SEQ ID NO: 8).

In one embodiment, the compound is not previously known to bind to a mammalian SNORF36 receptor. In one embodiment, the cell is an insect cell. In one embodiment, the cell is a mammalian cell. In another embodiment, the cell is nonneuronal in origin. In another embodiment, the nonneuronal cell is a COS-7 cell, 293 human embryonic kidney cell, a CHO cell, a NIH-3T3 cell, a mouse Y1 cell, or a LM(tk−) cell. In another embodiment, the compound is a compound not previously known to bind to a mammalian SNORF36 receptor. This invention provides a compound identified by the preceding process according to this invention.

This invention still further provides a process involving competitive binding for identifying a chemical compound which specifically binds to a mammalian SNORF36 receptor which comprises separately contacting cells expressing on their cell surface the mammalian SNORF36 receptor, wherein such cells do not normally express the mammalian SNORF36 receptor, with both the chemical compound and a second chemical compound known to bind to the receptor, and with only the second chemical compound, under conditions suitable for binding of such compounds to the receptor, and detecting specific binding of the chemical compound to the mammalian SNORF36 receptor, a decrease in the binding of the second chemical compound to the mammalian SNORF36 receptor in the presence of the chemical compound being tested indicating that such chemical compound binds to the mammalian SNORF36 receptor.

This invention provides a process involving competitive binding for identifying a chemical compound which specifically binds to a mammalian SNORF36 receptor which comprises separately contacting a membrane preparation from cells expressing on their cell surface the mammalian SNORF36 receptor, wherein such cells do not normally express the mammalian SNORF36 receptor, with both the chemical compound and a second chemical compound known to bind to the receptor, and with only the second chemical compound, under conditions suitable for binding of such compounds to the receptor, and detecting specific binding of the chemical compound to the mammalian SNORF36 receptor, a decrease in the binding of the second chemical compound to the mammalian SNORF36 receptor in the presence of the chemical compound being tested indicating that such chemical compound binds to the mammalian SNORF36 receptor.

In an embodiment of the present invention, the second chemical compound is a retinoic acid derivative. Examples of retinoic acid derivatives include, but are not limited to, all-trans retinoic acid (ATRA), 9-cis-retinal, 13-cis-retinal, and all-trans-retinal.

In one embodiment, the mammalian SNORF36 receptor is a human SNORF36a receptor or a human SNORF36b receptor. In another embodiment, the mammalian SNORF36 receptor is a rat SNORF36 receptor. In a further embodiment, the cell is an insect cell. In another embodiment, the cell is a mammalian cell. In another embodiment, the cell is nonneuronal in origin. In another embodiment, the nonneuronal cell is a COS-7 cell, 293 human embryonic kidney cell, a CHO cell, a NIH-3T3 cell, a mouse Y1 cell, or a LM(tk−) cell. In another embodiment, the compound is not previously known to bind to a mammalian SNORF36 receptor. This invention provides for a compound identified by the preceding process according to this invention.

This invention provides for a method of screening a plurality of chemical compounds not known to bind to a mammalian SNORF36 receptor to identify a compound which specifically binds to the mammalian SNORF36 receptor, which comprises (a) contacting cells transfected with, and expressing, DNA encoding the mammalian SNORF36 receptor with a compound known to bind specifically to the mammalian SNORF36 receptor; (b) contacting the cells of step (a) with the plurality of compounds not known to bind specifically to the mammalian SNORF36 receptor, under conditions permitting binding of compounds known to bind to the mammalian SNORF36 receptor; (c) determining whether the binding of the compound known to bind to the mammalian SNORF36 receptor is reduced in the presence of the plurality of compounds, relative to the binding of the compound in the absence of the plurality of compounds; and if so (d) separately determining the binding to the mammalian SNORF36 receptor of each compound included in the plurality of compounds, so as to thereby identify any compound included therein which specifically binds to the mammalian SNORF36 receptor.

This invention provides a method of screening a plurality of chemical compounds not known to bind to a mammalian SNORF36 receptor to identify a compound which specifically binds to the mammalian SNORF36 receptor, which comprises (a) contacting a membrane preparation from cells transfected with, and expressing, DNA encoding the mammalian SNORF36 receptor with the plurality of compounds not known to bind specifically to the mammalian SNORF36 receptor under conditions permitting binding of compounds known to bind to the mammalian SNORF36 receptor; (b) determining whether the binding of a compound known to bind to the mammalian SNORF36 receptor is reduced in the presence of the plurality of compounds, relative to the binding of the compound in the absence of the plurality of compounds; and if so (c) separately determining the binding to the mammalian SNORF36 receptor of each compound included in the plurality of compounds, so as to thereby identify any compound included therein which specifically binds to the mammalian SNORF36 receptor.

In one embodiment, the mammalian SNORF36 receptor is a human SNORF36a receptor or a human SNORF36b receptor. In a further embodiment, the mammalian SNORF36 receptor is a rat SNORF36 receptor. In another embodiment, the cell is a mammalian cell. In another embodiment, the mammalian cell is non-neuronal in origin. In a further embodiment, the non-neuronal cell is a COS-7 cell, a 293 human embryonic kidney cell, a LM(tk−) cell, a CHO cell, a mouse Y1 cell, or an NIH-3T3 cell.

This invention also provides a method of detecting expression of a mammalian SNORF36 receptor by detecting the presence of mRNA coding for the mammalian SNORF36 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF36 receptor by the cell.

This invention further provides for a method of detecting the presence of a mammalian SNORF36 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF36 receptor on the surface of the cell.

This invention still further provides a method of determining the physiological effects of varying levels of activity of mammalian SNORF36 receptors which comprises producing a transgenic, nonhuman mammal in accordance with this invention whose levels of mammalian SNORF36 receptor activity are varied by use of an inducible promoter which regulates mammalian SNORF36 receptor expression.

This invention additionally provides a method of determining the physiological effects of varying levels of activity of mammalian SNORF36 receptors which comprises producing a panel of transgenic, nonhuman mammals in accordance with this invention each expressing a different amount of mammalian SNORF36 receptor.

Moreover, this invention provides method for identifying an antagonist capable of alleviating an abnormality wherein the abnormality is alleviated by decreasing the activity of a mammalian SNORF36 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF36 receptor, the alleviation of such an abnormality identifying the compound as an antagonist. In an embodiment, the mammalian SNORF36 receptor is a human SNORF36a receptor or a human SNORF36b receptor. In a further embodiment, the mammalian SNORF36 receptor is a rat SNORF36 receptor. The invention also provides an antagonist identified by the preceding method according to this invention. This invention further provides a composition, e.g. a pharmaceutical composition comprising an antagonist according to this invention and a carrier, e.g. a pharmaceutically acceptable carrier. This invention provides a method of treating an abnormality in a subject wherein the abnormality is alleviated by decreasing the activity of a mammalian SNORF36 receptor which comprises administering to the subject an effective amount of the pharmaceutical composition according to this invention so as to thereby treat the abnormality.

In addition, this invention provides a method for identifying an agonist capable of alleviating an abnormality in a subject wherein the abnormality is alleviated by increasing the activity of a mammalian SNORF36 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist. In an embodiment, the mammalian SNORF36 receptor is a human SNORF36a receptor or a human SNORF36b receptor. In a further embodiment, the mammalian SNORF36 receptor is a rat SNORF36 receptor. This invention provides an agonist identified by the preceding method according to this invention. This invention provides a composition, e.g. a pharmaceutical composition comprising an agonist identified by a method according to this invention and a carrier, e.g. a pharmaceutically acceptable carrier.

Moreover, this invention provides a method of treating an abnormality in a subject wherein the abnormality is alleviated by increasing the activity of a mammalian SNORF36 receptor which comprises administering to the subject an effective amount of the pharmaceutical composition of this invention so as to thereby treat the abnormality.

Yet further, this invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF36 receptor and labeled with a detectable marker; (e) detecting labeled bands which have hybridized to the DNA encoding a mammalian SNORF36 receptor to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

In one embodiment, the disorder is a disorder associated with the activity of a specific mammalian allele is diagnosed.

This invention also provides a method of preparing a purified mammalian SNORF36 receptor according to this invention which comprises: (a) culturing cells which express the mammalian SNORF36 receptor; (b) recovering the mammalian SNORF36 receptor from the cells; and (c) purifying the mammalian SNORF36 receptor so recovered.

This invention further provides a method of preparing a purified mammalian SNORF36 receptor according to this invention which comprises: (a) inserting a nucleic acid encoding the mammalian SNORF36 receptor into a suitable expression vector; (b) introducing the resulting vector into a suitable host cell; (c) placing the resulting host cell in suitable condition permitting the production of the mammalian SNORF36 receptor; (d) recovering the mammalian SNORF36 receptor so produced; and optionally (e) isolating and/or purifying the mammalian SNORF36 receptor so recovered.

Furthermore, this invention provides a process for determining whether a chemical compound is a mammalian SNORF36 receptor agonist which comprises contacting cells transfected with and expressing DNA encoding the mammalian SNORF36 receptor with the compound under conditions permitting the activation of the mammalian SNORF36 receptor, and detecting any increase in mammalian SNORF36 receptor activity, so as to thereby determine whether the compound is a mammalian SNORF36 receptor agonist.

This invention also provides a process for determining whether a chemical compound is a mammalian SNORF36 receptor antagonist which comprises contacting cells transfected with and expressing DNA encoding the mammalian SNORF36 receptor with the compound in the presence of a known mammalian SNORF36 receptor agonist, under conditions permitting the activation of the mammalian SNORF36 receptor, and detecting any decrease in mammalian SNORF36 receptor activity, so as to thereby determine whether the compound is a mammalian SNORF36 receptor antagonist.

In an embodiment, the mammalian SNORF36 receptor Us a human SNORF36a receptor or a human SNORF36b receptor. In another embodiment, the mammalian SNORF36 receptor is a rat SNORF36 receptor.

This invention still further provides a composition, for example a pharmaceutical composition, which comprises an amount of a mammalian SNORF36 receptor agonist determined by a process according to this invention effective to increase activity of a mammalian SNORF36 receptor and a carrier, for example, a pharmaceutically acceptable carrier. In one embodiment, the mammalian SNORF36 receptor agonist is not previously known.

Also, this invent on provides a composition, for example a pharmaceutical composition, which comprises an amount of a mammalian SNORF36 receptor antagonist determined by a process according to this invention effective to reduce activity of a mammalian SNORF36 receptor and a carrier, for example, a pharmaceutically acceptable carrier. In one embodiment, the mammalian SNORF36 receptor antagonist is not previously known.

This invention moreover provides a process for determining whether a chemical compound specifically binds to and activates a mammalian SNORF36 receptor, which comprises contacting cells producing a second messenger response and expressing on their cell surface the mammalian SNORF36 receptor, wherein such cells do not normally express the mammalian SNORF36 receptor, with the chemical compound under conditions suitable for activation of the mammalian SNORF36 receptor, and measuring the second messenger response in the presence and in the absence of the chemical compound, a change, e.g. an increase, in the second messenger response in the presence of the chemical compound indicating that the compound activates the mammalian SNORF36 receptor.

In one embodiment, the second messenger response comprises chloride channel activation and the change in second messenger is an increase in the level of chloride current. In another embodiment, the second messenger response comprises change in intracellular calcium levels and the change in second messenger is an increase in the measure of intracellular calcium. In another embodiment, the second messenger response comprises release of inositol phosphate and the change in second messenger is an increase in the level of inositol phosphate. In another embodiment, the second messenger response comprises release of arachidonic acid and the change in second messenger is an increase in the level of arachidonic acid. In yet another embodiment, the second messenger response comprises GTPγS ligand binding and the change in second messenger is an increase in GTPγS ligand binding. In another embodiment, the second messenger response comprises activation of MAP kinase and the change in second messenger response is an increase in MAP kinase activation. In a further embodiment, the second messenger response comprises cAMP accumulation and the change in second messenger response is a reduction in cAMP accumulation.

This invention still further provides a process for determining whether a chemical compound specifically binds to and inhibits activation of a mammalian SNORF36 receptor, which comprises separately contacting cells producing a second messenger response and expressing on their cell surface the mammalian SNORF36 receptor, wherein such cells do not normally express the mammalian SNORF36 receptor, with both the chemical compound and a second chemical compound known to activate the mammalian SNORF36 receptor, and with only the second chemical compound, under conditions suitable for activation of the mammalian SNORF36 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian SNORF36 receptor.

In an embodiment of the present invention, the second chemical compound is a retinoic acid derivative. Examples of retinoic acid derivatives include, but are not limited to, all-trans retinoic acid (ATRA), 9-cis-retinal, 13-cis-retinal, and all-trans-retinal.

In one embodiment, the second messenger response comprises chloride channel activation and the change in second messenger response is a smaller increase in the level of chloride current in the presence of both the chemical compound and the second chemical compound than in the presence of only the second chemical compound. In another embodiment, the second messenger response comprises change in intracellular calcium levels and the change in second messenger response is a smaller increase in the measure of intracellular calcium in the presence of both the chemical compound and the second chemical compound than in the presence of only the second chemical compound. In another embodiment, the second messenger response comprises release of inositol phosphate and the change in second messenger response is a smaller increase in the level of inositol phosphate in the presence of both the chemical compound and the second chemical compound than in the presence of only the second chemical compound.

In one embodiment, the second messenger response comprises activation of MAP kinase and the change in second messenger response is a smaller increase in the level of MAP kinase activation in the presence of both the chemical compound and the secondochemical compound than in the presence of only the second chemical compound. In another embodiment, the second messenger response comprises change in cAMP levels and the change in second messenger response is a smaller change in the level of cAMP in the presence of both the chemical compound and the second chemical compound than in the presence of only the second chemical compound. In another embodiment, the second messenger response comprises release of arachidonic acid and the change in second messenger response is an increase in the level of arachidonic acid levels in the presence of both the chemical compound and the second chemical compound than in the presence of only the second chemical compound. In a further embodiment, the second messenger response comprises GTPγS ligand binding and the change in second messenger is a smaller increase in GTPγS ligand binding in the presence of both the chemical compound and the second chemical compound than in the presence of only the second chemical compound.

In one embodiment, the mammalian SNORF36 receptor is a human SNORF36a receptor or a human SNORF36b receptor. In a further embodiment, the mammalian SNORF36 receptor is a rat SNORF36 receptor. In another embodiment, the cell is an insect cell. In another embodiment, the cell is a mammalian cell. In another embodiment, the mammalian cell is nonneuronal in origin. In another embodiment, the nonneuronal cell is a COS-7 cell, CHO cell, 293 human embryonic kidney cell, NIH-3T3 cell or LM(tk−) cell. In another embodiment, the compound is not previously known to bind to a mammalian SNORF36 receptor.

Further, this invention provides a compound determined by a process according to this invention and a composition, for example, a pharmaceutical composition, which comprises an amount of a mammalian SNORF36 receptor agonist determined to be such by a process according to this invention effective to increase activity of the mammalian SNORF36 receptor and a carrier, for example, a pharmaceutically acceptable carrier. In one embodiment, the mammalian SNORF36 receptor agonist is not previously known.

This invention also provides a composition, for example, a pharmaceutical composition, which comprises an amount of a mammalian SNORF36 receptor antagonist determined to be such by a process according to this invention, effective to reduce activity of the mammalian SNORF36 receptor and a carrier, for example a pharmaceutically acceptable carrier. In one embodiment, the mammalian SNORF36 receptor antagonist is not previously known.

This invention yet further provides a method of screening a plurality of chemical compounds not known to activate a mammalian SNORF36 receptor to identify a compound which activates the mammalian SNORF36 receptor which comprises: (a) contacting cells transfected with and expressing the mammalian SNORF36 receptor with the plurality of compounds not known to activate the mammalian SNORF36 receptor, under conditions permitting activation of the mammalian SNORF36 receptor; (b) determining whether the activity of the mammalian SNORF36 receptor is increased in the presence of one or more of the compounds; and if so (c) separately determining whether the activation of the mammalian SNORF36 receptor is increased by any compound included in the plurality of compounds, so as to thereby identify each compound which activates the mammalian SNORF36 receptor. In one embodiment, the mammalian SNORF36 receptor is a human SNORF36a receptor or a human SNORF36b receptor. In a further embodiment, the mammalian SNORF36 receptor is a rat SNORF36 receptor.

This invention provides a method of screening a plurality of chemical compounds not known to inhibit the activation of a mammalian SNORF36 receptor to identify a compound which inhibits the activation of the mammalian SNORF36 receptor, which comprises: (a) contacting cells transfected with and expressing the mammalian SNORF36 receptor with the plurality of compounds in the presence of a known mammalian SNORF36 receptor agonist, under conditions permitting activation of the mammalian SNORF36 receptor; (b) determining whether the extent or amount of activation of the mammalian SNORF36 receptor is reduced in the presence of one or more of the compounds, relative to the extent or amount of activation of the mammalian SNORF36 receptor in the absence of such one or more compounds; and if so (c) separately determining whether each such compound inhibits activation of the mammalian SNORF36 receptor for each compound included in the plurality of compounds, so as to thereby identify any compound included in such plurality of compounds which inhibits the activation of the mammalian SNORF36 receptor.

In one embodiment, the mammalian SNORF36 receptor is a human SNORF36a receptor or a human SNORF36b receptor. In a further embodiment, the mammalian SNORF36 receptor is a rat SNORF36 receptor. In another embodiment, wherein the cell is a mammalian cell. In another embodiment, the mammalian cell is non-neuronal in origin. In another embodiment, the non-neuronal cell is a COS-7 cell, a 293 human embryonic kidney cell, a LM(tk–) cell or an NIH-3T3 cell.

This invention also provides a composition, for example, a pharmaceutical composition, comprising a compound identified by a method according to this invention in an amount effective to increase mammalian SNORF36 receptor activity and a carrier, for example, a pharmaceutically acceptable carrier.

This invention still further provides a composition, for example, a pharmaceutical composition, comprising a compound identified by a method according to this invention in an amount effective to decrease mammalian SNORF36 receptor activity and a carrier, for example, a pharmaceutically acceptable carrier.

Furthermore, this invention provides a method of treating an abnormality in a subject wherein the abnormality is alleviated by increasing the activity of a mammalian SNORF36 receptor which comprises administering to the subject a compound which is a mammalian SNORF36 receptor agonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, metabolic disorders, a motor coordination disorder, a sensory integration disorder, a motor integration disorder, a dopaminergic function disorder, an appetite disorder, such as anorexia or obesity, a sensory transmission disorder, drug addiction, an olfaction disorder, an autonomic nervous system disorder, pain, neuropsychiatric disorders, affective disorder, migraine, circadian disorders, visual disorders, urinary disorders, blood coagulation-related disorders, developmental disorders, or ischemia-reperfusion injury-related diseases.

In a further embodiment of the present invention, the abnormality is a gestational abnormality, a sleep disorder such as insomnia, jet lag or shift-related conditions, disorders associated with melatonin release, and disorders associated with choroid plexus function.

This invention additionally provides a method of treating an abnormality in a subject wherein the abnormality is alleviated by decreasing the activity of a mammalian SNORF36 receptor which comprises administering to the subject a compound which is a mammalian SNORF36 receptor antagonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, metabolic disorders, a motor coordination disorder, a sensory integration disorder, a motor integration disorder, a dopaminergic function disorder, an appetite disorder, such as anorexia or obesity, a sensory transmission disorder, drug addiction, an olfaction disorder, an autonomic nervous system disorder, pain, neuropsychiatric disorders, affective disorder, migraine, circadian disorders, visual disorders, urinary disorders, blood coagulation-related disorders, developmental disorders, or ischemia-reperfusion injury-related diseases.

In a further embodiment of the present invention, the abnormality is a gestational abnormality, a sleep disorder such as insomnia, jet lag or shift-related conditions, disorders associated with melatonin release, and disorders associated with choroid plexus function.

This invention also provides a process for making a composition of matter which specifically binds to a mammalian SNORF36 receptor which comprises identifying a chemical compound using a process in accordance with this invention and then synthesizing the chemical compound or a novel structural and functional analog or homolog thereof. In one embodiment, the mammalian SNORF36 receptor is a human SNORF36a receptor or a human SNORF36b receptor. In another embodiment; the mammalian SNORF36 receptor is a rat SNORF36 receptor.

This invention further provides a process for preparing a composition, for example a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof. In one embodiment, the mammalian SNORF36 receptor is a human SNORF36a receptor or a human SNORF36b receptor. In another embodiment, the mammalian SNORF36 receptor is a rat SNORF36 receptor.

Thus, once the gene for a targeted receptor subtype is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Identification of a Fragment of the Human SNORF36 Receptor

A human placental genomic phage library (2.75 million recombinants, Stratagene, LaJolla, Calif.) was screened using $^{32}$P-labeled oligonucleotide probes, RW76, RW77, RW96, RW97, RW98 and RW99, designed against transmembrane (TM) domains III, V and VI of the human serotonin 5-HT1$_D$ receptor. The overlapping oligonucleotide probes were labeled with DNA Polymerase I (Klenow Fragment) and [$\alpha$-$^{32}$P]dATP/dCTP.

Hybridization of nitrocellulose filter overlays of the plates was performed at low stringency: 40° C. in a solution containing 25% formamide, 5×SSC (1×SSC is 0.15M sodium chloride, 0.015M sodium citrate), 1×Denhardt's solution (0.02% polyvinylpyrrolindone, 0.02% Ficoll, 0.02% bovine serum albumin), 7 mM Tris and 25 $\mu$g/ml sonicated salmon sperm DNA. The filters were washed at 40° C. in 0.1×SSC containing 0.1% sodium dodecyl sulfate and exposed at −70° C. to Kodak XAR film in the presence of intensifying screens.

A positive signal on plate 10 was isolated on a secondary plating. A 2.3 kb fragment, from a HindIII/XbaI digest of DNA isolated from this positive, was identified by Southern blot analysis, subcloned into pUC18 (Gibco BRL, Gaithersburg, Md.) and used to transform E. Coli XL1 Blue cells (Stratagene, La Jolla, Calif.). Plasmid DNA from one transformant, K39, was sequenced using the Sanger dideoxy nucleotide chain termination method (Sanger et al., 1977) on denatured double-stranded plasmid templates, using Sequenase (US Biochemical Corp., Cleveland, Ohio). Analysis of the sequence of K39 revealed TMs III and IV of a novel GPCR with highest homology to adrenergic receptors.

Isolation of a Full-length Human SNORF36 Receptor

To isolate a full-length SNORF36 receptor, pools of a human hippocampal cDNA library were screened by polymerase chain reaction (PCR) using T604, a K39 specific primer, and either T94, a vector primer, or T603, a K39 specific primer. PCR was performed with Taq DNA Polymerase (Roche Molecular Biochemicals, Indianapolis, Ind.) with the following protocol: 94° C. hold for 5 minutes; 40 cycles of 94° C. for 2 minute, 72° C. for 4 minutes; 10 minute hold at 72° C.; 4° C. hold until the samples are run on a gel. High stringency hybridization of isolated colonies from two positive pools with T605, a K39-specific oligonucleotide probe, and subsequent PCR testing of positive colonies, resulted in the isolation of a single positive clone named TL252. Analysis of the sequence of TL252 revealed that it contained TMI-TMVII, but was missing the NH$_2$ and COOH termini.

To isolate the COOH termini of SNORF36, 3' Rapid Amplification of cDNA Ends (RACE), was performed using the Clontech Marathon cDNA Amplification kit (Clontech, Palo Alto, Calif.). Using the supplier's protocol, Marathon adapters were ligated onto ds cDNA prepared from human hippocampal polyA+ RNA. The initial PCR was performed with the supplier's Adapter Primer 1 and A48, a forward primer from TMVI of TL252. 2 $\mu$ls of this initial PCR reaction was re-amplified using the Adaptor Primer 2 and A49, a forward primer from TMVI. PCR was performed with Advantage Klentaq Polymerase (Clontech, Palo Alto, Calif.) under the following conditions: 30 seconds at 94° C.; 30 cycles of 94° C. for 30 seconds, 68° C. 4 minutes; and 4° C. hold until the products were ready for analysis. A 1.5 kb fragment was isolated from an agarose TAE gel using the QIAQUICK gel extraction kit (QIAGEN, Chatsworth, Calif.) and subcloned into the TA cloning vector (Invitrogen, San Diego, Calif.). One transformant, AB25, was sequenced using the ABI Big Dye cycle sequencing protocol and ABI 377 sequencers (ABI, Foster City, Calif.). Sequences were analyzed using the Wisconsin Package (GCG, Genetics Computer Group, Madison, Wis.). Analysis of the sequence of AB25 revealed the COOH terminus and a stop codon approximately 350 bp downstream from TMVII.

To look for a full-length SNORF36 cDNA, pools of a human hippocampal cDNA library were screened by PCP with TL252-specific primers BB788 and BB789 using the Expand Long Template PCR System (Boehringer-Mannheim, Indianapolis, Ind.). Conditions for PCR amplification were as follows: 94° C. hold for 5 minutes; 40 cycles of 94° C. for 30 seconds, 68° C. for 2 minutes; 68° C. hold for 5 minutes; 4° C. hold until ready for agarose gel electrophoresis. This screen yielded three positive pools. Subsequent high-stringency hybridization of isolated colonies from two of these pools using a [$\gamma$-$^{32}$P]-ATP-labeled SNORF36-specific probe (BB791) resulted in the identification of 2 positive individual colonies, 260.13.1 and 243.33.3. Sequencing of these clones revealed that they were identical and were full-length at the 3' end. However, while these clones contained some sequence upstream of TMI, they did not contain the initiating methionine. In addition, these clones both contained an 11 amino acid insert in the first intracellular loop that was not present in TL252.

To identify the $NH_2$ terminal sequence, 5'RACE was performed on Marathon-Ready human hippocampal cDNA (Clontech, Palo Alto, Calif.) according to the Marathon cDNA Amplification Kit protocol. The initial PCR was performed with the supplier's Adapter Primer 1 and BB798 a reverse primer from the second intracellular loop of 260.13.1. One up of this initial PCR reaction was re-amplified using the Adaptor Primer 2 and BB797, a reverse primer from TMI. PCR was performed with Advantage Klentaq Polymerase (Clontech, Palo Alto, Calif.) under the following conditions: 30 seconds at 94° C.; 5 cycles of 94° C. for 30 seconds and 72° C. for 3 minutes; 5 is cycles of 94° C. for 30 seconds and 70° C. for 3 minutes; 23 cycles (initial PCR) or 20 cycles (nested PCR) of 94° C. for 30 seconds and 68° C. for 3 minutes; 68° C. hold for 7 minutes, and 4° C. hold until the products were ready for analysis. A 500 bp fragment was isolated from a 1% agarose TAE gel using the QIAQUICK gel extraction kit (QIAGEN, Chatsworth, Calif.) and sequenced using ABI 377 sequencers and BigDye termination cycle sequencing as described above. Analysis of this sequence revealed the $NH_2$ terminus including 2 methionines 71 and 52 amino acids upstream from TMI.

A full-length cDNA clone for SNORF36a (without the 11 amino acid insert) was constructed as follows. The 5' end of the cDNA was amplified from hippocampal and pituitary cDNAs using the Expand Long Template PCR System (Roche Molecular Biochemicals, Indianapolis, Ind.) and BB812, a forward primer from the 5'UT also incorporating a BamHI restriction site, and BB813, a reverse primer from the third extracellular loop. Conditions for PCR amplification were as follows: 94° C. hold for 5 minutes; 37 cycles of 94° C. for 30 seconds; 68° C. for 2.5 minutes; 68° C. hold for 7 minutes; 4° C. hold until ready for agarose gel electrophoresis. 1050 bp bands from 9 independent PCR reactions were cut from a 1% agarose gel, purified using the QIAQUICK gel extraction kit (QIAGEN, Chatsworth, Calif.), subcloned into the TA cloning vector (Invitrogen, San Diego, Calif.) and sequenced using the ABI Big Dye cycle sequencing protocol and ABI 377 sequencers (ABI, Foster City, Calif.). Analysis of these sequences revealed the presence of an allelic variation. Nucleotide 39 (FIGS. 1A–C and 3A–C) is either an adenine or a guanine. One of these PCR products, F9, matched the consensus sequence with the exception of a single conservative nucleotide change. A 1021 bp BamHI/BglI fragment from F9 was then ligated along with a 1180 bp BglI/EcoRI fragment from the human hippocampal library pool 260.13.1 into a BamHI/EcoRI-cut pcDNA3.1 (Invitrogen, San DCego, Calif.), and this construct was named BO108. The single point mutation introduced by the PCR fragment was corrected with the QuikChange Site-Directed Mutagenesis Kit (Stratagene, LaJolla, Calif.) using BB926 and BB927 and the manufacturer's instructions. The resulting SNORF36a construct, BO109, was sequenced on both strands as described above. This clone was renamed pcDNA3.1-hSNORF36a-f. A full-length clone for SNORF36b (with the 11 amino acid insert) was constructed as follows. A 1260 bp fragment was obtained by amplifying BO108 with BB796, a forward primer in TMI and BB936, a reverse primer at the stop codon also incorporating a HindIII site, with the following protocol: 94° C. hold for 5 minutes; 32 cycles of 94° C. for 30 seconds; 68° C. for 2.5 minutes; 68° C. hold for 7 minutes; 4° C. hold until ready for agarose gel electrophoresis. A 1130 bp NspI/HindIII fragment from this PCR product and a 390 bp BamHI/NspI fragment from K81, one of the PCR products from the BB812-BB813 PCR described above, was ligated into a BarnHI/HindIII-cut pcDNA3.1 (Invitrogen, San Diego, Calif.). The resulting SNORF36b construct, BO110, was sequenced on both strands as described above. This clone was renamed pcDNA3.1-hSNORF36b-f.

Isolation of a Fragment of the Rat Homologue of SNORF36

To obtain a fragment of the rat homologue of SNORF-36, 100 ng of rat genomic DNA (Clontech, Palo Alto, Calif.) was amplified with BB788, a forward PCR primer corresponding to TMIII of human SNORF36 and BB1097, a reverse primer corresponding to TMV of human SNORF36. PCR was performed with the Expand Long Template PCR System (Roche Molecular Biochemicals) under the following conditions: 30 seconds at 94° C., 45 seconds at 45° C. or 50° C., 1.5 minutes at 68° C. for 40 cycles, with a pre- and post-incubation of 5 minutes at 94° C. and 7 minutes at 68° C. respectively. Bands of 800 bp from 7 independent PCR reactions were isolated from a TAE gel, purified using the QIAQUICK gel extraction kit (QIAGEN, Chatsworth, Calif.), and sequenced on both strands as described above. Analysis of the sequence revealed an intron in the second extracellular loop. The consensus of the 7 sequences was used to design forward and reverse PCR primers (BB1182, also incorporating a BamHI restriction site, and BB1183, also incorporating a HindIII site) which were used to amplify a band from rat spinal cord cDNA using the following conditions: 30 seconds at 94° C., 30 seconds at 64° C., 1.5 minutes at 68° C. for 37 cycles, with a pre- and post-incubation of 5 minutes at 94° C. and 7 minutes at 68° C. respectively. Products from 3 independent PCR reactions were digested with BamHI and HindIII and fragments of 250 bp were gel-purified and ligated into the expression vector pEXJ.T3T7. One transformant from each PCR reaction was sequenced as above. The nucleotide sequences of two products were identical to the consensus and one, KO56, was renamed pEXJ-rSNORF36-p.

Isolation of a Full-length Rat SNORF36 Receptor

To look for the full-length rat SNORF36 cDNA, pools of a rat spinal cord cDNA library were screened by PCR with BB1182, a forward primer from TMIII of the rat SNORF36 fragment, and BB1183, a reverse primer from TMV of the rat SNORF36 fragment. PCR was performed using the Expand Long Template PCR System (Roche Molecular Biochemicals, Indianapolis, Ind.) under the following conditions: 94° C. hold for 5 minutes; 40 cycles of 94° C. for 30 seconds, 68° C. for 5 minutes; 68° C. hold for 7 minutes; 4° C. hold until ready for agarose gel electrophoresis. This screen yielded 2 positive pools. Subsequent high-stringency hybridization of isolated colonies from 1 of these pools using a [$\gamma$-$^{32}$P]-ATP-labeled rat SNORF36-specific probe (BB1298) resulted in the identification of a positive individual colony, N323.16.1F, renamed KO109. Sequencing of KO109 revealed that it contained an insert of 2.6 kb, including an open reading frame of 1422 nucleotides, 148 nucleotides of 5'UT and approximately 1000 nucleotides of 3'UT. This clone was renamed pEXJ.T7-rSNORF36-f.

Isolation of Other Species Homologs of SNORF36 Receptor cDNA

A nucleic acid sequence encoding a SNORF36 receptor cDNA from other species may be isolated using standard molecular biology techniques and approaches such as those described below:

Approach #1: A genomic library (e.g., cosmid, phage, P1, BAC, YAC) generated from the species of interest may be screened with a $^{32}$P-labeled oligonucleotide probe corresponding to a fragment of the human or rat SNORF36 receptors whose sequence is shown in FIGS. 1A–1C, 3A–3C, 5 or 9A–9C to isolate a genomic clone. The full-length sequence may be obtained by sequencing this genomic clone. If one or more introns are present in the gene, the full-length intronless gene may be obtained from cDNA using standard molecular biology techniques. For example, a forward PCR primer designed in the 5'UT and a reverse PCR primer designed in the 3'UT may be used to amplify a full-length, intronless receptor from cDNA. Standard molecular biology techniques could be used to subclone this gene into a mammalian expression vector.

Approach #2: Standard molecular biology techniques may be used to screen commercial cDNA phage libraries of the species of interest by hybridization under reduced stringency with a $^{32}$P-labeled oligonucleotide probe corresponding to a fragment of the sequences shown in FIGS. 1A–1C, 3A–3C, 5 or 9A–9C. One may isolate a full-length SNORF36 receptor by obtaining a plaque purified clone from the lambda libraries and then subjecting the clone to direct DNA sequencing. Alternatively, standard molecular biology techniques could be used to screen cDNA plasmid libraries by PCR amplification of library pools using primers designed against a partial species homolog sequence. A full-length clone may be isolated by Southern hybridization of colony lifts of positive pools with a $^{32}$P-oligonucleotide probe.

Approach #3: 3' and 5' RACE may be utilized to generate PCR products from cDNA derived from the species of interest expressing SNORF36 which contain the additional sequence of SNORF36. These RACE PCR products may then be sequenced to determine the additional sequence. This new sequence is then used to design a forward PCR primer in the 5'UT and a reverse primer in the 3'UT. These primers are then used to amplify a full-length SNORF36 clone from cDNA.

Examples of other species include, but are not limited to, mouse, dog, monkey, hamster and guinea pig.

Primers and probes used in the identification of SNORF36:

RW76:
5-CATCGCCCTCGACGTGCTGTGCTGCACCTC ATCCATCT TGCACCT-3' (SEQ ID NO: 9)

RW77:
5'-CATGGACAGGTCGCGCTACCGCGTGTCCA CGTTCTACC TACTCCA-3' (SEQ ID NO: 10)

RW96:
5'-GGCATCATCATGGGCACCTTCATCCTCTGC TGGCTGCC CTTCTTC-3' (SEQ ID NO: 11)

RW97:
5'-GCAGAAGGGCAGAACAAGAGCCACGATG AAGAAGGGCA GCCAGCA-3' (SEQ ID NO: 12)

RW98:
5'-TGGCTGTCATCGGACATCACTTGTTGCACT GCCTCCAT CCTGCAC-3' (SEQ ID NO: 13)

RW99:
5'-GTAGCGGTCCAGGGCGATGACACAGAGGT GCAGGATGG AGGCAGT-3' (SEQ ID NO: 14)

T604: 5'-CCAGCCGAAGAAGGGTGGCAGACTCCA-3' (SEQ ID NO: 15)

T94: 5'-CTTCTAGGCCTGTACGGAAGTGTTA-3' (SEQ ID NO: 16)

T603: 5'-GCACAGGCTGCGAGTTCTATTCCTT-3' (SEQ ID NO: 17)

T605:
5'-CTGGTAATCACACACCCGCTGGCCACCTTT GGTGTGGC GTCCAAG-3' (SEQ ID NO: 18)

A48: 5'-AGATCATGCTGCTGGTCATCCTCC-3' (SEQ ID NO: 19)

A49: 5'-TCGTGCTCTCCTGGGCTCCCT-3' (SEQ ID NO: 20)

BB788: 5'-TCCTCCATGATCACCCTGACGGC-3' (SEQ ID NO: 21)

BB789: 5'-TCTGGAGAGCCCGTCCTGTCTCC-3' (SEQ ID NO: 22)

BB791:
5'-CGGCCGTGCGTGCCTACACCATGCTTCTCT GCTGCTTC GTGTTCTTCC-3' (SEQ ID NO: 23)

BB798: 5'-TTGGACGCCACACCAAAGGTGGCC-3' (SEQ ID NO: 24)

BB797: 5'-GGTATAGATGACCGTCAGGTTGCC-3' (SEQ ID NO: 25)

BB812:
5'-CGAACAGGATCCTCTCTGTGGGCTCGAGC AAGGACC-3' (SEQ ID NO: 26)

BB813: 5'-ACGTGTGCGTACCCAGCAAAGGCC-3' (SEQ ID NO: 27)

BB926:
5'-GTCCCACAGCACCTGGGACTTGGGCTGC-3' (SEQ ID NO: 28)

BB927:
5'-GCAGCCCAAGTCCCAGGTGCTGTGGGAC-3' (SEQ ID NO: 29)

BB796: 5'-GGCAACCTGACGGTCATCTATACC-3' (SEQ ID NO: 30)

BB936:
5'-CAGCATAAGCTTCCAGTGGGCGTCCTACAT CCTGG-3' (SEQ ID NO: 31)

BB1097: 5'-CAGTAGATGATGATAAGCAGAGG-3' (SEQ ID NO: 32)

BB1182:
    5'-CGAACAGGATCCCATAGCCATGGACCGCTATCTGG-3' (SEQ ID NO: 33)
BB1183:
    5'-CCTAGCAAGCTTGAGGAAGAAGACAAAGC AGAAGAGC-3' (SEQ ID NO: 34)
BB1298:
    5'-CGGACGGCACTAGTCCTGCTAGGTGTCTG GCTCTATGCCCTGG CCTGG-3' (SEQ ID NO: 35)

Host Cells

A broad variety of host cells can be used to study heterologously expressed proteins. These cells include, but are not limited to, mammalian cell lines such as: COS-7, CHO, LM(tk–), HEK293, etc.; insect cell lines such as Sf9, Sf21, Trichoplusia ni 5B-4, etc.; amphibian cells such as Xenopus oocytes; assorted yeast strains; assorted bacterial cell strains; and others. Culture conditions for each of these cell types are specific and are known to those familiar with the art. The cells used to express human SNORF36 receptor were COS-7 and Human embryonic kidney (HEK) 293 cells.

COS-7 cells are grown on 150 mm plates in DMEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of COS-7 cells are trypsinized and split 1:6 every 3–4 days.

HEK293 cells are grown on 150 mm plates in DMEM with supplements (10% bovine calf serum, 4 mM glutamine, 100 units/ml penicillin/100 µg/ml streptomycin) at 37° C., 5% $CO_2$. Stock plates of 293 cells are trypsinized and split 1:6 every 3–4 days.

Transient Expression

DNA encoding proteins to be studied can be transiently expressed in a variety of mammalian, insect, amphibian and other cell lines by several methods, such as, calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed.

A typical protocol for the DEAE-dextran method as applied to Cos-7 and HEK293 cells is described as follows. Cells to be used for transfection are split 24 hours prior to the transfection to provide flasks which are 70–80% confluent at the time of transfection. Briefly, 8 µg of receptor DNA plus 8 µg of any additional DNA needed (e.g. $G_\alpha$ protein expression vector, reporter construct, antibiotic resistance marker, mock vector, etc.) are added to 9 ml of complete DMEM plus DEAE-dextran mixture (10 mg/ml in PBS). Cells plated into a T225 flask (sub-confluent) are washed once with PBS and the DNA mixture is added to each flask. The cells are allowed to incubate for 30 minutes at 37° C., 5% $CO_2$. Following the incubation, 36 ml of complete DMEM with 80 µM chloroquine is added to each flask and allowed to incubate an additional 3 hours. The medium is then aspirated and 24 ml of complete medium containing 10% DMSO for exactly 2 minutes and then aspirated. The cells are then washed 2 times with PBS and 30 ml of complete DMEM added to each flask. The cells are then allowed to incubate over night. The next day the cells are harvested by trypsinization and reseeded into 96 well plates.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin. For purposes of studies concerning the receptor of this invention, stable expression of a heterologous receptor protein is typically carrier out in, mammalian cells including but not necessarily restricted to, CHO, HEK293, LM(tk–), etc. In addition native cell lines that naturally carry and express the nucleic acid sequences for the receptor may be used without the need to engineer the receptor complement.

Functional Assays

Cells expressing the receptor DNA of this invention may be used to screen for ligands to said receptor using functional assays. Once a ligand is identified the same assays may be used to identify agonists or antagonists of the receptor that may be employed for a variety of therapeutic purposes. It is well known to those in the art that the over-expression of a GPCR can result in the constitutive activation of intracellular signaling pathways. In the same manner, over-expression of the SNORF36a receptor in any cell line as described above, can result in the activation of the functional responses described below, and any of the assays herein described can be used to screen for agonist, partial agonist, inverse agonist and antagonist ligands of the SNORF36 receptor.

A wide spectrum of assays can be employed to screen for the presence of SNORF36 receptor ligands. These assays range from traditional measurements of total inositol phosphate accumulation, cAMP levels, intracellular calcium mobilization, and potassium currents, for example; to systems measuring these same second messengers but which have been modified or adapted to be of higher throughput, more generic and more sensitive; to cell based assays reporting more general cellular events resulting from receptor activation such as metabolic changes, differentiation, cell division/proliferation. Description of several such assays follow.

Cyclic AMP (cAMP) Assay

The receptor-mediated stimulation or inhibition of cyclic AMP (cAMP) formation may be assayed in cells expressing the receptors. Cells are plated in 96-well plates or other vessels and preincubated in a buffer such as HEPES buffered saline (NaCl (150 mM), $CaCl_2$ (1 mM), KCl (5 mM), glucose (10 mM)) supplemented with a phosphodiesterase inhibitor such as 5mM theophylline, with or without protease inhibitor cocktail (For example, a typical inhibitor cocktail contains 2 µg/ml aprotinin, 0.5 mg/ml leupeptin, and 10 µg/ml phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

Arachidonic Acid Release Assay

Cells expressing the receptor are seeded into 96 well plates or other vessels and grown for 3 days in medium with supplements. $^3$H-arachidonic acid (specific activity=0.75

μCi/ml) is delivered as a 100 μL aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 μL. Cells are incubated for 30 min at 37° C., 5% $CO_2$. Supernatants are transferred to a microtiter plate and evaporated to dryness at 75° C. in a vacuum oven. Samples are then dissolved and resuspended in 25 μL distilled water. Scintillant (300 μL) is added to each well and samples are counted for $^3H$ in a Trilux plate reader. Data are analyzed using nonlinear regression and statistical techniques available in the GraphPAD Prism package (San Diego, Calif.).

Intracellular Calcium Mobilization Assays

The intracellular free calcium concentration may be measured by microspectrofluorimetry using the fluorescent indicator dye Fura-2/AM (Bush et al, 1991). Cells expressing the receptor are seeded onto a 35 mm culture dish containing a glass coverslip insert and allowed to adhere overnight. Cells are then washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques. In another method, the measurement of intracellular calcium can also be performed on a 96-well (or higher) format and with alternative calcium-sensitive indicators, preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular calcium concentration can be measured by a luminometer, or a fluorescence imager; a preferred example of this is the fluorescence imager plate reader (FLIPR).

Cells expressing the receptor of interest are plated into clear, flat-bottom, black-wall 96-well plates (Costar) at a density of 30,000–80,000 cells per well and allowed to incubate over night at 5% $CO_2$, 37° C. The growth medium is aspirated and 100 μl of dye loading medium is added to each well. The loading medium contains: Hank's BSS (without phenol red)(Gibco), 20 mM HEPES (Sigma), 0.1% BSA (Sigma), dye/pluronic acid mixture (e.g. 1 mM Flou-3, AM (Molecular Probes), 10% pluronic acid (Molecular Probes); (mixed immediately before use), and 2.5 mM probenecid (Sigma) (prepared fresh)). The cells are allowed to incubate for about 1 hour at 5% $CO_2$, 37° C.

During the dye loading incubation the compound plate is prepared. The compounds are diluted in wash buffer (Hank's BSS without phenol red), 20 mM HEPES, 2.5 mM probenecid to a 3×final concentration and aliquoted into a clear v-bottom plate (Nunc). Following the incubation the cells are washed to remove the excess dye. A Denley plate washer is used to gently wash the cells 4 times and leave a 100 μl final volume of wash buffer in each well. The cell plate is placed in the center tray and the compound plate is placed in the right tray of the FLIPR. The FLIPR software is setup for the experiment, the experiment is run and the data are collected. The data are then analyzed using an excel spreadsheet program.

Antagonist ligands are identified by the inhibition of the signal elicited by agonist ligands.

The intracellular free calcium ($Ca^{+2}$) concentration may be measured by the Fluorescence Imager Plate Reader (FLIPR™).

Cells transfected with appropriate DNA as described earlier were plated into clear, flat-bottom, black-wall 96-well plates (Costar) at a density of 80,000–150,000 cells per well and allowed to incubate for 24 hr at 5% $CO_2$, 37° C. Whenever necessary, the cells were placed in a waterbath maintained at 37° C. and were exposed to a lamp light (50W) placed at a distance of approximately 30 cm, 90 to 120 min before the imaging. The growth medium was aspirated and 100 μl of loading medium containing fluo-3 dye was added to each well 60 min before the imaging. The loading medium contained: Hank's BSS (without phenol red) (Gibco), 20 mM HEPES (Sigma), 0.1 or 1% BSA (Sigma), dye/pluronic acid mixture (e.g. 1 mM Flou-3, AM (Molecular Probes) and 10% pluronic acid (Molecular Probes) mixed immediately before use), and 2.5 mM probenecid (Sigma) (prepared fresh). The cells were allowed to incubate for about 1 hour at 5% $CO_2$, 37° C.

Before or during the incubation of cells with the dye-loading medium, the test compound plate was prepared. Since retinoids are chemically unstable and can undergo rapid photoisomerization (Hu et al., 1994), care was taken to weigh, dissolve and prepare appropriate concentrations of the test compounds under photographic darkroom lights. The test compounds were diluted in wash buffer (Hank's BSS (without phenol red), 20 mM HEPES, 2.5 mM probenecid) to a 4×final concentration and aliquoted into a clear v-bottom plate (Nunc). The test compounds were protected from light till their addition to cells. Following the incubation with the dye-loading medium, the cells were washed to remove the excess dye. A Denley plate washer was used to gently wash the cells 4 times and leave a 100 μl final volume of wash buffer in each well. The cell plate was placed in the center tray and the test compound plate was placed in the right tray of the FLIPR. The FLIPR software was setup for the experiment, the experiment was run and the data were collected. For the agonist experiment, the sampling rate in the FLIPR was every 1 sec for the first minute and every 2 sec for the next two minutes. In this paradigm, the test compound was added after recording base line for the first 10 sec. For the antagonist experiment, the sampling rate in the FLIPR was every 1 sec for the first minute, every 6 sec for the next 5 minutes, every 1 sec for the next one minute followed by every 2 sec next two minutes. To evaluate the antagonistic activity, the test compound was added to the cells 10 sec after commencing the recording and the agonist was added at 310 sec of the recording. Baseline subtraction and negative control corrections were performed on the traces. The collected data were then analyzed using an Excel spreadsheet program.

Inositol Phosphate Assay

Human SNORF36a receptor-mediated activation of the inositol phosphate (IP) second messenger pathways was assessed by radiometric measurement of IP products.

For example, in a 96 well microplate format assay, cells are plated at a density of 70,000 cells per well and allowed to incubate for 24 hours. The cells are then labeled with 0.5 μCi [$^3H$]myo-inositol overnight at 37° C., 5% $CO_2$. Immediately before the assay, the medium is removed and replaced with 90 μL of PBS containing 10 mM LiCl. The plates are then incubated for 15 min at 37° C., 5% $CO_2$. Following the incubation, the cells are challenged with agonist (10 μl/well; 10×concentration) for 30 min at 37° C., 5% $CO_2$. The challenge is terminated by the addition of 100 μL of 50% v/v trichloroacetic acid, followed by incubation at 40° C. for greater than 30 minutes. Total IPs are isolated from the lysate by ion exchange chromatography. Briefly, the lysed contents of the wells are transferred to a Multiscreen HV filter plate (Millipore) containing Dowex AG1-X8 (200–400 mesh, formate form). The filter plates are prepared adding 100 μL of Dowex AG1-X8 suspension (50% v/v, water: resin) to each well. The filter plates are placed on a vacuum manifold to wash or elute the resin bed. Each well is first washed 2 times with 200 μl of 5 mM myo-inositol. Total [$^3$H]inositol phosphates are eluted with 75 μl of 1.2 M ammonium formate/0.1 M formic acid solution into 96-well plates. 200 μL of scintillation cocktail is added to each well, and the radioactivity is determined by liquid scintillation counting.

Cells were plated at a density of 70,000 cells per well and allowed to incubate for 24 hours. The cells were then labeled with 0.5 μCi [$^3$H]myo-inositol overnight at 37° C., 5% $CO_2$. Immediately before the assay, the medium was removed and replaced with 180 μL of Phosphate-Buffered Saline (PBS) containing 10 mM LiCl. The plates were then incubated for 20 min at 37° C., 5% $CO_2$. Following the incubation, the cells were challenged with agonist (20 μl/well; 10×concentration) for 30 min at 37° C. and were simultaneously either exposed or not to a lamp light (50W) placed at approximately 30 cm distance from the cells. The challenge was terminated by the addition of 100 μL of 5% v/v trichloroacetic acid, followed by incubation at 4° C. for greater than 30 minutes. Total IPs were isolated from the lysate by ion exchange chromatography. Briefly, the lysed contents of the wells were transferred to a Multiscreen HV filter plate (Millipore) containing Dowex AG1-X8 (200–400 mesh, formate form). The filter plates were prepared adding 100 μL of Dowex AG1-X8 suspension (50% v/v, water: resin) to each well. The filter plates were placed on a vacuum manifold to wash or elute the resin bed. Each well was first washed 2 times with 200 μl of 5 mM myo-inositol. Total [$^3$H]inositol phosphates were eluted with 75 μl of 1.2M ammonium formate/0.1M formic acid solution into 96-well plates. 200 μL of scintillation cocktail was added to each well, and the radioactivity was determined by liquid scintillation counting.

GTPγS Functional Assay

Membranes from cells expressing the receptor are suspended in assay buffer (e.g., 50 mM Tris, 100 mM NaCl, 5 mM $MgCl_2$, 10 μM GDP, pH 7.4) with or without rotease inhibitors (e.g., 0.1% bacitracin). Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus unlabeled GTPγS (final concentration=100 μM). Final membrane protein concentration≈90 μg/ml. Samples are incubated in the presence or absence of test compounds for 30 min. at room temperature, then filtered on a Millipore vacuum manifold and washed three times with cold (4° C.) assay buffer. Samples collected in the filter plate are treated with scintiliant and counted for $^{35}$S in a Trilux (Wallac) liquid scintillation counter. It is expected that optimal results are obtained when the receptor membrane preparation is derived from an appropriately engineered heterologous expression system, i.e., an expression system resulting in high levels of expression of the receptor and/or expressing G-proteins having high turnover rates (for the exchange of GDP for GTP). GTPγS assays are well-known to those skilled in the art, and it is contemplated that variations on the method described above, such as are described by Tian et al. (1994) or Lazareno and Birdsall (1993), may be used.

Microphysiometric Assay

Because cellular metabolism is intricately involved in a broad range of cellular events (including receptor activation of multiple messenger pathways), the use of mlcrophysiometric measurements of cell metabolism can in principle provide a generic assay of cellular activity arising from the activation of any orphan receptor regardless of the specifics of the receptor's signaling pathway.

General guidelines for transient receptor expression, cell preparation and microphysiometric recording are described elsewhere (Salon, J. A. and Owicki, J. A., 1996). Typically cells expressing receptors are harvested and seeded at 3×10$^5$ cells per microphysiometer capsule in complete media 24 hours prior to an experiment. The media is replaced with serum free media 16 hours prior to recording to minimize non-specific metabolic stimulation by assorted and ill-defined serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 μl/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 μM final concentration.

Follow up experiments to examine dose-dependency of active compounds are then done by sequentially challenging the cells with a drug concentration range that exceeds the amount needed to generate responses ranging from threshold to maximal levels. Ligand samples are then washed out and the acidification rates reported are expressed as a percentage increase of the peak response over the baseline rate observed just prior to challenge.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$, and samples are transferred to ice. An aliquot is spotted onto Whatman P81 chromatography paper, which retains the phosphorylated protein. The chromatography paper is washed and counted for $^{32}P$ in a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}P$ by liquid scintillation counting.

Cell Proliferation Assay

Receptor activation of the orphan receptor may lead to a mitogenic or proliferative response which can be monitored via $^3$H-thymidine uptake. When cultured cells are incubated with $^3$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. 24 hrs later, the cells are incubated with $^3$H-thymidine at specific activities ranging from 1 to 10 $\mu$Ci/ml for 2–6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^3$H by liquid scintillation counting.

Alternatively, cell proliferation can be assayed by measuring the expression of an endogenous or heterologous gene product, expressed by the cell line used to transfect the orphan receptor, which can be detected by methods such as, but not limited to, florescence intensity, enzymatic activity, immunoreactivity, DNA hybridization, polymerase chain reaction, etc.

Promiscuous Second Messenger Assays

It is not possible to predict, a priori and based solely upon the GPCR sequence, which of the cell's many different signaling pathways any given orphan receptor will naturally use. It is possible, however, to coax receptors of different functional classes to signal through a pre-selected pathway through the use of promiscuous $G_\alpha$ subunits. For example, by providing a cell based receptor assay system with an endogenously supplied promiscuous $G_\alpha$ subunit such as $G_{\alpha 15}$ or $G_{\alpha 16}$ or a chimeric $G_\alpha$ subunit such as $G_{\alpha qz}$, a GPCR, which might normally prefer to couple through a specific signaling pathway (e.g., $G_s$, $G_i$, $G_q$, $G_o$, etc.), can be made to couple through the pathway defined by the promiscuous $G_\alpha$ subunit and upon agonist activation produce the second messenger associated with that subunit's pathway. In the case of $G_{\alpha 15}$, $G_{\alpha 16}$ and/or $G_{\alpha qz}$ this would involve activation of the $G_q$ pathway and production of the second messenger $IP_3$. Through the use of similar strategies and tools, it is possible to bias receptor signaling through pathways producing other second messengers such as $Ca^{++}$, cAMP, and $K^+$ currents, for example (Milligan, 1999).

It follows that the promiscuous interaction of the exogenously supplied $G_\alpha$ subunit with the orphan receptor alleviates the need to carry out a different assay for each possible signaling pathway and increases the chances of detecting a functional signal upon receptor activation.

Methods for Recording Currents in Xenopus Oocytes

Oocytes are harvested from *Xenopus laevis* and injected with mRNA transcripts as previously described (Quick and Lester, 1994; Smith et al., 1997). The test receptor of this invention and Gα subunit RNA transcripts are synthesized using the T7 polymerase ("Message Machine," Ambion) from linearized plasmids or PCR products containing the complete coding region of the genes. Oocytes are injected with 10 ng synthetic receptor RNA and incubated for 3–8 days at 17 degrees. Three to eight hours prior to recording, oocytes are injected with 500 pg promiscuous Gα subunits mRNA in order to observe coupling to $Ca^{++}$ activated $Cl^-$ currents. Dual electrode voltage clamp (Axon Instruments Inc.) is performed using 3 M KCl-filled glass microelectrodes having resistances of 1–2 MOhm. Unless otherwise specified, oocytes are voltage clamped at a holding potential of −80 mV. During recordings, oocytes are bathed in continuously flowing (1–3 ml/min) medium containing 96 mM NaCl, 2 mM KCl, 1.8 mM $CaCl_2$, 1 mM $MgCl_2$, and 5 miM HEPES, pH 7.5 (ND96). Drugs are applied-either by local perfusion from a 10 $\mu$l glass capillary tube fixed at a distance of 0.5 mm from the oocyte, or by switching from a series of gravity fed perfusion lines.

Other oocytes may be injected with a mixture of receptor mRNAs and synthetic mRNA encoding the genes for G-protein-activated inward rectifier channels (GIRK1 and GIRK4, U.S. Pat. Nos. 5,734,021 and 5,728,535 or GIRK1 and GIRK2) or any other appropriate combinations (see, e.g., Inanobe et al., 1999). Genes encoding G-protein inwardly rectifying $K^+$ (GIRK) channels 1, 2 and 4 (GIRK1, GIRK2, and GIRK4) may be obtained by PCR using the published sequences (Kubo et al., 1993; Dascal et al., 1993; Krapivinsky et al., 1995 and 1995b) to derive appropriate 5' and 3' primers. Human heart or brain cDNA may be used as template together with appropriate primers.

Heterologous expression of GPCRs in Xenopus oocytes has been widely used to determine the identity of signaling pathways activated by agonisL stimulation (Gundersen et al., 1983; Takahashi et al., 1987). Activation of the phospholipase C (PLC) pathway is assayed by applying test compound in ND96 solution to oocytes previously injected with mRNA for the mammalian orphan receptor (with or without promiscuous G proteins) and observing inward currents at a holding potential of −80 mV. The appearance of currents that reverse at −25 mV and display other properties of the $Ca^{++}$-activated $Cl^-$ chloride) channel is indicative of mammalian receptor-activation of PLC and release of IP3 and intracellular $Ca^{++}$. Such activity is exhibited by GPCRs that couple to $G_q$ or $G_{11}$.

Measurement of inwardly rectifying $K^+$ (potassium) channel (GIRK) activity may be monitored in oocytes that have been co-injected with mRNAs encoding the mammalian orphan receptor plus GIRK subunits. GIRK gene products co-assemble to form a G-protein activated potassium channel known LO be activated (i.e., stimulated) by a number of GPCRs that couple to $G_i$ or $G_o$ (Kubo et al., 1993; Dascal et al., 1993). Oocytes expressing the mammalian orphan receptor plus the GIRK subunits are tested for test compound responsivity by measuring $K^+$ currents in elevated $K^+$ solution contain ng 49 mM $K^+$.

In the present invention, oocytes were harvested from *Xenopus laevis* and injected with mRNA transcripts as previously described (Quick and Lester, 1994; Smith et al.,1997). SNORF36a RNA transcripts were synthesized using the T7 polymerase ("Message Machine", Ambion) from the plasmid BO109 linearized with NotI. Oocytes were injected with 5–25 ng synthetic RNA and incubated for 3–8 days at 17° C. Dual electrode voltage clamp (Axon Instruments Inc.) was performed using 3 M KCl-filled glass microelectrodes having resistances of 1–2 MOhm. Unless otherwise specified, oocytes were voltage clamped at a holding potential of −80 mV. During recordings, oocytes were bathed in continuously flowing (1–3 ml/min) medium containing 96 mM NaCl, 2 mM KCl, 1.8 mM $CaCl_2$, 1 mM $MgCl_2$, 5 mM HEPES, pH 7.5 (ND96), and the appropriate ligand.

Experiments were carried out under minimal light conditions which required compound weighing, final dilutions and oocyte recordings to be performed under photographic darkroom lights ("Brightlab Junior" safelight). In some cases, the ligands were briefly exposed to room light (5–10 min.) during the weighing procedure. For eliciting physiological responses from oocytes, the light stimulus was a 60 W tungsten lamp set at a distance of 30 cm from the oocyte. Drugs were applied either by superfusion, switcning from a series of gravity fed perfusior. lines, or by local perfusion from a 10 µl glass capillary tube fixed at a distance of 0.5 mm from the oocyte. Experiments were carried out at room temperature. All values are expressed as mean±standard error of the mean.

Membrane Preparations

Cell membranes expressing the receptor protein of this invention are useful for certain types of assays including but not restricted to ligand binding assays, GTP-g-S binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris HCl, mM EDTA, pH 7.4 at 4° C.). The resulting crude cell lysate is cleared of cell debris by low speed centrifugation at 200×g for 5 min at 4° C. The cleared supernatant is then centrifuged at 40,000×g for 20 min at 4° C., and the resulting membrane pellet is washed by suspending in ice cold buffer and repeating the high speed centrifugation step. The final washed membrane pellet is resuspended in assay buffer. Protein concentrations are determined by the method of Bradford (1976) using bovine serum albumin as a standard. The membranes may be used immediately or frozen for later use.

Generation of Baculovirus

The coding region of DNA encoding the human receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into 2×10⁶ *Spodoptera frugiperda* insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Localization of mRNA Coding for Human and Rat SNORF36

Quantitative RT-PCR Using a Fluorogenic Probe with Real Time Detection: Quantitative RT-PCR using fluorogenic probes and a panel of mRNA extracted from human and total RNA extracted from rat tissue was used to characterize the localization of rat and human SNORF36.

This assay utilizes two oligonucleotides for conventional PCR amplification and a third specific oligonucleotide probe that is labeled with a reporter at the 5' end and a quencher at the 3' end of the oligonucleotide. In the instant invention, FAM (6-carboxyfluorescein) and JOE (6 carboxy-4,5-dichloro-2,7-dimethoxyfluorescein) were the two reporters that were utilized and TAMRA (6-carboxy-4,7,2,7'-tetramethylrhodamine) was the quencher. As amplification progresses, the labeled oligonucleotide probe hybridizes to the aene sequence between the two oligonucleotides used for amplification. The nuclease activity of Taq, or rTth thermostable DNA polymerases is utilized to cleave the labeled probe. This separates the quencher from the reporter and generates a fluorescent signal that is directly proportional to the amount of amplicon generated. This labeled probe confers a high degree of specificity. Non-specific amplification is not detected as the labeled probe does not hybridize. All experiments were conducted in a PE7700 Sequence Detection System (Perkin Elmer, Foster City Calif.), Quantitative RT-PCR: For the detection of RNA encoding SNORF36 receptors, quantitative RT-PCR was performed on mRNA extracted from tissue. Reverse transcription and PCR reactions were carried out in 50 µl volumes using rTth DNA polymerase (Perkin Elmer).

Primers for human SNORF36 were designed to amplify the long subtype selectively (SNORF36b) or to a region common to both SNORF36a and SNORF36b. Amounts of RNA encoding the short subtype (SNORF36a) were calculated by subtracting the amount of SNORF36b from the amount of total SNORF36. Primers with the following sequences were used:

Human SNORF36 Subtype Non-selective:
Forward primer:
SNORF36b2-457F
5'-GGCTGCGAGTTCTATGCCTT-3' (SEQ ID NO: 36)
Reverse primer
SNORF36b2-547r
5'-TTACCAGGTAGCGGTCCAGG-3' (SEQ ID NO: 37)
Fluorogenic oligonucleotide probe:
SNORF36b2–483T
5' (6-FAM)-AGCTCTCTTTGGCATTTCCTCCATGATCA-(TAMRA) 3'(SEQ ID NO: 38)
Human SNORF36b (long subtype) Selective:
Forward primer:
SNORF36b b sel-256F
5'-CTGGGCAACCTGACGGTC-3' (SEQ ID NO: 39)
Reverse primer
SNORF36b b sel-346R
5'-CAGGTGTCCGGAGGCTTCT-3' (SEQ ID NO: 40)
Fluorogenic oligonucleotide probe:
SNORF36b b sel-294T
5' (6-FAM)-TGTGCTTCGTGGAGTCACTGTGATGAT-(TAMRA) 3' (SEQ ID NO: 41)
Rat SNORF36
Forward primer
SNORF36-rat-34F
5'-TCCACTGGCCACCATCG-3' (SEQ ID NO: 42)
Reverse primer
SNORF36-rat-107R

5'-GGGCATAGAGCCAGACACCTAG-3' (SEQ ID NO: 43)

Fluorogenic oligonucleotide probe:
SNORF36-rat-52T
5'(6-FAM)-CATGAGATCCAAGAGACGGACGGCA-(TAMRA) 3' (SEQ ID NO: 44)

Using these primer pairs, amplicon length is 90 bp for human SNORF36-non subtype-selective, 90 bp for human SNORF36b-selective, and 73 bp for rat SNORF36. Each human SNORF36 RT-PCR reaction contained 50 ng mRNA and each rat SNORF36 RT-PCR reaction contained 100 ng total RNA. Oligonuceotide concentrations were: 500 nM of forward and reverse primers, and 200 nM of fluorogenic probe. Concentrations of reagents in each reaction were: 300 µM each of dGTP; dATP; dCTP; 600 µM UTP; 3.0 mM Mn(OAc)2; 50 mM Bicine; 115 mM potassium acetate, 8% glycerol, 5 units rTth DNA polymerase, and 0.5 units of uracil N-glycosylase. Buffer for RT-PCR reactions also contained a fluor used as a passive reference (ROX: Perkin Elmer proprietary passive reference I). All reagents for RT-PCR (except mRNA and oligonucleotide primers) were obtained from Perkin Elmer (Foster City, Calif.). Reactions were carried using the following thermal cycler profile: 50° C. 2 min., 60° C. 30 min., 95° C. 5 min., followed by 40 cycles of: 94° C., 20 sec., 62° C. 1 min.

Positive controls for PCR reactions consisted of amplification of the target sequence from a plasmid construct when available. Standard curves for quantitation of human SNORF36 were constructed using the SNORF36 gene in a plasmid construct. RNA extracted from whole brain was used to construct a standard curve for rat SNORF36. Negative controls consisted of mRNA blanks, as well as primer and mRNA blanks. To confirm that the mRNA was not contaminated with genomic DNA, PCR reactions were carried out without reverse transcription using Taq DNA polymerase. Integrity of RNA was assessed by amplification of RNA coding for cyclophilin or glyceraldehyde 3-phosphate dehydrogenase (GAPDH). Following reverse transcription and PCR amplification, data was analyzed using Perkin Elmer sequence detection software. The fluorescent signal from each well was normalized using an internal passive reference, and data was fitted a standard curve to obtain relative quantities of SNORF36 mRNA expression.

RESULTS AND DISCUSSION

Identification of a Fragment of the Human SNORF36 Receptor

A human placental genomic library was screened, under reduced stringency conditions, with oligonucleotide probes directed to the third, fifth and sixth transmembrane regions of the human serotonin 5-HT1$_D$ receptor. Positively-hybridizing clones were isolated, plaque-purified, characterized by Southern blot analysis, and sequenced. One clone, hp10b, contained a 2.3 kb HindIII/XbaI fragment which hybridized with the human 5-HT1$_D$-derived oligonucleotide probes and was subsequently subcloned into a pUC vector. This clone, called K39, was a partial gene fragment, encoding TMII and TMIII and a possible downstream intron of a putative novel GPCR.

Isolation of a Full-length Human SNORF36 Receptor

In order to obtain additional sequence for this receptor, a human hippocampal cDNA library was screened by PCR using primers directed against K39. One positive pool was successfully subdivided until a single clone, TL252, was isolated. DNA sequencing of this clone revealed that it contained TMI through TMVII but was lacking the NH$_2$ and COOH termini. The remaining sequence, including the initiating methionine and the stop codon were obtained by 5' and 3' RACE performed on human hippocampal cDNA. The human hippocampal cDNA library was re-screened and two positive clones were identified, 260-13-1 and 143-33-3, which contained TMI through the stop codon. These two clones both had an 11 amino acid insert in the first intracellular loop that was not present in TL252.

A full-length cDNA clone for SNORF36a (without the 11 amino acid insert) was obtained by ligating together a 1021 bp BamHI/BglI fragment from a hippocampal cDNA PCR product along with a 1180 bp BglI/EcoRI fragment from the human hippocampal library pool 260.13.1 into a BamHI/EcoRI-cut pcDNA3.1. This construct, BO108, had a single nucleotide mutation which was corrected by site-directed mutagenesis. The corrected construct, B0109, was renamed pcDNA3.1-hSNORF36a-f. Analysis of 9 independent PCR products from human hippocampal cDNA revealed the presence of an allelic variation. Nucleotide 39 (FIGS. 1A–1C and 3A–3C) is either an adenine or a guanine. A full-length clone for SNORF36b (with the 11 amino acid insert) was obtained by ligating together a 1130 bp NspI/HindIII fragment from a PCR of BO108 along with a 390 bp BamHI/NspI fragment from one of the PCP products described above into a BamHI/HindIII-cut pcDNA3.1. The resulting SNOPF36b construct, BO110, was renamed pcDNA3.1-hSNORF36b-f.

The largest open reading frame in SNORF36a is 1434 nucleotides, which is predicted to encode a protein of 478 amino acids. Using a downstream methionine results in an open frame of 1377 nucleotides and is predicted to encode a protein of 459 amino acids. The nucleotide and amino acid sequences of SNORF36a are shown in FIGS. 1A–1C and 2A–2B, respectively. The largest open reading frame in SNORF36b is 1467 nucleotides, which is predicted to encode a protein of 489 amino acids. Using a downstream methionine results in an open frame of 1410 nucleotides and is predicted to encode a protein of 470 amino acids. The nucleotide and amino acid sequences of SNORF36b are shown in FIGS. 3A–3C and 4A–4C respectively. Hydropathy analysis of both SNORF36a and SNORF36b protein are consistent with a putative topography of seven transmembrane domains, indicative of the G protein-coupled receptor family.

A comparison of nucleotide and peptide sequences of human SNORF36a and SNORF36b with sequences contained in the Genbank, EMBL, and SwissProtPlus databases reveals that the amino acid sequences of these clones are most related to the Xenopus melanopsin receptor (45% identity), giant octopus rhodopsin (38% identity), giant scallop rhodopsin (36% identity), Japanese flying squid and cuttlefish rhodopsins (35% identities), squid rhodopsin (34% identity), human peropsin and human RGR (31% identities), human encephalopsin (30% identity), human rhodopsin (28% identity) and bovine rhodopsin (27% identity). There were no sequences in the Genbank databases (Genembl, STS, EST, GSS, or SwissProt) that were identical to SNORF36.

Human SNORF36a and SNORF36b have seven potential protein kinase C (PKC) phosphorylation motifs at serine 111 in the first intracellular loop (numbers in this section are relative to SNORF36b in FIGS. 4A–4C), serine 194 in the second intracellular loop, threonine 276 in the third intracellular loop, and at serines 386, 395, and 415 and threonine 399 in the carboxy-terminal tail. There is also one potential N-linked glycosylation site at asparagine 88 in the first transmembrane domain and one cAMP phosphorylation site at serine 390. SNORF36a and SNORF36b also have two potential casein kinase II phosphorylation sites at serine 425 and threonine 432 in the carboxy-terminal tail.

Isolation of a Fragment of the Rat Homologue of SNORF36

Figure 6:
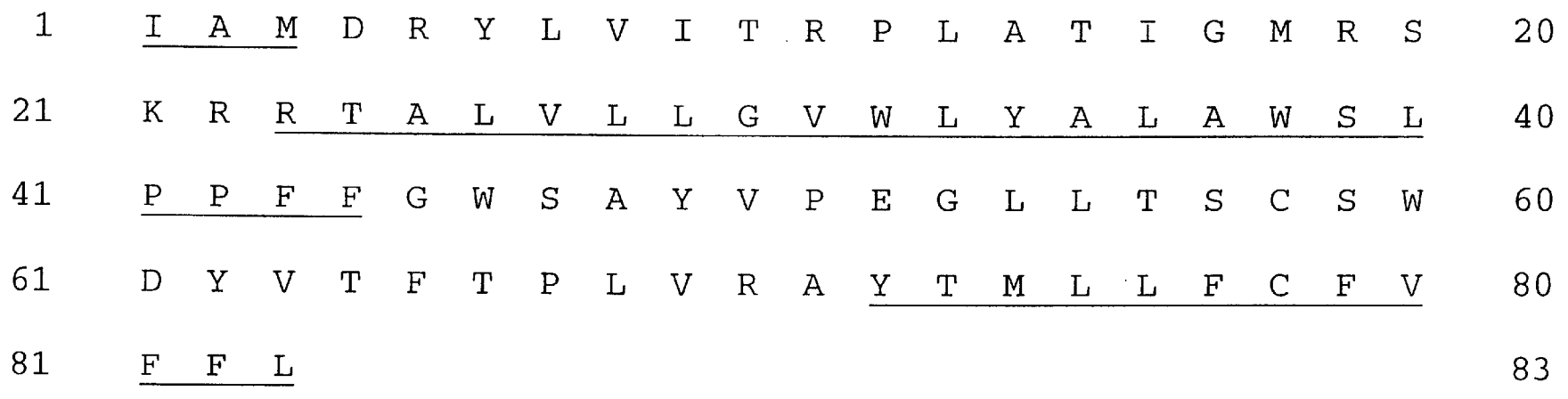

A fragment of the rat homologue of SNORF36 was amplified from rat genomic DNA by low stringency PCR using oligonucleotide primers designed against the human SNORF36. The sequence of this fragment was then used to generate rat SNORF36 PCR primers which were used to amplify under high stringency a SNORF36 fragment from rat spinal cord cDNA. This fragment, KO56, contains 250 nucleotides of rat SNORF36, from the 3' end of TMII to the middle of TMV. The nucleotide and amino acid sequences of the rat SNORF36 fragment are shown in FIGS. 5 and 6, respectively. The rat SNORF36 fragment shares 86% nucleotide and 88% amino acid identities with the human SNORF36 (FIGS. 7 and 8). KO56 was renamed pEXJ-T3T7-rSNORF36p. There were no sequences in the Genbank databases (Genembl, STS, EST, GSS, or SwissProt) that were identical to rat SNORF36.

Isolation of a full-length Rat SNORF36 Receptor

In order to obtain a full-length cDNA for rat SNORF36, a rat spinal cord cDNA library was screened by PCP using primers directed against the rat SNORF36 fragment, KO56. One positive pool was successfully subdivided until a single clone, BO132, was isolated. DNA sequencing of this clone revealed that it contained an open reading frame of 1422 nucleotides, 148 nucleotides of 5'UT and approximately 1000 nucleotides of 3'UT. The construct BO132, in the expression vector pEXJ.T7, was renamed pEXJ.T7-rSNORF36-f.

The largest open reading frame in the rat SNORF36 construct BO132 is 1422 nucleotides, which is predicted to encode a protein of 474 amino acids. The nucleotide and amino acid sequences of rat SNORF36 are shown in FIGS. 9A–9C and 10A–10C, respectively. Hydropathy analysis of the rat SNORF36 protein are consistent with a putative topography of seven transmembrane domains, indicative of the G protein-coupled receptor family.

Rat SNORF36 shares 81% nucleotide identity and 79% amino acid identity with human SNORF36a (FIGS. 11A–11D and 12A–12B, respectively). A comparison of nucleotide and peptide sequences of rat SNORF36 with sequences contained in the Genbank, EMBL, and SwissProtPlus databases reveals that the amino acid sequences of these clones are most related to the Xenopus melanopsin receptor (46% identity), giant octopus rhodopsin and giant scallop rhodopsin (35% identities), cuttlefish rhodopsin (34% identity), Japanese flying squid and mouse peropsin (33% identities), human RGR (32% identity), human and bovine rhodopsin (28% identities) and human encephalopsin (27% identity). There were no sequences in the Genbank databases (Genembl, STS, EST, GSS, or SwissProt) that were identical to rat SNORF36.

Rat SNORF36 has six potential protein kinase C (PKC) phosphorylation motifs at serine 183 in the second intracellular loop, threonine 265 in the third intracellular loop, and at serines 381 and 385, and threonines 460 and 463 in the carboxy-terminal tail. There are also three potential N-linked glycosylation sites at asparagines 31 and 35 in the amino terminal tail and at asparagine 88 in the first transmembrane domain. There is one cAMP phosphorylation site at threonine 187 in the fourth transmembrane domain, and three potential casein kinase II phosphorylation sites at serines 411 and 452 and threonine 418 in the carboxy-terminal tail.

$Ca^{2+}$ Mobilization and Phosphoinositide Hydrolysis in SNORF36a-expressing Cells Since SNORF36a is similar to invertebrate opsins, it was hypothesized that it may couple to $G_q$ G-protein and may induce phosphoinositide hydrolysis followed by release of intracellular $Ca^{2+}$. Therefore, $Ca^{2+}$ mobilization and inositol phosphate (IP) accumulation were evaluated in hSNORF36a-transfected Cos-7 cells. Exposure to laser light of hSNORF36a-transfected Cos-7 cells, kept in dark, in the FLIPR resulted in $Ca^{2+}$ mobilization in the absence of any exogenous ligand (FIG. 13A). This observation suggested that an endogenous chromophore, probably a retinal isomer, was already attached to the hSNORF36a receptor, and exposure to laser light resulted in photoisomerization of the ligand and activation of the receptor. Since this situation did not allow us to study the effect of an exogenolusly added ligand, we 'photobleached' the hSNORF36a- and vector-transfected Cos-7 cells by exposing them to light for 90–120 minutes prior to the experiment. Photobleaching is a phenomenon where exposure to light results in photoisomerization of the endogenous ligand, eventually leading to release of the ligand and formation of an opsin with an empty binding pocket. This technique is used widely to dissociate the endogenous ligand from rhodopsin. Upon photobleaching, the $Ca^{2+}$ mobilization response to laser light in the hSNORF36a-transfected Cos-7 cells was either reduced or completely abolished (FIG. 13B) implying dissociation of the endogenous ligand. Therefore, photobleaching was used for all subsequent experiments unless indicated otherwise.

Opsins can be activated by several retinal analogues, including all-trans-retinal (Surya and Knox, 1998) which is a 'natural' agonist formed upon photoisomerization of 11-cis-retinal. Upon addition of retinal analogues to photobleached SNORF36a-transfected Cos-7 cells, significant $Ca^{2+}$ mobilization was observed (FIGS. 14A, 15A). The rank order of potency was 9-cis-retinal ($EC_{50}$:152 nM)>all-trans-retinal ($EC_{50}$:263 nM)>13-cis-retinal ($EC_{50}$:477 nM) (See FIG. 15A). A similar response to all-trans-retinal was seen in photobleached SNORF36a-transfected HEK293 cells (FIG. 15B). In contrast, retinals did not change intracellular $Ca^{+2}$ levels in the vector-transfected Cos-7 cells (FIG. 14B). Collectively, these results indicate that SNORF36a is an opsin which can be activated by retinals. To confirm these results further, we examined the effect of SNORF36a on IP formation. Concentration-dependent increase in $^3$H-IP accumulation was seen upon all-trans-retinal addition (FIG. 16A) in SNORF36a-transfected Cos-7 cells exposed to light but not in vector-transfected cells (FIG. 16A). In contrast, in SNORF36a-transfected Cos-7 cells not exposed to light, all-trans-retinal did not change $^3$H-IP levels, indicating that light may be required either for dissociation of endogenous ligand or activation of the receptor (FIG. 16B). Collectively, these results suggest that activation of hSNORF36a can induce phosphoinositide hydrolysis which may be upstream of intracellular $Ca^{2+}$ mobilization. Finally, we tested the potential antagonism by β-ionone which is structurally similar to retinals. β-ionone, at 10 μM concentration, significantly antagonized responses to all-trans-retinal and 9-cis-retinal in hSNORF36a-transfected Cos-7 cells (FIGS. 17A and 17B). The antagonism by β-ionone appeared to be insurmountable (FIGS. 17A and 17B). This may be due to the intrinsic characteristics of β-ionone-hSNORF36a interaction. Alternatively, it may represent the hemiequilibrium conditions achieved in the assay. Nonetheless, these results confirm that retinal-like structure can bind to this receptor. These results are consistent with the notion that SNORF36a is an opsin coupled to $Ca^{2+}$ mobilization and phosphoinositide hydrolysis, most likely via $G_q$ G-protein, and is activated by retinals.

Photic Responses From Oocytes Expressing SNORF36a

The experiments with mammalian cells suggest that SNORF36a, stimulated by the presence of retinoids, can activate a second messenger response that includes release of inositol triphosphates and intracellular free $Ca_{++}$. Heterologous expression in Xenopus oocytes has been widely used to study the ligand binding and functional activity of a variety of G-protein coupled receptors (Gundersen et al., 1983; Takahashi et al., 1987), including rhodopsin (Khorana et al., 1988). Activation of the PLC pathway in oocytes leads to stimulation of the endogenous $Ca^{++}$-activated $Cl^-$ current. We sought to determine if oocytes expressing SNORF36a could be stimulated by retinoids, and if sensitivity to retinoids was dependent upon activation by light.

Figure 18A:
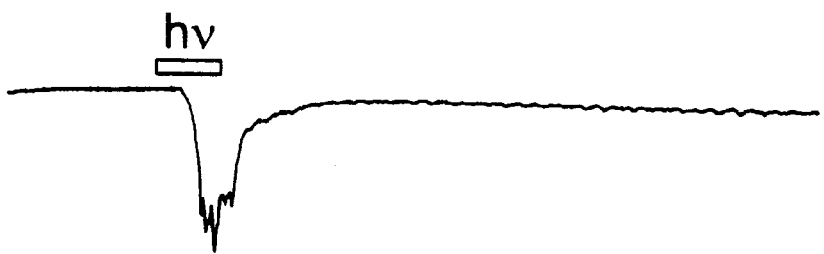
Figure 18B:
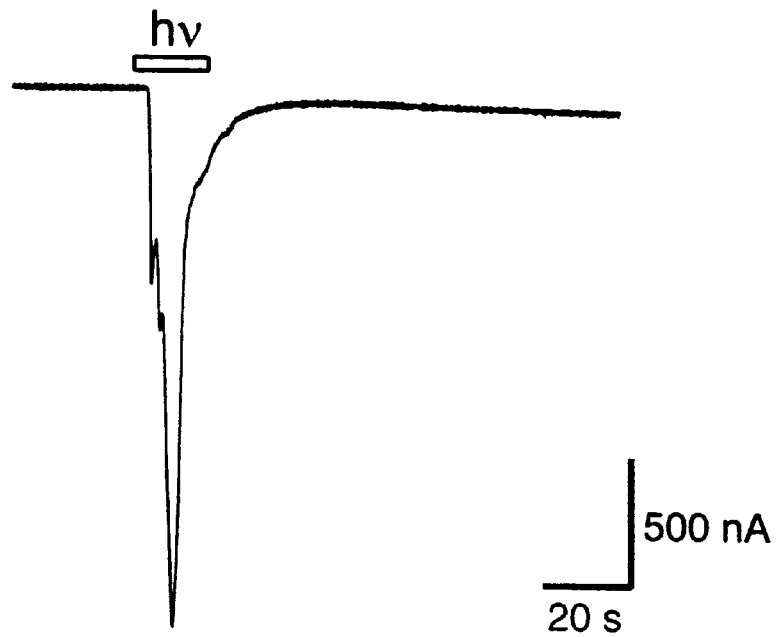
Figure 18C:
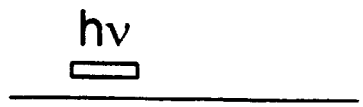
Figure 19:
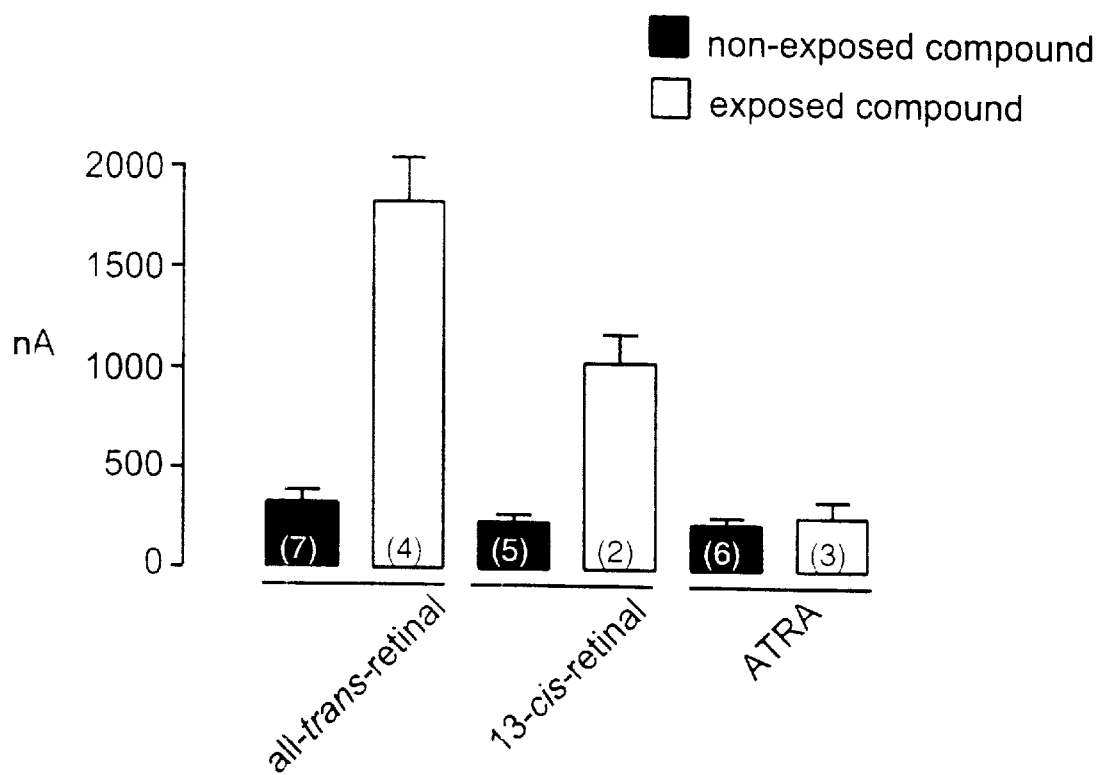

Upon acute administration of retinoids to oocytes expressing SNORF36a, no ionic currents were detected under dark conditions or subsequent to the light stimulus. This result suggested that preincubation of ligands may be necessary to see activation of the receptors. To detect light-dependent ionic responses in Xenopus oocytes expressing bovine opsin, Khorana and co-workers (1988) incubated oocytes for 30–40 minutes with 11-cis retinal to permit the formation of rhodopsin. In another example, the photosensitivity of Xenopus melanophores has been seen to occur only following for several hours preincubation with all-trans retinal (Rollag, 1996). Following these examples, oocytes expressing SNORF36a were preincubated in the dark for 24–48 h with all-trans-retinal, 13-cis-retinal, or all-trans-retinoic acid (ATRA) (each at 100 nM) in $ND96^{++}$ (FIG. 19). When preincubated with any of these ligands, the oocytes produced rapidly desensitizing $Cl^-$ currents in response to the light stimulus (FIGS. 18A and 19). Current amplitudes ranged from 100 to 500 nA, and appeared quite similar in waveform to those elicited by stimulation of receptors that are known to activate PLC (Gundersen et al., 1983). The currents generated by SNORF36a stimulation were considerably larger in amplitude than those reported for oocytes expressing bovine rod opsin (about 5 nA, Khorana et al., 1988). The reason for this is likely due to the different signal transduction pathways activated by these two receptors. SNORF36a may evoke release of intracellular $Ca^{++}$ via activation of $G\alpha_q$, whereas vertebrate opsin couples to transducin and cannot directly activate the PLC pathway. Except for ATRA, the retinoids that were exposed to room light before incubation with the oocytes expressing SNORF36a produced significantly larger current amplitudes (about 5-fold) than non-exposed retinoids (FIGS. 18B and 19). Control oocytes, not injected with SNORF36a mRNA, that were pre-incubated with all-trans-retinal or 13-cis-retinal did not respond to light (FIG. 18C; n=10 oocytes).

Detection of RNA Coding for Human SNORF36 Receptors mRNA was isolated from multiple tissues (listed in Table 1) and assayed as described.

Human SNORF36

Quantitative RT-PCR using a fluorgenic probe demonstrated mRNA encoding human SNORF36 to be localized in highest abundance in CNS tissue. All CNS tissues assayed demonstrate measurable levels of SNORF36 RNA.

Highest levels are found in the caudate-putamen, amygdala and hippocampus. Localization of high levels of SNORF36 RNA to the caudate-putamen indicates a role in modulation of dopaminergic function, or the modulation of extrapyramidal motor systems. High levels of SNORF36 RNA in the hippocampal formation and amygdala support the hypothesis that SNORF36 is involved in the modulation of learning and memory. It may also have a role in the regulation of fear, mood, and may provide a target for the treatment of depression, anxiety, phobias and mood disorders. Other regions of the CNS containing SNORF36 RNA include the spinal cord and thalamus, implying an important role in sensory transmission or modulation (including nociception). SNORF36 is also expressed in lower levels in the substania nigra, hypothalamus, and cerebellum. The broad distribution of SNORF36 RNA throughout the CNS implies a modulatory role in multiple systems within the CNS.

Fetal brain, although expressing SNORF36 mRNA does so in much lower levels than that found in the adult. In fetal brain, SNORF36 RNA is barely detectable. There is a 70-fold difference in mRNA levels between fetal and adult brain. It is not known at this time if the developmental regulation occurs in all regions within the CNS or is restricted to selected areas. The time course of this increase has not been examined and would be important in understanding the function of this receptor.

In peripheral tissue, most tissues assayed expressed measurable SNORF36 mRNA levels. The peripheral tissues expressing the highest levels of SNORF36 mRNA are skeletal muscle, heart and small intestine. Levels in these tissues are 10-fold lower than that detected in the highest CNS regions. Presence of SNORF36 mRNA in these areas implies a role in regulation of contractility, perhaps by a common mechanism. Other tissues assayed contain low levels of SNORF36 mRNA as indicated in Table 1.

Both subtypes (SNORF36a and SNORF36b) were assayed in all tissue samples. Primers for human SNORF36 were designed to amplify the long subtype selectively (SNORF36b) or to a region common to both SNORF36a and SNORF36b. Amounts of RNA encoding the short subtype (SNORF36a) were calculated by subtracting the amount of SNORF36b from the amount of total SNORF36. In most regions assayed, SNORF36a is the predominant subtype expressed. The exceptions are the caudate-putamen and fetal lung. In these tissues, SNORF36a accounts for 31% and 43%, respectively, of the total SNORF36. However, in all other tissue assayed, SNORF36a accounts for 60% to 100% of the total SNORF36 present in tissue.

In summary, the distribution of human SNORF36 mRNA implies broad regulatory function in the CNS, most notably in modulation of extrapyramidal motor systems, modulation of the limbic system, and sensory transmission. Its presence, albeit at lower levels, in peripheral tissues implies a broad regulatory role in multiple organ systems. The predominance of SNORF36a in most tissue indicates that functionally, it is the dominant subtype.

Rat SNORF36

As with the human SNORF36 receptor mRNA, all central nervous system structures assayed contain rat SNORF36 RNA. However, the highest levels of rat SNORF36 RNA are found in the retina (Table 2). The retina contains 5-fold more RNA encoding SNORF36 than any other tissue. The high levels found in the retina imply a function in vision or photoentrainment. The hypothesis that rat SNORF36 plays a role in circadian rhythm is supported by the fact that substantial levels of SNORF36 RNA are also expressed in the pineal gland, as well as the hypothalamus (Table 2). The localization and functional data imply that SNORF36 is a non-rod, non-cone, ocular photoreceptor. It has been suggested that non-rod, non-cone ocular photoreceptors are responsible for photoentrainment and regulation of melatonin synthesis in the pineal gland (Freedman et al., 1999, Lucas et al., 1999).

Other regions containing high levels of SNORF36 RNA include trigeminal ganglia, spinal cord, and medulla. Localization to these structures as well as moderate levels in the dorsal root ganglia, strongly suggest a role in sensory transmission (or modulation) including nociceptive stimuli. Localization in the medulla also implies regulation of autonomic centers controlling respiration and cardiovascular function. Other CNS regions containing high levels of SNORF36 RNA include the amygdala, and substanta nigra. High levels in the amygdala and other limbic (or limbic related) structures suggests a role in modulation of mood, fear, phobia, anxiety and may provide a therapeutic target for the treatment of depression and other neuropsychiatric disorders. Localization to the substantia nigra (in conjunction with expression in the striatum) implies a role in regulation of dopaminergic systems, and may provide a therapeutic target for treatment of movement disorders such as Parkinsons disease or tardive dyskinesea.

The high levels of SNORF36 mRNA expressed in the hypothalamus described previously, in addition to the potential role in regulation of circadian rhythm, also indicates a role in neuroendocrine regulation, regulation of appetite and other functions that are modulated by the hypothalamus. High levels in the amygdala suggest a role in modulation of mood, fear, phobia, anxiety and may provide a therapeutic target for the treatment of depression and other neuropsychiatric disorders.

The presence of lower levels of SNORF36 RNA in other areas such as the hippocampal formation, olfactory bulb, cerebral cortex, cerebellum and other areas suggests multiple diverse functions as suggested in Table 2.

Non-neuronal tissue expressing high levels of SNORF36 RNA include the ovary and testes. Levels in these areas are comparable to many CNS regions including the cerebral cortex and cerebellum (Table 2). This strongly suggests a role in endocrine regulation or reproductive function, by neuronal or extraneuronal mechanisms. Other peripheral tissues showing moderate amounts of SNORF36 mRNA are listed in Table 2.

In summary, the high levels or SNORF36 RNA in the retina, pineal gland, and hypothalamus suggest a role as a non-rod, non-cone ocular photoreceptor involved in regulation of circadian rhythms. The distribution of rat SNORF36 mRNA throughout the CNS implies broad regulatory function in the nervous system. Potential functions include modulation of sensory transmission, modulation of extrapyramidal motor systems, and modulation of the limbic system. The ovary and testes are among multiple peripheral organs that may be regulated by SNORF36. Its presence, albeit at lower levels, in other peripheral tissues implies a broad regulatory role in multiple organ systems.

TABLE 1

Summary of distribution of mRNA coding for human SNORF36 receptors (long and short forms). Amounts of mRNA encoding human SNORF36 expressed as, mean (whole brain standard curve), % of highest expressing tissue (CPu ± SEM).

| Region | SNORF36 % of max | SNORF36b % of max | SNOR-F36a % of max | SNOR-F36a % of SNORF36 | Potential applications |
|---|---|---|---|---|---|
| amygdala | 50.10 ± 5.73 | 14.64 | 35.47 | 70.78 | Depression phobias, anxiety, mood disorders |
| caudate-putamen | 100.00 ± 7.89 | 69.18 | 30.82 | 30.82 | Modulation of dopaminergic function, Modulation of extrapyramidal motor systems |
| cerebellum | 0.31 ± 0.07 | not detected | 0.31 | 100 | Motor coordination |
| fetal brain | 0.22 ± 0.05 | 0.01 | 0.22 | 97.28 | Developmental disorders |
| fetal kidney | 0.61 ± 0.10 | not detected | 0.61 | 100 | Developmental disorders |
| fetal liver | 0.04 ± 0.01 | 0.01 | 0.03 | 63.08 | Developmental disorders |
| fetal lung | 0.42 ± 0.11 | 0.24 | 0.18 | 42.79 | Developmental disorders |
| heart | 7.44 ± 2.46 | not detected | 7.44 | 100 | Cardiovascular disorders |
| hippocampus | 26.28 ± 1.76 | 10.52 | 15.76 | 59.96 | Cognition/memory |
| hypothalamus | 0.77 ± 0.07 | 0.04 | 0.72 | 94.49 | appetite/obesity, neuroendocrine regulation |
| kidney | 0.16 ± 0.04 | trace | 0.16 | 100 | Hypertension, electrolyte balance |
| liver | trace | trace | 0.02 | NA | Diabetes |
| lung | trace | trace | 0.03 | NA | Respiratory disorders, asthma |
| pancreas | 0.07 ± 0.01 | not detected | 0.07 | 100 | Diabetes, endocrine disorders |
| pituitary | 4.38 ± 0.78 | 0.17 | 4.21 | 96.20 | Endocrine/neuroendocrine regulation |
| placenta | 0.03 ± 0.01 | 0.05 ± 0.02 | 0.03 | 100 | Gestational abnormalities |
| small intestine | 6.24 ± 1.51 | 0.34 | 5.90 | 94.51 | Gastrointestinal disorders |
| spinal cord | 7.60 ± 1.38 | 0.06 | 7.54 | 99.18 | Analgesia, sensory modulation and transmission |
| spleen | 0.10 ± 0.02 | trace | 0.10 | 100 | Immune disorders |
| stomach | trace | trace | trace | NA | Gastro- |

TABLE 1-continued

Summary of distribution of mRNA coding for human SNORF36 receptors (long and short forms).
Amounts of mRNA encoding human SNORF36 expressed as, mean (whole brain standard curve), % of highest expressing tissue (CPu ± SEM).

| Region | SNORF36 % of max | SNORF36b % of max | SNOR-F36a % of max | SNOR-F36a % of SNORF36 | Potential applications |
|---|---|---|---|---|---|
| | | | | | intestinal disorders |
| skeletal muscle | 10.51 ± 0.88 | 0.30 | 10.21 | 97.15 | Musculo-skeletal disorders |
| sub-stantia nigra | 3.73 ± 0.22 | 0.17 | 3.57 | 95.48 | Modulation of dopamin-ergic function. Modulation of motor coordina-tion. |
| thalamus | 5.56 ± 0.70 | 1.19 | 4.37 | 78.62 | Sensory integra-tion disorders |
| whole brain | 15.82 ± 2.28 | 4.97 | 10.85 | 68.59 | |

TABLE 2

Summary of distribution of mRNA coding for rat SNORF36 receptors
mRNA encoding SNORF36 is expressed as % of highest expressing tissue: retina ± SEM.

| Tissue | SNORF36 | Potential applications |
|---|---|---|
| adipose | 1.93± 0.21 | metabolic disorders |
| adrenal cortex | 2.62± 0.48 | regulation of steroid hormones |
| adrenal medulla | 2.86± 0.24 | regulation of epinephrine release |
| amygdala | 9.52± 0.75 | depression, phobias, anxiety, mood disorders |
| aorta | 1.08± 0.07 | cardiovascular disorders |
| celiac plexus | 1.58± 0.14 | modulation of autonomic function |
| cerebellum | 4.81± 0.43 | motor coordination |
| cerebral cortex | 6.35± 0.41 | Sensory and motor integration, cognition |
| choroid plexus | 7.02± 0.93 | regulation of cerebrospinal fluid |
| colon | 0.61± 0.05 | gastrointestinal disorders |
| dorsal root ganglia | 4.18± 0.23 | sensory transmission |
| duodenum | 0.86± 0.10 | gastrointestinal disorders |
| heart | 1.79± 0.19 | cardiovascular indications |
| hippocampus | 3.45± 0.37 | cognition/memory |
| hypothalamus | 9.13± 0.62 | appetite/obesity, neuroendocrine regulation |
| kidney | 0.95± 0.07 | electrolyte balance, hypertension |
| liver | trace | diabetes |
| medulla | 9.33± 0.57 | analgesia, motor coordination |
| nucleus accumbens | 4.29± 0.36 | regulation of dopaminergic function, drug addiction, neuropsychiatric disorders |
| olfactory bulb | 3.96± 0.33 | olfaction |
| ovary | 6.83± 0.66 | reproductive function |
| pancreas | 0.30± 0.04 | diabetes, endocrine disorders |
| pineal | 8.37± 0.21 | regulation of melatonin release |
| pituitary | 3.68± 0.37 | endocrine/neuroendocrine regulation |
| retina | 100 ± 7.26 | visual disorders, circadian rhythms |
| salivary gland | 1.26± 0.21 | |
| spinal cord | 14.47± 0.44 | analgesia, sensory modulation and transmission |
| spleen | 0.27± 0.14 | immune disorders |
| stomach | 0.30± 0.02 | gastrointestinal disorders |
| striated muscle | 2.08± 0.18 | musculoskeletal disorders |
| striatum | 3.72± 0.67 | modulation of dopaminergic function, motor disorders |
| substantia nigra | 11.92± 2.46 | modulation of dopaminergic function, modulation of motor coordination |
| testes | 5.48± 0.21 | reproductive function |
| thalamus | 3.85± 0.16 | sensory integration disorders |
| thymus | 3.07± 0.37 | immune disorders |
| trigeminal ganglia | 19.13± 2.83 | sensory transmission |
| urinary bladder | 1.48± 0.11 | urinary incontinence |
| uterus | 1.16± 0.14 | reproductive disorders |
| vas deferens | 2.85± 0.21 | reproductive function |
| whole brain | 4.12± 0.39 | |

REFERENCES

Arnheiter, H., "Eyes viewed from the skin" *Nature* 391:632–633 (1998).

Blackshaw, S., and Snyder, S. H., "Parapinopsin, a novel catfish opsin localized to the parapineal organ, defines a new gene family" *J. Neurosci.* 17:8083–8092 (1997).

Blackshaw, S., and Snyder, S. H., "Encephalopsin: a novel mammalian extraretinal opsin discretely localized in the brain" *J. Neurosci.* 19: 3681–3690 (1999).

Bradford, M. M., "A rapid and sensitive method for the quantitation of microgram quantities of protein utilizing the principle of protein-dye binding", *Anal. Biochem.* 72: 248–254 (1976).

Burns, C. C., et al., "Indentification and deletion of sequences required for feline leukemia virus RNA packaging and construction of a high-titer feline leukemia virus packaging cell line", *Virology* 222(1): 14–20 (1996).

Bush, et al., "Nerve growth factor potentiates bradykinin-induced calcium influx and release in PC12 cells" *J. Neurochem.* 57: 562–574(1991).

Campbell, et al., "Light treatment for sleep disorders: consensus report V. Age-related disturbances" *J. Biol. Rhythms* 10: 151–154 (1995).

Chan, T., et al., "Introduction of hydroxyl-bearing amino acids causes bathochromic spectral shifts in rhodopsin. Amino acid substitutions responsible for red-green color pigment spectral tuning" *J. Biol. Chem.* 267: 9478–9480 (1992).

Chu, Y. Y., et al., "Characterization of the rat A2a adenosine receptor gene", *DNA Cell Biol.* 15(4): 329–337 (1996).

Cohen, G. B., et al., "Constitutive activation of opsin: influence of charge at position 134 and size at position 296" *Biochem.* 32: 6111–6115 (1993).

Cooke, K. M., et al., "The effects of evening light exposure on the sleep of elderly women expressing sleep complaints" *J. Behav. Med.* 21: 103–114 (1998).

Dascal, N., et al., "Atrial G protein-activated $K^+$ channel: expression cloning and molecular properties" *Proc. Natl. Acad. Sci. USA* 90: 10235–10239 (1993).

Fong, T. M., et al., "Mutational analysis of neurokinin receptor function" *Can. J. Physio. Pharmacol.* 73(7): 860–865 (1995).

Foster, P. G., "Shedding light on the biological clock" *Neuron* 20: 829–832 (1998).

Foster, P. G., et al., "Opsin localization and chromophore retinoids identified within the basal brain of the lizard *Anolis carolinensis*" *J. Comp. Physiol. A.* 172: 33–45 (1993).

Foster, R. G., et al., "Identification of vertebrate deep brain photoreceptors" *Neurosci. Biobehav. Rev.* 18: 541–546 (1994).

Franke, H., et al., "An improved low-permeability in vitro-model of the blood-brain barrier: transport studies on retinoids, sucrose, haloperidol, caffeine and mannitol" *Brain Res.* 818: 65–71 (1999).

Freedman, M. S., et al., "Regulation of mammalian circadian behavior by non-rod, non-cone, ocular photoreceptors" *Science* 284: 502–504 (1999).

Gartner, W., and Towner, P., "Invertebrate visual pigments" *Photochem. Photobiol.* 62: 1–16 (1995).

Grace, M. S., et al., "Light perception in the vertebrate brain: an ultrastructural analysis of opsin- and vasoactive intestinal peptide-immunoactive neurons in Iguanid lizards" *J. Comp. Neurol.* 367: 575–594 (1996).

Graziano, M. P. et al., "The amino terminal domain of the glucagon-like peptide-1 receptor is a critical determinant of subtype specificity" *Receptors Channels* 4(1): 9–17 (1996).

Guan, X. M., et al., "Determination of Structural Domains for G Protein Coupling and Ligand Binding in β3—Adrenergic Receptor" *Mol. Pharmacol.* 48(3): 492–498 (1995).

Gundersen, C. B., et al., "Serotonin receptors induced by exogenous messenger RNA in Xenopus oocytes" *Proc. R. Soc. Lond. B. Biol. Sci.* 219(1214): 103–109 (1983).

Han, M., et al., "The effects of amino acid replacements of glycine 121 on transmembrane helix 3 of rhodopsin" *J. Biol. Chem.* 271: 32330–32226 (1996).

Hao, W., and Fong, H. K. W., "The endogenous chromophore of retinal G protein-coupled receptor opsin from the pigment epithelium" *J. Biol. Chem.* 274: 6085–6090 (1999).

Hara-Nishimura, I., et al., "Cloning and nucleotide sequence of cDNA for retinochrome, retinal photoisomerase from the squid retina" *FEBS Lett.* 271: 106–110 (1990).

Hargrave, P. A., and McDowell, J. H., "Rhodopsin and phototransduction: a model system for G protein-linked receptors" *FASEB J* 6: 2323–2331 (1992).

Hu, S., et al., "Unbleachable rhodopsin with an 11-cis-locked eight-membered ring retinal: the visual transduction process", *Biochem.* 33: 408–416 (1994).

Inanobe, A., et al., "Characterization of G-protein-gated $K^-$ channels composed of Kir3.2 subunits in dopaminergic neurons of the substantia nigra" *J. of Neuroscience* 19(3) 1006–1017 (1999).

Khorana, H. G., et al., "Expression of a bovine rhodopsin gene in Xenopus oocytes: demonstration of light-dependent ionic currents" *Proc. Natl. Acad. Sci. U.S.A.* 85: 7917–7921 (1988).

Kiselev, A., and Subramaniam, S., "Activation and regeneration of rhodopsin in the insect visual cycle" *Science* 266: 1369–1373 (1994).

Kochendoerfer, G. G., et al., "Hoe color visual pigments are tuned" *Trends Biol. Sci.* 24: 300–305 (1999).

Krapivinsky, G., et al., "The cardiac inward rectifier $K^+$ channel subunit, CIR, does not comprise the ATP-sensitive $K^+$ channel, IKATP" *J. Biol. Chem.* 270: 28777–28779 (1995b)

Krapivinsky, G., et al., "The G-protein-gated atrial $K^+$ channel IKACh is a heteromultimer of two inwardly rectifying $K(^+)$-channiel proteins" *Nature* 374: 135–141 (1995).

Kubo, Y., et al., "Primary structure and functional expression of a rat G-protein-coupled muscarinic potassium channel" *Nature* 364: 802–806 (1993).

Lack, L., and Wright, H., "The effect of evening bright light in delaying the circadian rhythms and lengtheniLno the sleep of early morning awakening insomniacs" *Sleep* 16: 436–443 (1993).

Lazareno, S. and Birdsall, N. J. M. "Pharmacological characterization of acetylcholine stimulated [35S]-GTPgS binding mediated by human muscarinic m1-m4 receptors: antagonist studies", *Br. J. Pharmacology* 109: 1120–1127 (1993)

Lucas, R. J., et al., "Regulation of the mammalian pineal by non-rod, non-cone, ocular photoreceptors" *Science* 284: 505–507 (1999).

Max, M., et al., "Pineal opsin: a nonvisual opsin expressed in chick pineal" *Science* 267: 1502–1506 (1995).

Max, M., et al., "Light-dependent activation of rod transducin by pineal opsin" *J. Biol. Chem.* 273: 26820–26826 (1998).

Milligan, G., et al., Chimaeric G alpha proteins: their potential use in drug discovery" *Trends Pharmacol. Sci.* 20: 118–124 (1999).

Muller, P. J., and Wilson, B. C., "An update on the penetration depth of 630 nm light in normal and malignant human brain tissue in vivo" *Phys. Med. Biol.* 31: 1295–1297 (1986).

Murphy, P. J., and Campbell, S. S., "Enhanced performance in elderly subjects following bright light treatment of sleep maintenance insomnia" *J. Sleep Res.* 5: 165–172 (1996).

Nobes, C., et al., "Activation of the GTP-binding protein Gq by rhodopsin in squid photoreceptors" *Biochem. J.* 287: 545–548 (1992).

Okano, T., et al., "Pinopsin is a chicken pineal photoreceptive molecule" *Nature* 372: 94–97 (1994).

Oren, D. A., et al., "Treatment of seasonal affective disorder with green light and red light", *Am. J. Psychiatry* 148: 509–511 (1991).

Pardridge, W. M., et al., "Restricted transport of vitamin D and A derivatives through the rat blood-brain barrier" *J. Neurochem.* 44: 1138–1141 (1985).

Partonen, T., "Short note: magnetoreception attributed to the efficacy of light therapy" *Med. Hypotheses* 51: 447–448 (1998).

Provencio, I., et al., "Melanopsin: an opsin in melanophores, brain and eye" *Proc. Natl. Acad. Sci. USA* 95: 340–345 (1998).

Quick, M. W. and Lester, H. A., "Methods for expression of excitability proteins in Xenopus oocytes", *Meth. Neurosci.* 19: 261–279 (1994).

Refinetti, R., "Chronobiology: Business and Health Care" Circadian Physiology: pp. 127–160, CRC Press (1999).

Rollag, M. D., "Amphibian melanophores become photosensitive when treated with retinal" *J. Exp. Zoology* 275: 20–26 (1996).

Rosenthal, N. E., et al., "Phase-shifting effects of bright morning light as treatment for delayed sleep phase syndrome" *Sleep* 13: 354–361 (1990).

Salon, J. A. and Owicki, J. A., "Real-time measurements of receptor activity: Application of microphysiometic techniques to receptor biology" *Methods in Neuroscience* 25: 201–224, Academic Press (1996).

Sanger, F., et al., "DNA sequencing with chain-terminating inhibitors" *Proc. Natl. Acad. Sci. USA* 74: 5463–5467 (1977).

Sedgwick, P. M., "Disorders of the sleep-wake cycle in adults" *Postgrad. Med. J.* 74: 134–138 (1998).

Silver, R., et al., "Coexpression of opsin- and VIP-like-immunoreactivity in CSF-contacting neurons of the avian brain" *Cell Tiss. Res.* 253: 189–198 (1988).

Smith, K. E., et al., "Expression cloning of a rat hypothalamic galanin receptor coupled to phosphoinositide turnover." *J. Biol. Chem.* 272: 24612–24616 (1997).

Soni, B. G., et al., "Novel retinal photoreceptors" *Nature* 394: 27–28 (1998).

Soni, B. G., et al., "A novel and ancient vertebrate opsin" *FEBS Lett.* 407: 279–283 (1997).

Spurney, R. F., et al., "The C-terminus of the thromboxane receptor contributes to coupling and desensitization in a mouse mesangial cell line", *J. Pharmacol. Exp. Ther.* 283 (1): 207–215 (1997).

Sun, H., et al., "Peropsin, a novel visual pigment-like protein located in the apical microvilli of the retinal pigment epithelium" *Proc. Natl. Acad. Sci. USA* 94: 9893–9898 (1997).

Surya, A., and Knox, B. E., "Enhancement of opsin activity by all-trans-retinal" *Exp. Eye Res.* 66: 599–603 (1998).

Surya, A., et al., "Transducin activation by the bovine opsin apoprotein" *J. Biol. Chem.* 270: 5024–5031 (1995).

Takahashi, T., et al., "Rat brain serotonin receptors in Xenopus oocytes are coupled by intracellular calcium to endogenous channels." *Proc. Natl. Acad. Sci. USA* 84(14): 5063–5067 (1987).

Takanaka, Y., et al., "Light-dependent expression of pinopsin gene in chicken pineal gland" *J. Neurochem.* 70: 908–913 (1998).

Tanaka, T., et al., "Lipocalin-type prostaglandin D-synthase (beta-trace) is a newly recognized type of retinoid transporter" *J. Biol. Chem.* 272: 15789–15795 (1997).

Tao, L., et al., "Structure and developmental expression of the mouse RGR opsin gene" *Mol. Vision* 4: 25–30 (1998).

Terakita, A., et al., "Selective activation of G-protein subtypes by vertebrate and invertebrate rhodopsins" *FEBS Lett.* 439: 110–114 (1998).

Terman, M., and Terman, J. S., "Bright light therapy: side effects and benefits across the symptom spectrum" *J. Clin. Psychiatry* 60: 799–808 (1999).

Tian, W., et al., "Determinants of alpha-Adrenergic Receptor Activation of G protein: Evidence for a Precoupled Receptor/G protein State." *Molecular Pharmacology* 45: 524–553 (1994).

Underwood, D. J. et al., "Structural model of antagonist and agonist binding to the angiotensin II, AT1 subtype, G protein coupled receptor", *Chem. Biol.* 1(4): 211–221 (1994).

Wade, P. D., et al., "Mammalian cerebral cortical tissue responds to low-intensity visible light" *Proc. Natl. Acad. Sci. USA* 85: 9322–9326 (1988).

Wood, S. F., et al., "Inositol triphosphate production in squid photoreceptors. Activation by light, aluminium fluoride, and guanine nucleotides" *J. Biol. Chem.* 264: 12970–12976 (1989).

Yarfitz, S., and Hurley, J. B., "Transduction mechanisms of vertebrate and invertebrate photoreceptors" *J. Biol. Chem.* 269: 14329–14332 (1994).

Yoshikawa, T., and Oishi, T., "Extraretinal photoreception and circadian systems in nonmammalian vertebrates" *Comp. Biochem. Physiol.* 119B: 65–72 (1998).

What is claimed is:

1. A method of screening a plurality of chemical compounds not known to bind to a human SNORF36a receptor to identify a compound which specifically binds to the human SNORF36a receptor, which comprises
   (a) contacting cells transfected with, and expressing, DNA encoding the human SNORF36a receptor with a compound known to bind specifically to the human SNORF36a receptor;
   (b) contacting the cells of step (a) with the plurality of compounds not known to bind specifically to the human SNORF36a receptor, under conditions permitting binding of compounds known to bind to the human SNORF36a receptor;
   (c) determining whether the binding of the compound known to bind to the human SNORF36a receptor is reduced in the presence of the plurality of compounds, relative to the binding of the compound in the absence of the plurality of compounds; and if so
   (d) separately determining the binding to the human SNORF36a receptor of each compound in the plurality of compounds, so as to thereby identify any compound which specifically binds to the human SNORF36a receptor;
wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

2. A method of screening a plurality of chemical compounds not known to bind to a human SNORF36a receptor to identify a compound which specifically binds to the human SNORF36a receptor, which comprises
   (a) contacting a membrane preparation from cells transfected with, and expressing, DNA encoding the human SNORF36a receptor with the plurality of compounds not known to bind specifically to the human SNORF36a receptor under conditions permitting binding of compounds known to bind to the human SNORF36a receptor;
   (b) determining whether the binding of a compound known to bind to the human SNORF36a receptor is reduced in the presence of the plurality of compounds, relative to the binding of the compound in the absence of the plurality of compounds; and if so
   (c) separately determining the binding to the human SNORF36a receptor of each compound in the plurality of compounds, so as to thereby identify any compound which specifically binds to the human SNORF36a receptor;
wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

3. The method of claim 1 or 2, wherein the cell is a mammalian cell.

4. The method of claim 3, wherein the mammalian cell is non-neuronal in origin.

5. The method of claim 4, wherein the non-neuronal cell is a COS-7 cell, a 293 human embryonic kidney cell, a LM(tk−) cell, a CHO cell, a mouse Y1 cell, or an NIH-3T3 cell.

6. A process for determining whether a chemical compound is a human SNORF36a receptor agonist which comprises contacting cells transfected with and expressing DNA encoding the human SNORF36a receptor with the compound under conditions permitting the activation of the human SNORF36a receptor, and detecting any increase in human SNORF36a receptor activity, so as to thereby determine whether the compound is a human SNORF36a receptor agonist, wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

7. A process for determining whether a chemical compound is a human SNORF36a receptor antagonist which comprises contacting cells transfected with and expressing DNA encoding the human SNORF36a receptor with the compound in the presence of a known human SNORF36a receptor agonist, under conditions permitting the activation of the human SNORF36a receptor, and detecting any decrease in human SNORF36a receptor activity, so as to thereby determine whether the compound is a human SNORF36a receptor antagonist, wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

8. A process for determining whether a chemical compound specifically binds to and activates a human SNORF36a receptor, which comprises contacting cells producing a second messenger response and expressing on their cell surface the human SNORF36a receptor, wherein such cells do not normally express the human SNORF36a receptor, with the chemical compound under conditions suitable for activation of the human SNORF36a receptor, and measuring the second messenger response in the presence and in the absence of the chemical compound, a change in the second messenger response in the presence of the chemical compound indicating that the compound activates the human SNORF36a receptor, wherein the human SNORF36a receptor has an amino acid sequence identical to the amino acid sequence shown in SEQ ID NO:2 or that encoded by plasmid pcDNA3.1-hSNORF36a-f (ATCC® Accession No.

9. The process of claim 8, wherein the second messenger response comprises chloride channel activation and the change in second messenger is an increase in the level of chloride current.

10. The process of claim 8, wherein the second messenger response comprises intracellular calcium levels and the change in second messenger is an increase in the measure of intracellular calcium.

11. The process of claim 8, wherein the second messenger response comprises release of inositol phosphate and the change in second messenger is an increase in the level of inositol phosphate.

12. A process for determining whether a chemical compound specifically binds to and inhibits activation of a human SNORF36a receptor, which comprises separately contacting cells producing a second messenger response and expressing on their cell surface the human SNORF36a receptor, wherein such cells do not normally express the human SNORF36a receptor, with both the chemical compound and a second chemical compound known to activate the human SNORF36a receptor, and with only the second chemical compound, under conditions suitable for activation of the human SNORF36a receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the human SNORF36a receptor, wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

13. The process of claim 12, wherein the second messenger response comprises chloride channel activation and the change in second messenger response is a smaller increase in the level of chloride current in the presence of both the chemical compound and the second chemical compound than in the presence of only the second chemical compound.

14. The process of claim 13, wherein the second messenger response comprises change in intracellular calcium levels and the change in second messenger response is a smaller increase in the measure of intracellular calcium in the presence of both the chemical compound and the second chemical compound than in the presence of only the second chemical compound.

15. The process of claim 12, wherein the second messenger response comprises release of inositol phosphate and the change in second messenger response is a smaller increase in the level of inositol phosphate in the presence of both the chemical compound and the second chemical compound than in the presence of only the second chemical compound.

16. The process of any one of claims 9, 10, 11, 12, 13, 14, or 15, wherein the cell is an insect cell.

17. The process of any one of claims 8, 9, 10, 11, 12, 13, 14, or 15, wherein the cell is a mammalian cell.

18. The process of claim 17, wherein the mammalian cell is nonneuronal in origin.

19. The process of claim 18, wherein the nonneuronal cell is a COS-7 cell, CHO cell, 293 human embryonic kidney cell, NIH-3T3 cell or LM(tk–) cell.

20. A method of screening a plurality of chemical compounds not known to activate a human SNORF36a receptor to identify a compound which activates the human SNORF36a receptor which comprises:
  (a) contacting cells transfected with and expressing the human SNORF36a receptor with the plurality of compounds not known to activate the human SNORF36a receptor, under conditions permitting activation of the human SNORF36a receptor;
  (b) determining whether the activity of the human SNORF36a receptor is increased in the presence of one or more of the compounds; and if so
  (c) separately determining whether the activation of the human SNORF36a receptor is increased by any compound in the plurality of compounds, so as to thereby identify each compound which activates the human SNORF36a receptor;
wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

21. A method of screening a plurality of chemical compounds not known to inhibit the activation of a human SNORF36a receptor to identify a compound which inhibits the activation of the human SNORF36a receptor, which comprises:
  (a) contacting cells transfected with and expressing the human SNORF36a receptor with the plurality of compounds in the presence of a known human SNORF36a receptor agonist, under conditions permitting activation of the human SNORF36a receptor;
  (b) determining whether the extent or amount of activation of the human SNORF36a receptor is reduced in the presence of one or more of the compounds, relative to the extent or amount of activation of the human SNORF36a receptor in the absence of such one or more compounds; and if so
  (c) separately determining whether each such compound inhibits activation of the human SNORF36a receptor for each compound in the plurality of compounds, so as to thereby identify any compound in such plurality of compounds which inhibits the activation of the human SNORF36a receptor;
wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

22. The method of any one of claims 20 or 21, wherein the cell is a mammalian cell.

23. The method of claim 22, wherein the mammalian cell is non-neuronal in origin.

24. The method of claim 23, wherein the non-neuronal cell is a COS-7 cell, a 293 human embryonic kidney cell, a LM(tk–) cell or an NIH-3T3 cell.

25. A process for identifying a chemical compound which specifically binds to a human SNORF36a receptor which comprises contacting cells containing DNA encoding, and expressing on their cell surface, the human SNORF36a receptor, wherein such cells do not normally express the human SNORF36a receptor, with the compound under conditions suitable for binding, and detecting specific binding of the chemical compound to the human SNORF36a receptor, wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

26. A process for identifying a chemical compound which specifically binds to a human SNORF36a receptor which comprises contacting a membrane preparation from cells containing DNA encoding, and expressing on their cell surface, the human SNORF36a receptor, wherein such cells do not normally express the human SNORF36a receptor, with the compound under conditions suitable for binding, and detecting specific binding of the chemical compound to the human SNORF36a receptor, wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

27. The process of claim 25 or 26, wherein the cell is an insect cell.

28. The process of claim 25 or 26, wherein the cell is a mammalian cell.

29. The process of claim 28, wherein the cell is nonneuronal in origin.

30. The process of claim 29, wherein the nonneuronal cell is a COS-7 cell, 293 human embryonic kidney cell, a CHO cell, a NIH-3T3 cell, a mouse Y1 cell, or a LM(tk–) cell.

31. A process involving competitive binding for identifying a chemical compound which specifically binds to a human SNORF36a receptor which comprises separately contacting cells expressing on their cell surface the human SNORF36a receptor, wherein such cells do not normally express the human SNORF36a receptor, with both the chemical compound and a second chemical compound known to bind to the receptor, and with only the second chemical compound, under conditions suitable for binding of such compounds to the receptor, and detecting specific binding of the chemical compound to the human SNORF36a receptor, a decrease in the binding of the second chemical compound to the human SNORF36a receptor in the presence of the chemical compound being tested indicating that such chemical compound binds to the human SNORF36a receptor, wherein the human SNORF36a receptor has an amino acid sequence identical to the amino acid sequence shown in SEQ ID NO:2 or that encoded by plasmid pcDNA3.1-hSNORF36a-f (ATCC® Accession No. 203977).

32. A process involving competitive binding for identifying a chemical compound which specifically binds to a human SNORF36a receptor which comprises separately contacting a membrane preparation from cells expressing on their cell surface the human SNORF36a receptor, wherein such cells do not normally express the human SNORF36a receptor, with both the chemical compound and a second chemical compound known to bind to the receptor, and with only the second chemical compound, under conditions suitable for binding of such compounds to the receptor, and detecting specific binding of the chemical compound to the human SNORF36a receptor, a decrease in the binding of the second chemical compound to the human SNORF36a receptor in the presence of the chemical compound being tested indicating that such chemical compound binds to the human SNORF36a receptor, wherein the human SNORF36a receptor has an amino acid sequence identical to the amino acid sequence shown in SEQ ID NO:2 or that encoded by plasmid pcDNA3.1-hSNORF36a-f (ATCC® Accession No. 2097).

33. The process of claim 31 or 32, wherein the cell is an insect cell.

34. The process of claim 31 or 32, wherein the cell is a mammalian cell.

35. The process of claim 34, wherein the cell is nonneuronal in origin.

36. The process of claim 35, wherein the nonneuronal cell is a COS-7 cell, 293 human embryonic kidney cell, a CHO cell, a NIH-3T3 cell, a mouse Y1 cell, or a LM(tk−) cell.

* * * * *

SEQUENCE LISTING

<160> NUMBER OF SEQ ID NOS: 44

<210> SEQ ID NO 1
<211> LENGTH: 1508
<212> TYPE: DNA
<213> ORGANISM: Homo sapiens

<400> SEQUENCE: 1

```
caactcagga tgaaccctcc ttcggggcca agagtcccgc ccagcccaac ccaagagccc      60
agctgcatgg ccaccccagc accacccagc tggtgggaca gctcccagag cagcatctcc     120
agcctgggcc ggcttccatc catcagtccc acagcacctg ggacttgggc tgctgcctgg     180 gtcccctcc ccacggttga tgttccagac catgcccact ataccctggg cacagtgatc      240
ttgctggtgg gactcacggg gatgctgggc aacctgacgg tcatctatac cttctgcagg     300
agcagaagcc tccggacacc tgccaacatg ttcattatca acctcgcggt cagcgacttc     360
ctcatgtcct tcacccaggc ccctgtcttc ttcaccagta gcctctataa gcagtggctc     420
tttggggaga caggctgcga gttctatgcc ttctgtggag ctctctttgg catttcctcc     480
atgatcaccc tgacggccat cgccctggac cgctacctgg taatcacacg cccgctggcc     540
```

-continued

```
acctttggtg tggcgtccaa gaggcgtgcg gcatttgtcc tgctgggcgt ttggctctat    600
gccctggcct ggagtctgcc acccttcttc ggctggagcg cctacgtgcc cgaggggttg    660
ctgacatcct gctcctggga ctacatgagc ttcacgccgg ccgtgcgtgc ctacaccatg    720
cttctctgct gcttcgtgtt cttcctccct ctgcttatca tcatctactg ctacatcttc    780
atcttcaggg ccatccggga gacaggacgg gctctccaga ccttcggggc ctgcaagggc    840
aatggcgagt ccctgtggca gcggcagcgg ctgcagagcg agtgcaagat ggccaagatc    900
atgctgctgg tcatcctcct cttcgtgctc tcctgggctc cctattccgc gtgtggccctg    960
gtggcctttg ctgggtacgc acacgtcctg cacccctaca tgagctcggt gccagccgtc   1020
atcgccaagg cctctgcaat ccacaacccc atcatttacg ccatcaccca ccccaagtac   1080
agggtggcca ttgcccagca cctgccctgc ctgggggtgc tgctgggtgt atcacgccgg   1140
cacagtcgcc cctaccccag ctaccgctcc acccaccgct ccacgctgac cagccacacc   1200
tccaacctca gctggatctc catacggagg cgccaggagt ccctgggctc ggagagtgag   1260
gtgggctgga cacacatgga ggcagcagct gtgtggggag ctgcccagca agcaaatggg   1320
cggtccctct acggtcaggg tctggaggac ttggaagcca aggcaccccc cagacccag   1380
ggacacgaag cagagactcc agggaagacc aaggggctga tccccagcca ggaccccagg   1440
atgtaggacg cccactggct ctcccttct tctgagacac atccagccc cccacgtctc   1500
cctcatat                                                           1508
```

<210> SEQ ID NO 2
<211> LENGTH: 478
<212> TYPE: PRT
<213> ORGANISM: Homo sapiens

<400> SEQUENCE: 2

```
Met Asn Pro Pro Ser Gly Pro Arg Val Pro Ser Pro Thr Gln Glu
  1               5                  10                  15

Pro Ser Cys Met Ala Thr Pro Ala Pro Pro Ser Trp Trp Asp Ser Ser
                 20                  25                  30

Gln Ser Ser Ile Ser Ser Leu Gly Arg Leu Pro Ser Ile Ser Pro Thr
             35                  40                  45

Ala Pro Gly Thr Trp Ala Ala Ala Trp Val Pro Leu Pro Thr Val Asp
         50                  55                  60

Val Pro Asp His Ala His Tyr Thr Leu Gly Thr Val Ile Leu Leu Val
 65                  70                  75                  80

Gly Leu Thr Gly Met Leu Gly Asn Leu Thr Val Ile Tyr Thr Phe Cys
                 85                  90                  95

Arg Ser Arg Ser Leu Arg Thr Pro Ala Asn Met Phe Ile Ile Asn Leu
            100                 105                 110

Ala Val Ser Asp Phe Leu Met Ser Phe Thr Gln Ala Pro Val Phe Phe
        115                 120                 125

Thr Ser Ser Leu Tyr Lys Gln Trp Leu Phe Gly Glu Thr Gly Cys Glu
    130                 135                 140

Phe Tyr Ala Phe Cys Gly Ala Leu Phe Gly Ile Ser Ser Met Ile Thr
145                 150                 155                 160

Leu Thr Ala Ile Ala Leu Asp Arg Tyr Leu Val Ile Thr Arg Pro Leu
                165                 170                 175

Ala Thr Phe Gly Val Ala Ser Lys Arg Arg Ala Ala Phe Val Leu Leu
            180                 185                 190
```

-continued

```
Gly Val Trp Leu Tyr Ala Leu Ala Trp Ser Leu Pro Pro Phe Phe Gly
            195                 200                 205

Trp Ser Ala Tyr Val Pro Glu Gly Leu Leu Thr Ser Cys Ser Trp Asp
        210                 215                 220

Tyr Met Ser Phe Thr Pro Ala Val Arg Ala Tyr Thr Met Leu Leu Cys
225                 230                 235                 240

Cys Phe Val Phe Leu Pro Leu Leu Ile Ile Ile Tyr Cys Tyr Ile
                245                 250                 255

Phe Ile Phe Arg Ala Ile Arg Glu Thr Gly Arg Ala Leu Gln Thr Phe
                260                 265                 270

Gly Ala Cys Lys Gly Asn Gly Glu Ser Leu Trp Gln Arg Gln Arg Leu
            275                 280                 285

Gln Ser Glu Cys Lys Met Ala Lys Ile Met Leu Leu Val Ile Leu Leu
        290                 295                 300

Phe Val Leu Ser Trp Ala Pro Tyr Ser Ala Val Ala Leu Val Ala Phe
305                 310                 315                 320

Ala Gly Tyr Ala His Val Leu Thr Pro Tyr Met Ser Ser Val Pro Ala
                325                 330                 335

Val Ile Ala Lys Ala Ser Ala Ile His Asn Pro Ile Ile Tyr Ala Ile
            340                 345                 350

Thr His Pro Lys Tyr Arg Val Ala Ile Ala Gln His Leu Pro Cys Leu
        355                 360                 365

Gly Val Leu Leu Gly Val Ser Arg Arg His Ser Arg Pro Tyr Pro Ser
370                 375                 380

Tyr Arg Ser Thr His Arg Ser Thr Leu Thr Ser His Thr Ser Asn Leu
385                 390                 395                 400

Ser Trp Ile Ser Ile Arg Arg Arg Gln Glu Ser Leu Gly Ser Glu Ser
                405                 410                 415

Glu Val Gly Trp Thr His Met Glu Ala Ala Val Trp Gly Ala Ala
            420                 425                 430

Gln Gln Ala Asn Gly Arg Ser Leu Tyr Gly Gln Gly Leu Glu Asp Leu
        435                 440                 445

Glu Ala Lys Ala Pro Pro Arg Pro Gln Gly His Glu Ala Glu Thr Pro
450                 455                 460

Gly Lys Thr Lys Gly Leu Ile Pro Ser Gln Asp Pro Arg Met
465                 470                 475

<210> SEQ ID NO 3
<211> LENGTH: 1541
<212> TYPE: DNA
<213> ORGANISM: Homo sapiens

<400> SEQUENCE: 3
caactcagga tgaaccctcc ttcggggcca agagtcccgc ccagcccaac ccaagagccc      60
agctgcatgg ccaccccagc accacccagc tggtgggaca gctcccagag cagcatctcc     120
agcctgggcc ggcttccatc catcagtccc acagcacctg ggacttgggc tgctgcctgg     180
gtccccctcc ccacggttga tgttccagac catgcccact atccctgggc acagtgatc     240 ttgctggtgg gactcacggg gatgctgggc aacctgacgg tcatctatac cttctgcaga     300
gctgtgcttc gtggagtcac tgtgatgatg cagagcagaa gcctccggac acctgccaac     360
atgttcatta tcaacctcgc ggtcagcgac ttcctcatgt ccttcacccca ggccctgtc     420 ttcttcacca gtagcctcta taagcagtgg ctctttgggg agacaggctg cgagttctat     480
gccttctgtg gagctctctt tggcatttcc tccatgatca ccctgacggc catcgccctg     540
```

-continued

```
gaccgctacc tggtaatcac acgcccgctg gccacctttg gtgtggcgtc caagaggcgt    600
gcggcatttg tcctgctggg cgtttggctc tatgccctgg cctggagtct gccacccttc    660
ttcggctgga gcgcctacgt gcccgagggg ttgctgacat cctgctcctg ggactacatg    720
agcttcacgc cggccgtgcg tgcctacacc atgcttctct gctgcttcgt gttcttcctc    780
cctctgctta tcatcatcta ctgctacatc ttcatcttca gggccatccg ggagacagga    840
cgggctctcc agaccttcgg ggcctgcaag ggcaatggcg agtccctgtg cagcggcag     900 cggctgcaga gcgagtgcaa gatggccaag atcatgctgc tggtcatcct cctcttcgtg    960
ctctcctggg ctccctattc cgctgtggcc ctggtggcct ttgctgggta cgcacacgtc   1020
ctgacaccct acatgagctc ggtgccagcc gtcatcgcca aggcctctgc aatccacaac   1080
cccatcattt acgccatcac ccaccccaag tacagggtgg ccattgccca gcacctgccc   1140
tgcctggggg tgctgctggg tgtatcacgc cggcacagtc gcccctaccc cagctaccgc   1200
tccacccacc gctccacgct gaccagccac acctccaacc tcagctggat ctccatacgg   1260
aggcgccagt agtccctggg ctcggagagt gaggtgggct ggacacacat ggaggcagca   1320
gctgtgtggg gagctgccca gcaagcaaat gggcggtccc tctacggtca gggtctggag   1380
gacttggaag ccaaggcacc ccccagaccc agggacacg aagcagagac tccagggaag   1440
accaaggggc tgatccccag ccaggacccc aggatgtagg acgcccactg gctctccctt   1500
tcttctgaga cacatccagc ccccccacgt ctccctcata t                       1541
```

<210> SEQ ID NO 4
<211> LENGTH: 489
<212> TYPE: PRT
<213> ORGANISM: Homo sapiens

<400> SEQUENCE: 4

```
Met Asn Pro Pro Ser Gly Pro Arg Val Pro Ser Pro Thr Gln Glu
  1               5                  10                  15

Pro Ser Cys Met Ala Thr Pro Ala Pro Pro Ser Trp Trp Asp Ser Ser
                 20                  25                  30

Gln Ser Ser Ile Ser Ser Leu Gly Arg Leu Pro Ser Ile Ser Pro Thr
             35                  40                  45

Ala Pro Gly Thr Trp Ala Ala Ala Trp Val Pro Leu Pro Thr Val Asp
         50                  55                  60

Val Pro Asp His Ala His Tyr Thr Leu Gly Thr Val Ile Leu Leu Val
 65                  70                  75                  80

Gly Leu Thr Gly Met Leu Gly Asn Leu Thr Val Ile Tyr Thr Phe Cys
                 85                  90                  95

Arg Ala Val Leu Arg Gly Val Thr Val Met Met Gln Ser Arg Ser Leu
                100                 105                 110

Arg Thr Pro Ala Asn Met Phe Ile Ile Asn Leu Ala Val Ser Asp Phe
            115                 120                 125

Leu Met Ser Phe Thr Gln Ala Pro Val Phe Phe Thr Ser Ser Leu Tyr
        130                 135                 140

Lys Gln Trp Leu Phe Gly Glu Thr Gly Cys Glu Phe Tyr Ala Phe Cys
145                 150                 155                 160

Gly Ala Leu Phe Gly Ile Ser Ser Met Ile Thr Leu Thr Ala Ile Ala
                165                 170                 175

Leu Asp Arg Tyr Leu Val Ile Thr Arg Pro Leu Ala Thr Phe Gly Val
            180                 185                 190
```

-continued

```
Ala Ser Lys Arg Arg Ala Ala Phe Val Leu Leu Gly Val Trp Leu Tyr
            195                 200                 205
Ala Leu Ala Trp Ser Leu Pro Pro Phe Phe Gly Trp Ser Ala Tyr Val
    210                 215                 220
Pro Glu Gly Leu Leu Thr Ser Cys Ser Trp Asp Tyr Met Ser Phe Thr
225                 230                 235                 240
Pro Ala Val Arg Ala Tyr Thr Met Leu Leu Cys Cys Phe Val Phe Phe
                245                 250                 255
Leu Pro Leu Leu Ile Ile Ile Tyr Cys Tyr Ile Phe Ile Phe Arg Ala
            260                 265                 270
Ile Arg Glu Thr Gly Arg Ala Leu Gln Thr Phe Gly Ala Cys Lys Gly
        275                 280                 285
Asn Gly Glu Ser Leu Trp Gln Arg Gln Arg Leu Gln Ser Glu Cys Lys
    290                 295                 300
Met Ala Lys Ile Met Leu Leu Val Ile Leu Leu Phe Val Leu Ser Trp
305                 310                 315                 320
Ala Pro Tyr Ser Ala Val Ala Leu Val Ala Phe Ala Gly Tyr Ala His
                325                 330                 335
Val Leu Thr Pro Tyr Met Ser Ser Val Pro Ala Val Ile Ala Lys Ala
            340                 345                 350
Ser Ala Ile His Asn Pro Ile Ile Tyr Ala Ile Thr His Pro Lys Tyr
        355                 360                 365
Arg Val Ala Ile Ala Gln His Leu Pro Cys Leu Gly Val Leu Leu Gly
    370                 375                 380
Val Ser Arg Arg His Ser Arg Pro Tyr Pro Ser Tyr Arg Ser Thr His
385                 390                 395                 400
Arg Ser Thr Leu Thr Ser His Thr Ser Asn Leu Ser Trp Ile Ser Ile
                405                 410                 415
Arg Arg Arg Gln Glu Ser Leu Gly Ser Glu Ser Glu Val Gly Trp Thr
            420                 425                 430
His Met Glu Ala Ala Ala Val Trp Gly Ala Ala Gln Gln Ala Asn Gly
        435                 440                 445
Arg Ser Leu Tyr Gly Gln Gly Leu Glu Asp Leu Glu Ala Lys Ala Pro
    450                 455                 460
Pro Arg Pro Gln Gly His Glu Ala Glu Thr Pro Gly Lys Thr Lys Gly
465                 470                 475                 480
Leu Ile Pro Ser Gln Asp Pro Arg Met
                485
```

<210> SEQ ID NO 5
<211> LENGTH: 250
<212> TYPE: DNA
<213> ORGANISM: Rattus norvegicus

<400> SEQUENCE: 5

```
catagccatg gaccgctatc tggtgatcac acgtccactg gccaccatcg gcatgagatc     60
caagagacgg acggcactag tcctgctagg tgtctggctc tatgccctgg cctggagtct    120
gccgcctttc tttggctgga gcgcctacgt gcccgagggg ctgctgacat cctgctcctg    180
ggactacgtg accttcacgc ccctcgtgcg cgcctacacc atgctgctct tctgctttgt    240
cttcttcctc                                                          250
```

<210> SEQ ID NO 6
<211> LENGTH: 83
<212> TYPE: PRT

```
<213> ORGANISM: Rattus norvegicus

<400> SEQUENCE: 6

Ile Ala Met Asp Arg Tyr Leu Val Ile Thr Arg Pro Leu Ala Thr Ile
 1               5                  10                  15

Gly Met Arg Ser Lys Arg Arg Thr Ala Leu Val Leu Leu Gly Val Trp
                20                  25                  30

Leu Tyr Ala Leu Ala Trp Ser Leu Pro Pro Phe Phe Gly Trp Ser Ala
            35                  40                  45

Tyr Val Pro Glu Gly Leu Leu Thr Ser Cys Ser Trp Asp Tyr Val Thr
50                  55                  60

Phe Thr Pro Leu Val Arg Ala Tyr Thr Met Leu Leu Phe Cys Phe Val
65                  70                  75                  80

Phe Phe Leu

<210> SEQ ID NO 7
<211> LENGTH: 1473
<212> TYPE: DNA
<213> ORGANISM: Rattus norvegicus

<400> SEQUENCE: 7
tttaagtcct ccaagagcct gagcatgaac tctccttcag aatcaagagt cccttcaagc      60
ttaactcagg atcccagctt taccgccagc cctgccctcc tacaaggcat ttggaacagc     120
actcagaaca tctccgtcag agtccagctt ctatccgtta gccccacgac acctgggctt     180
caggctgctg cctgggtccc cttccccaca gtcgacgtcc cagatcatgc tcactatacc     240
ctaggcacgt gatcctgct ggtgggactc acagggatgc tgggtaacct gacagtcatc     300
tacaccttct gcaggaatag aggcctgcgg acaccggcaa acatgctcat catcaacctg     360
gcagtcagcg acttccttat gtcgttcact caggccccgg tcttctttgc cagcagcctc     420
tacaagaagt ggctcttcgg ggagacaggt tgcaagttct atgccttctg tggggctgtc     480
tttggcatcg tttccatgat caccctgaca gccatagcca tggaccgcta tctggtgatc     540
acacgtccac tggccaccat cggcatgaga tccaagagac ggacggcact agtcctgcta     600
ggtgtctggc tctatgccct ggcctggagt ctgccgcctt cctttggctg gagcgcctac     660
gtgcccgagg gcctgctgac atcctgctcc tgggactacg tgaccttcac gcccctcgtg     720
cgcgcctaca ccatgctgct cttctgcttt gtcttcttcc tccctctgct cattatcatc     780
ttctgctaca tcttcatctt cagggccatt cgagagacag gccgggcctg tgagggctgt     840
ggtgagtccc ctctgcggcg gcggcagtgg cagcggctac agagtgaatg gaagatggcc     900
aaggtcgcac tgatcgtcat tctcctcttt gtgctgtcct gggctcccta ctccactgtg     960
gccctggtgg gctttgctgg gtactcgcac atcctgacgc cctacatgag ctcggtgcca    1020
gccgtcattg ccaaggcctc ggccatccac aatcctatca tctatgccat cactcacccc    1080
aagtacaggg cggccattgc tcagcacttg ccttgccttg gggtgcttct tggagtatca    1140
ggccagcgca gccaccccct cctcagctac cgctctaccc atcgctccac actgagcagc    1200
cagtcctcag acctcagctg gatctctggg cagaagcgcc aagagtccct gggttctgag    1260
agtgaagtgg gctggacaga cacagaaaca acagctgcgt ggggagctgc ccagcaagca    1320
agtggacaat ccttctgcag tcatgacctg gaagatggag aagtcaaggc ccttccagc    1380
ccccaggaac agaaatccaa gactcccaag accaagagac acctcccag tctggaccga    1440
aggatgtagg atgcccagtc ccgtcccctc cct                                 1473
```

-continued

```
<210> SEQ ID NO 8
<211> LENGTH: 474
<212> TYPE: PRT
<213> ORGANISM: Rattus norvegicus

<400> SEQUENCE: 8

Met Asn Ser Pro Ser Glu Ser Arg Val Pro Ser Ser Leu Thr Gln Asp
 1               5                  10                  15

Pro Ser Phe Thr Ala Ser Pro Ala Leu Leu Gln Gly Ile Trp Asn Ser
            20                  25                  30

Thr Gln Asn Ile Ser Val Arg Val Gln Leu Leu Ser Val Ser Pro Thr
        35                  40                  45

Thr Pro Gly Leu Gln Ala Ala Trp Val Pro Phe Pro Thr Val Asp
    50                  55                  60

Val Pro Asp His Ala His Tyr Thr Leu Gly Thr Val Ile Leu Leu Val
 65                  70                  75                  80

Gly Leu Thr Gly Met Leu Gly Asn Leu Thr Val Ile Tyr Thr Phe Cys
                85                  90                  95

Arg Asn Arg Gly Leu Arg Thr Pro Ala Asn Met Leu Ile Ile Asn Leu
            100                 105                 110

Ala Val Ser Asp Phe Leu Met Ser Phe Thr Gln Ala Pro Val Phe Phe
        115                 120                 125

Ala Ser Ser Leu Tyr Lys Lys Trp Leu Phe Gly Glu Thr Gly Cys Lys
    130                 135                 140

Phe Tyr Ala Phe Cys Gly Ala Val Phe Gly Ile Val Ser Met Ile Thr
145                 150                 155                 160

Leu Thr Ala Ile Ala Met Asp Arg Tyr Leu Val Ile Thr Arg Pro Leu
                165                 170                 175

Ala Thr Ile Gly Met Arg Ser Lys Arg Arg Thr Ala Leu Val Leu Leu
            180                 185                 190

Gly Val Trp Leu Tyr Ala Leu Ala Trp Ser Leu Pro Pro Phe Phe Gly
        195                 200                 205

Trp Ser Ala Tyr Val Pro Glu Gly Leu Leu Thr Ser Cys Ser Trp Asp
    210                 215                 220

Tyr Val Thr Phe Thr Pro Leu Val Arg Ala Tyr Thr Met Leu Leu Phe
225                 230                 235                 240

Cys Phe Val Phe Phe Leu Pro Leu Leu Ile Ile Ile Phe Cys Tyr Ile
                245                 250                 255

Phe Ile Phe Arg Ala Ile Arg Glu Thr Gly Arg Ala Cys Glu Gly Cys
            260                 265                 270

Gly Glu Ser Pro Leu Arg Arg Gln Trp Gln Arg Leu Gln Ser Glu
        275                 280                 285

Trp Lys Met Ala Lys Val Ala Leu Ile Val Ile Leu Leu Phe Val Leu
    290                 295                 300

Ser Trp Ala Pro Tyr Ser Thr Val Ala Leu Val Gly Phe Ala Gly Tyr
305                 310                 315                 320

Ser His Ile Leu Thr Pro Tyr Met Ser Ser Val Pro Ala Val Ile Ala
                325                 330                 335

Lys Ala Ser Ala Ile His Asn Pro Ile Ile Tyr Ala Ile Thr His Pro
            340                 345                 350

Lys Tyr Arg Ala Ala Ile Ala Gln His Leu Pro Cys Leu Gly Val Leu
        355                 360                 365

Leu Gly Val Ser Gly Gln Arg Ser His Pro Ser Leu Ser Tyr Arg Ser
    370                 375                 380
```

```
Thr His Arg Ser Thr Leu Ser Ser Gln Ser Ser Asp Leu Ser Trp Ile
385                 390                 395                 400

Ser Gly Gln Lys Arg Gln Glu Ser Leu Gly Ser Glu Ser Glu Val Gly
                405                 410                 415

Trp Thr Asp Thr Glu Thr Thr Ala Ala Trp Gly Ala Ala Gln Gln Ala
            420                 425                 430

Ser Gly Gln Ser Phe Cys Ser His Asp Leu Glu Asp Gly Glu Val Lys
                435                 440                 445

Ala Pro Ser Ser Pro Gln Glu Gln Lys Ser Lys Thr Pro Lys Thr Lys
        450                 455                 460

Arg His Leu Pro Ser Leu Asp Arg Arg Met
465                 470
```

```
<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 9
catcgccctc gacgtgctgt gctgcacctc atccatcttg cacct          45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 10
catggacagg tcgcgctacc gcgtgtccac gttctaccta ctcca          45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 11
ggcatcatca tgggcacctt catcctctgc tggctgccct tcttc          45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 12
gcagaagggc agaacaagag ccacgatgaa gaagggcagc cagca          45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence:
      Primer/Probe
```

<400> SEQUENCE: 13
tggctgtcat cggacatcac ttgttgcact gcctccatcc tgcac                45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 14
gtagcggtcc agggcgatga cacagaggtg caggatggag gcagt                45

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 15
ccagccgaag aagggtggca gactcca                                    27

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 16
cttctaggcc tgtacggaag tgtta                                      25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 17
gcacaggctg cgagttctat tcctt                                      25

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 18
ctggtaatca cacccgct ggccaccttt ggtgtggcgt ccaag                  45

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:
      Primer/Probe -continued

```
<400> SEQUENCE: 19
agatcatgct gctggtcatc ctcc                                        24

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 20
tcgtgctctc ctgggctccc t                                           21

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 21
tcctccatga tcaccctgac ggc                                         23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 22
tctggagagc ccgtcctgtc tcc                                         23

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 23
cggccgtgcg tgcctacacc atgcttctct gctgcttcgt gttcttcc              48

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 24
ttggacgcca caccaaaggt ggcc                                        24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 25
```

```
ggtatagatg accgtcaggt tgcc                                    24

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 26
cgaacaggat cctctctgtg ggctcgagca aggacc                       36

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 27
acgtgtgcgt acccagcaaa ggcc                                    24

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 28
gtcccacagc acctgggact tgggctgc                                28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 29
gcagcccaag tcccaggtgc tgtgggac                                28

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 30
ggcaacctga cggtcatcta tacc                                    24

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 31
```
cagcataagc ttccagtggg cgtcctacat cctgg                                    35

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 32
cagtagatga tgataagcag agg                                                 23

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 33
cgaacaggat cccatagcca tggaccgcta tctgg                                    35

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 34
cctagcaagc ttgaggaaga agacaaagca gaagagc                                  37

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence:
      Primer/Probe

<400> SEQUENCE: 35
cggacggcac tagtcctgct aggtgtctgg ctctatgccc tggcctgg                      48

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 36
ggctgcgagt tctatgcctt                                                     20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 37
ttaccaggta gcggtccagg                                                     20

```
<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Probe

<400> SEQUENCE: 38
agctctcttt ggcatttcct ccatgatca                              29

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 39
ctgggcaacc tgacggtc                                          18

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 40
caggtgtccg gaggcttct                                         19

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Probe

<400> SEQUENCE: 41
tgtgcttcgt ggagtcactg tgatgat                                27

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 42
tccactggcc accatcg                                           17

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 43
gggcatagag ccagacacct ag                                     22

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Probe
```

-continued

<400> SEQUENCE: 44
catgagatcc aagagacgga cggca                                    25